(12) United States Patent
Hibner et al.

(10) Patent No.: US 10,342,567 B2
(45) Date of Patent: Jul. 9, 2019

(54) ULTRASONIC SURGICAL INSTRUMENT WITH OPPOSING THREAD DRIVE FOR END EFFECTOR ARTICULATION

(71) Applicant: Ethicon Endo-Surgery, LLC, Guaynabo, PR (US)

(72) Inventors: John A. Hibner, Mason, OH (US); Rudolph H. Nobis, Mason, OH (US); Benjamin J. Danziger, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 486 days.

(21) Appl. No.: 14/688,663

(22) Filed: Apr. 16, 2015

(65) Prior Publication Data

US 2016/0302820 A1 Oct. 20, 2016

(51) Int. Cl.
*A61B 17/32* (2006.01)
*A61B 17/00* (2006.01)
*A61B 17/29* (2006.01)

(52) U.S. Cl.
CPC ........ *A61B 17/320092* (2013.01); *A61B 17/320016* (2013.01); *A61B 2017/00314* (2013.01); *A61B 2017/00327* (2013.01); *A61B 2017/00367* (2013.01); *A61B 2017/00424* (2013.01); *A61B 2017/2925* (2013.01);
(Continued)

(58) Field of Classification Search
CPC ......... A61B 17/28; A61B 17/29; A61B 17/32; A61B 17/320016; A61B 17/32002; A61B 17/320068; A61B 17/320092; A61B 2017/003; A61B 2017/00305; A61B 2017/00318; A61B 2017/00323; A61B 2017/2908; A61B 2017/2927; A61B 2017/320069; A61B 2017/320071
See application file for complete search history.

(56) References Cited

U.S. PATENT DOCUMENTS

| | | |
|---|---|---|
| 2,906,143 A | 9/1959 | Walton |
| 5,322,055 A | 6/1994 | Davison et al. |
| 5,873,873 A | 2/1999 | Smith et al. |

(Continued)

OTHER PUBLICATIONS

U.S. Appl. No. 14/258,179, filed Apr. 22, 2014.
(Continued)

*Primary Examiner* — Todd J Scherbel
(74) *Attorney, Agent, or Firm* — Frost Brown Todd LLC

(57) ABSTRACT

An apparatus comprises a body assembly, a shaft assembly, an end effector, an articulation section, and an articulation control assembly. The end effector is located at a distal end of the shaft assembly and comprises an ultrasonic blade. The articulation section is coupled with the shaft assembly and is operable to articulate to thereby deflect the end effector from the longitudinal axis. The articulation control assembly comprises first and second threaded members and an articulation control. The first and second threaded members have respective first and second pitch orientations. The articulation control is rotatable to thereby drive articulation of the articulation section by causing translation of the first and second threaded members along a path that is parallel to the longitudinal axis of the shaft assembly. The axis of rotation of the articulation control is non-parallel with the longitudinal axis of the shaft assembly.

20 Claims, 53 Drawing Sheets

(52) U.S. Cl.
CPC .......... *A61B 2017/2943* (2013.01); *A61B 2017/2946* (2013.01); *A61B 2017/320052* (2013.01)

(56) References Cited

U.S. PATENT DOCUMENTS

| | | | |
|---|---|---|---|
| 5,897,523 A | 4/1999 | Wright et al. | |
| 5,980,510 A | 11/1999 | Tsonton et al. | |
| 5,989,264 A | 11/1999 | Wright | |
| 6,063,098 A | 5/2000 | Houser et al. | |
| 6,090,120 A | 7/2000 | Wright et al. | |
| 6,325,811 B1 | 12/2001 | Messerly | |
| 6,454,782 B1 | 9/2002 | Schwemberger | |
| 6,589,200 B1 | 7/2003 | Schwemberger et al. | |
| 6,752,815 B2 | 6/2004 | Beaupre | |
| 6,773,444 B2 | 8/2004 | Messerly | |
| 6,783,524 B2 | 8/2004 | Anderson et al. | |
| 7,111,769 B2 * | 9/2006 | Wales .............. | A61B 17/07207 227/175.1 |
| 7,135,030 B2 | 11/2006 | Schwemberger | |
| 7,621,930 B2 | 11/2009 | Houser | |
| 8,100,824 B2 | 1/2012 | Hegeman et al. | |
| 8,105,350 B2 | 1/2012 | Lee et al. | |
| 8,292,889 B2 | 10/2012 | Cunningham et al. | |
| 8,461,744 B2 | 6/2013 | Wiener et al. | |
| 8,574,263 B2 | 11/2013 | Mueller et al. | |
| 8,591,536 B2 | 11/2013 | Robertson | |
| 8,623,027 B2 | 1/2014 | Price et al. | |
| 8,968,312 B2 | 3/2015 | Marczyk et al. | |
| 8,968,357 B2 | 3/2015 | Mueller et al. | |
| 8,986,302 B2 | 3/2015 | Aldridge et al. | |
| 9,023,071 B2 | 5/2015 | Miller et al. | |
| 9,072,536 B2 | 7/2015 | Shelton et al. | |
| 9,095,367 B2 | 8/2015 | Olson et al. | |
| 9,220,559 B2 | 12/2015 | Worrell et al. | |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2007/0287993 A1 | 12/2007 | Hinman et al. | |
| 2008/0200940 A1 | 8/2008 | Eichmann et al. | |
| 2009/0281556 A1 * | 11/2009 | Newell .............. | A61B 17/0401 606/144 |
| 2011/0213363 A1 * | 9/2011 | Cunningham ..... | A61B 18/1445 606/41 |
| 2012/0078243 A1 | 3/2012 | Worrell et al. | |
| 2012/0078244 A1 | 3/2012 | Worrell et al. | |
| 2012/0078247 A1 | 3/2012 | Worrell et al. | |
| 2012/0112687 A1 | 5/2012 | Houser et al. | |
| 2012/0116265 A1 | 5/2012 | Houser et al. | |
| 2013/0023868 A1 | 1/2013 | Worrell et al. | |
| 2013/0023923 A1 * | 1/2013 | Mueller .............. | A61B 17/29 606/205 |
| 2013/0267936 A1 * | 10/2013 | Stroup .............. | A61B 17/29 606/1 |
| 2013/0289592 A1 | 10/2013 | Stulen et al. | |
| 2014/0005701 A1 | 1/2014 | Olson et al. | |
| 2014/0005703 A1 | 1/2014 | Stulen et al. | |
| 2015/0014392 A1 | 1/2015 | Williams et al. | |
| 2015/0080924 A1 | 3/2015 | Stulen et al. | |
| 2015/0245850 A1 | 9/2015 | Hibner et al. | |

OTHER PUBLICATIONS

U.S. Appl. No. 61/410,603, filed Nov. 5, 2010.
International Search Report and Written Opinion dated Oct. 31, 2016 re Application No. PCT/US16/27693.

\* cited by examiner

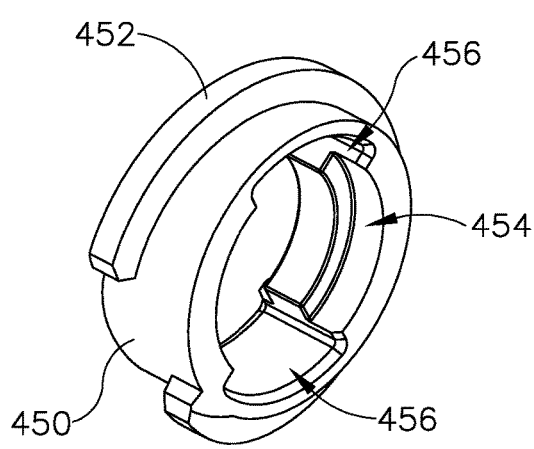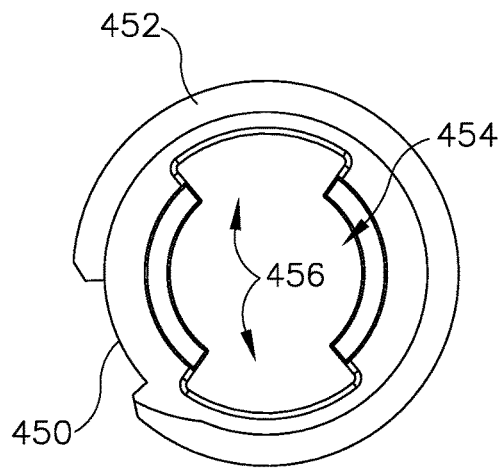
Fig.20　　　　　Fig.21
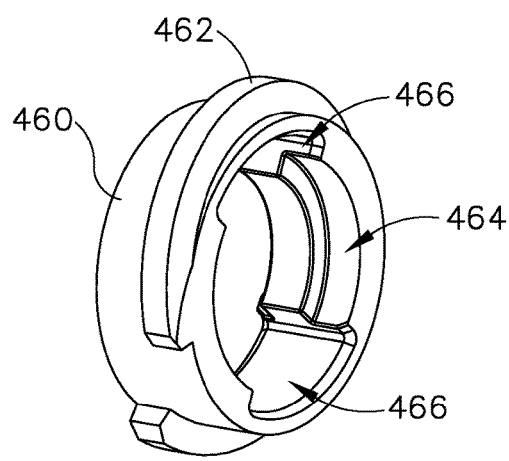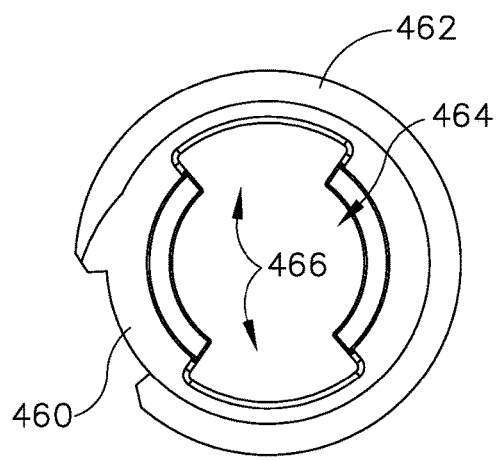
Fig.22　　　　　Fig.23

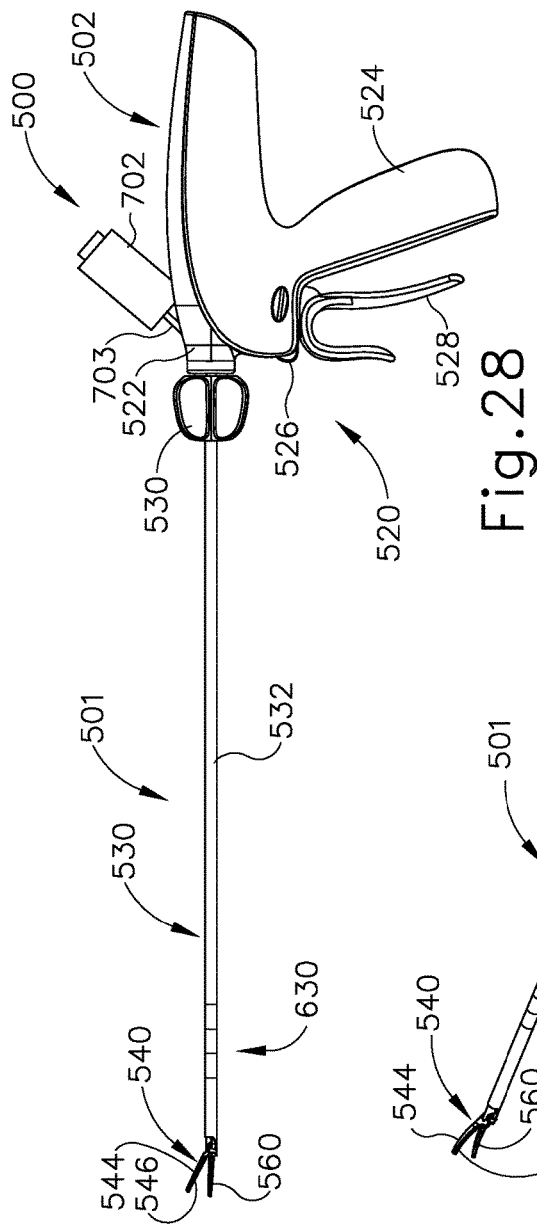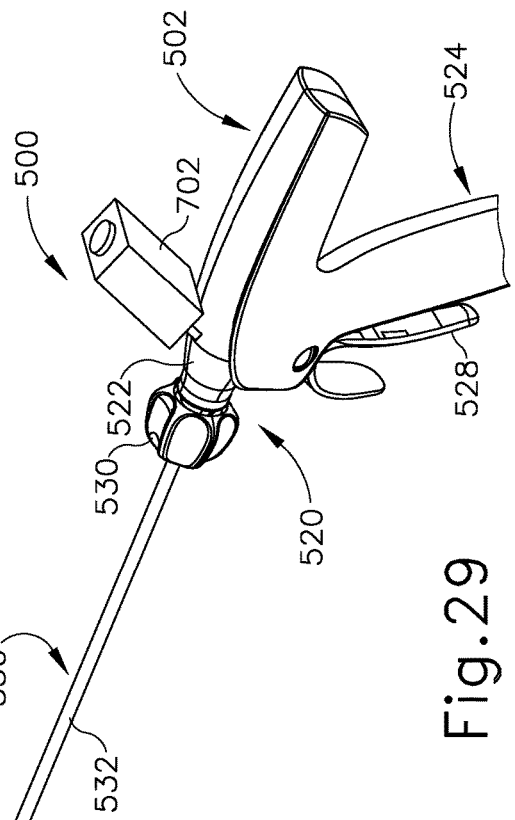
Fig.28
Fig.29

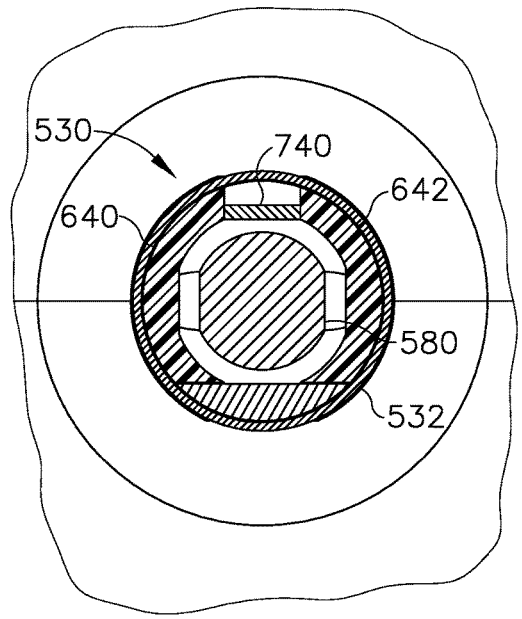 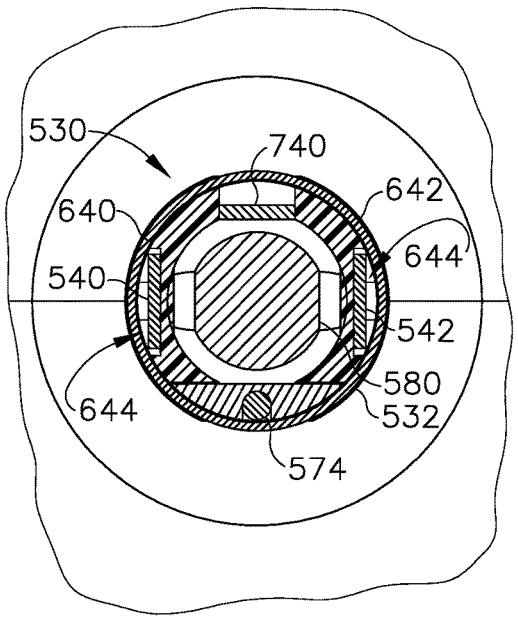
Fig.33    Fig.34
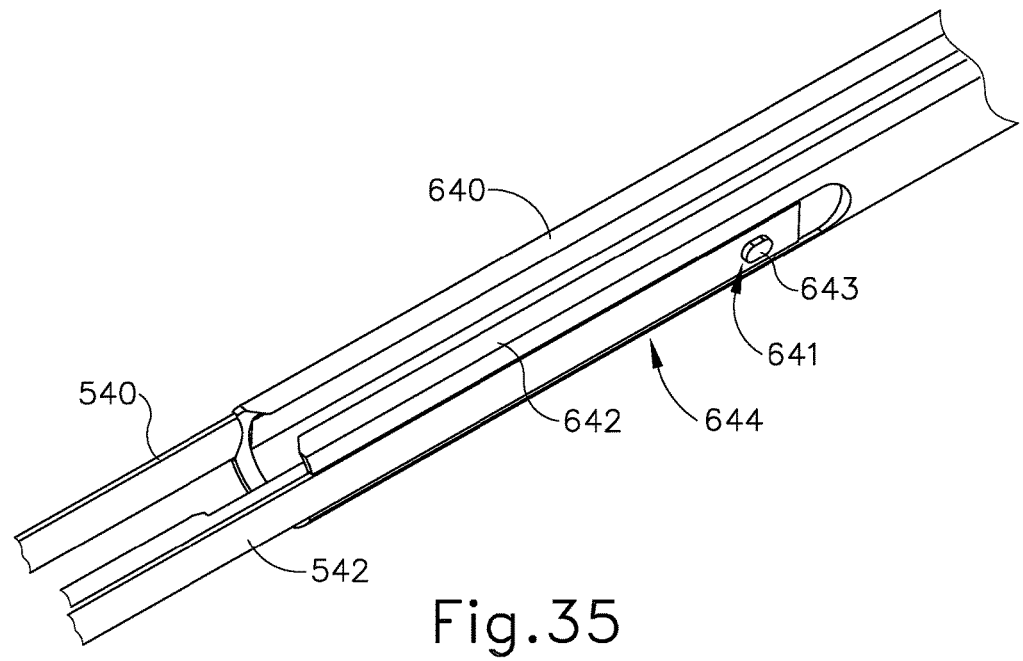
Fig.35

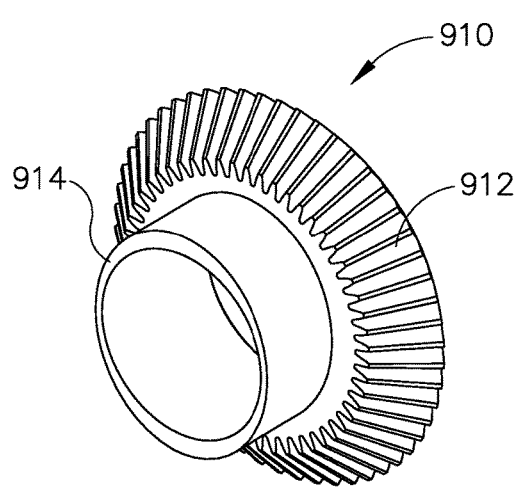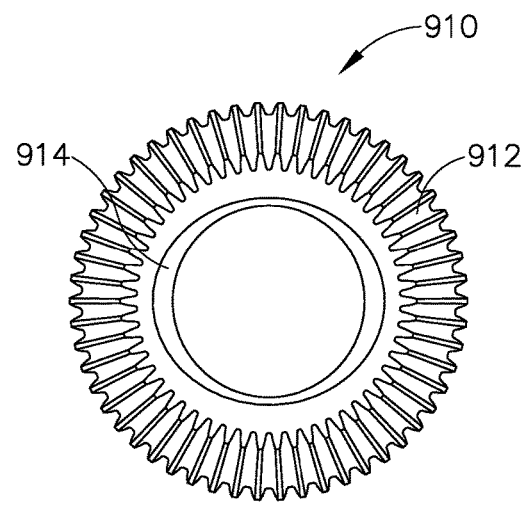
Fig.41D          Fig.41E
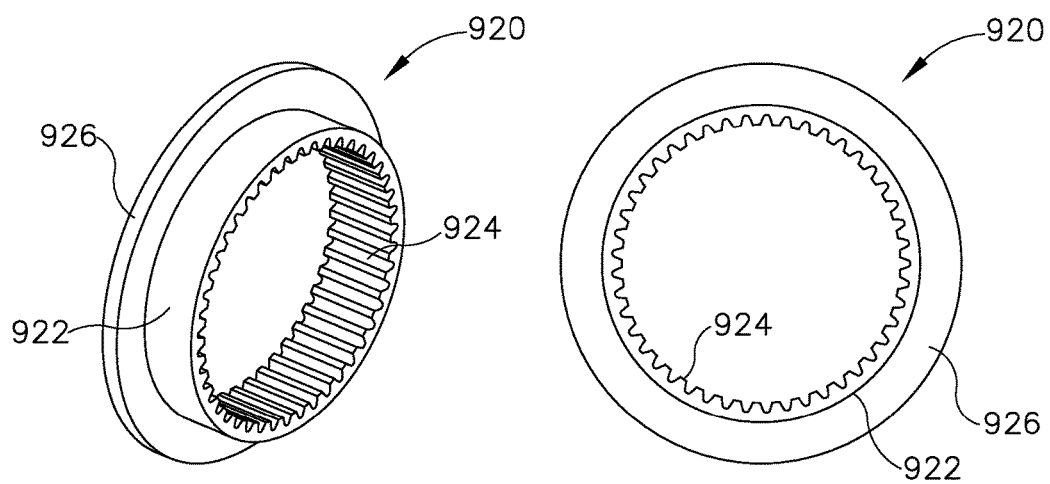
Fig.41F          Fig.41G

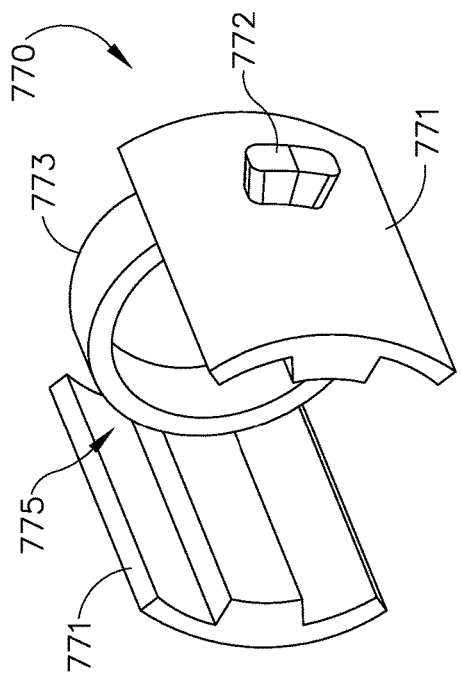
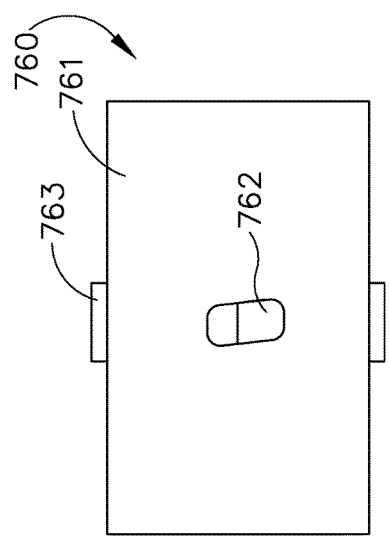
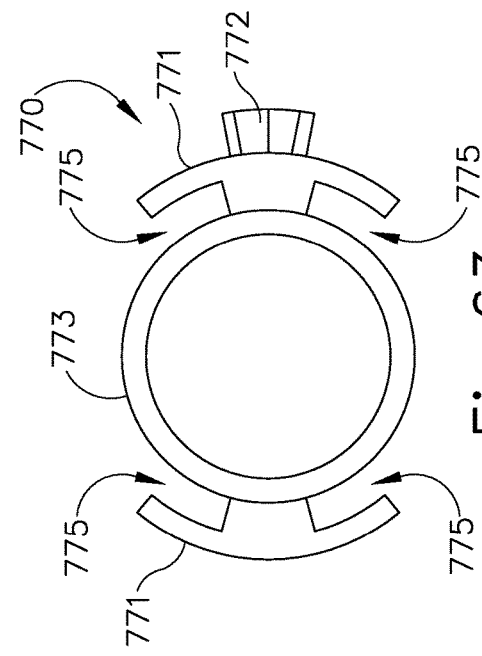
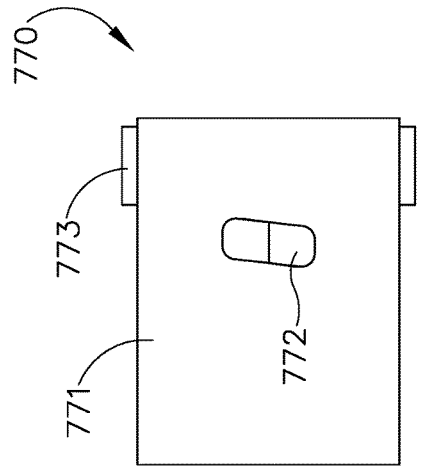
Fig.62
Fig.64
Fig.61
Fig.63

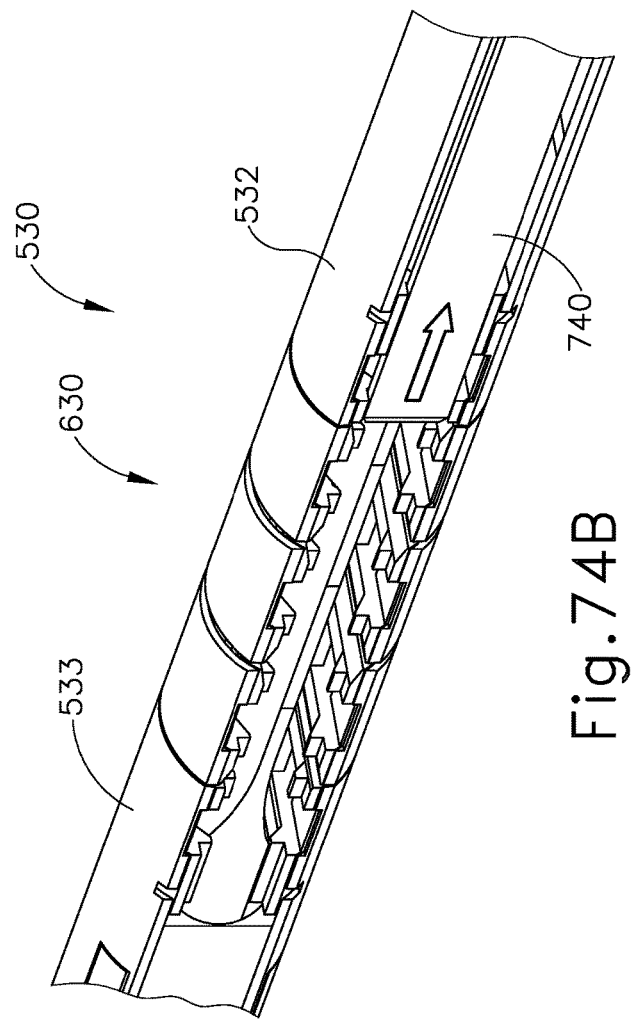
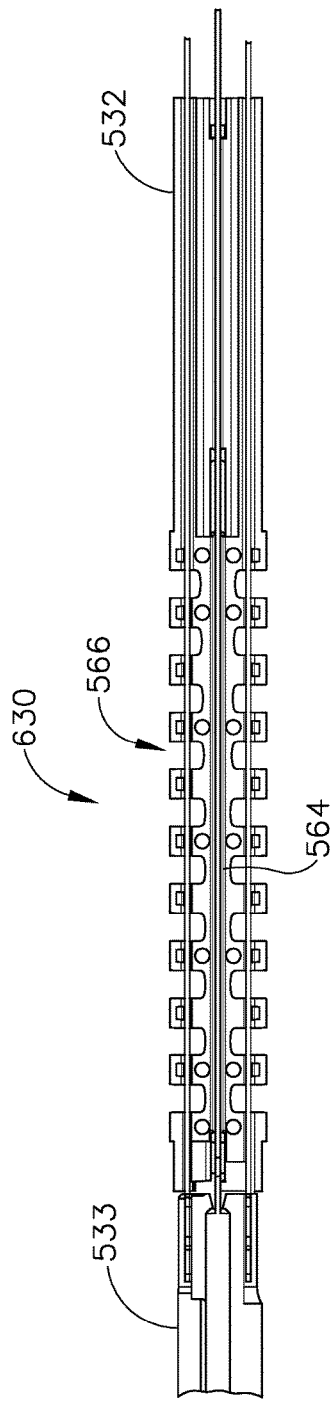

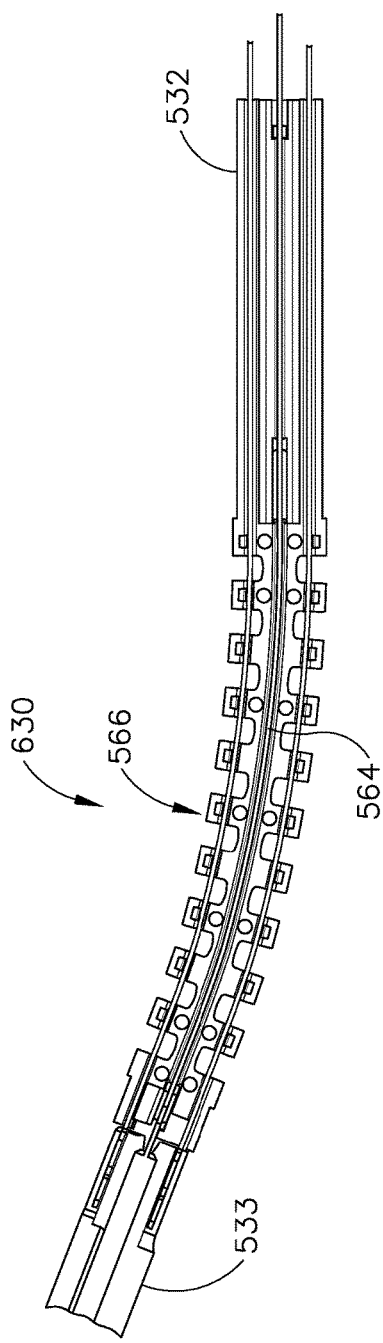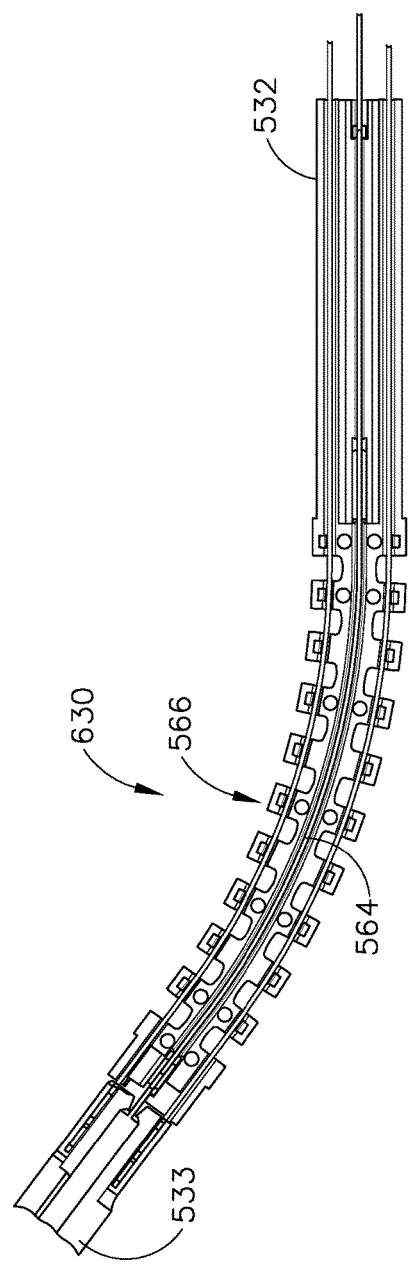

ULTRASONIC SURGICAL INSTRUMENT WITH OPPOSING THREAD DRIVE FOR END EFFECTOR ARTICULATION

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section and/or a bendable ultrasonic waveguide. Examples of such ultrasonic surgical instruments are disclosed in U.S. Pat. No. 5,897,523, entitled "Articulating Ultrasonic Surgical Instrument," issued Apr. 27, 1999, the disclosure of which is incorporated by reference herein; U.S. Pat. No. 5,989,264, entitled "Ultrasonic Polyp Snare," issued Nov. 23, 1999, the disclosure of which is incorporated by reference herein; U.S. Pat. No. 6,063,098, entitled "Articulable Ultrasonic Surgical Apparatus," issued May 16, 2000, the disclosure of which is incorporated by reference herein; U.S. Pat. No. 6,090,120, entitled "Articulating Ultrasonic Surgical Instrument," issued Jul. 18, 2000, the disclosure of which is incorporated by reference herein; U.S. Pat. No. 6,454,782, entitled "Actuation Mechanism for Surgical Instruments," issued Sep. 24, 2002, the disclosure of which is incorporated by reference herein; U.S. Pat. No. 6,589,200, entitled "Articulating Ultrasonic Surgical Shears," issued Jul. 8, 2003, the disclosure of which is incorporated by reference herein; U.S. Pat. No. 6,752,815, entitled "Method and Waveguides for Changing the Direction of Longitudinal Vibrations," issued Jun. 22, 2004, the disclosure of which is incorporated by reference herein; U.S. Pat. No. 7,135,030, entitled "Articulating Ultrasonic Surgical Shears," issued Nov. 14, 2006; U.S. Pat. No. 7,621,930, entitled "Ultrasound Medical Instrument Having a Medical Ultrasonic Blade," issued Nov. 24, 2009, the disclosure of which is incorporated by reference herein; U.S. Pub. No. 2014/0005701, published Jan. 2, 2014, entitled "Surgical Instruments with Articulating Shafts," the disclosure of which is incorporated by reference herein; U.S. Pub. No. 2014/0005703, entitled "Surgical Instruments with Articulating Shafts," published Jan. 2, 2014, issued as U.S. Pat. No. 9,408,622 on Aug. 9, 2016, the disclosure of which is incorporated by reference herein; U.S. Pub. No. 2014/0114334, entitled "Flexible Harmonic Waveguides/Blades for Surgical Instruments," published Apr. 24, 2014, issued as U.S. Pat. No. 9,095,367 on Aug. 4, 2015, the disclosure of which is incorporated by reference herein; U.S. Pub. No. 2015/0080924, entitled ""Articulation Features for Ultrasonic Surgical Instrument," published Mar. 19, 2015, issued as U.S. Pat. No. 10,172,636 on Jan. 8, 2019, the disclosure of which is incorporated by reference herein; and U.S. Pat. App. No. 62/176,880, entitled Ultrasonic Surgical Device with Articulating End Effector," filed Apr. 22, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 20 depicts a perspective view of a lead screw of the drive assembly of FIG. 18;

FIG. 21 depicts a front elevational view of the lead screw of FIG. 20;

FIG. 22 depicts a perspective view of another lead screw of the drive assembly of FIG. 18;

FIG. 23 depicts a front elevational view of the lead screw of FIG. 22;

FIG. 28 depicts a side elevational view of yet another exemplary ultrasonic surgical instrument;

FIG. 29 depicts a perspective view of the instrument of FIG. 28;

FIG. 33 depicts a cross-sectional front view of a shaft assembly of the disposable portion of FIG. 31, taken along line 33-33 of FIG. 31;

FIG. 34 depicts another cross-sectional front view of a shaft assembly of the disposable portion of FIG. 31, taken along line 34-34 of FIG. 31;

FIG. 35 depicts a perspective view of internal components of the shaft assembly of FIG. 34;

FIG. 41D depicts a perspective view of a bevel gear of the gear reduction assembly of FIG. 41B;

FIG. 41E depicts a front elevational view of the bevel gear of FIG. 41D;

FIG. 41F depicts a perspective view of a fixed spline member of the gear reduction assembly of FIG. 41B;

FIG. 41G depicts a rear elevational view of the fixed spline member of FIG. 41F;

FIG. 61 depicts a bottom plan view of the lead screw of FIG. 59;

FIG. 62 depicts a perspective view of yet another lead screw of the drive assembly of FIG. 42;

FIG. 63 depicts a front elevational view of the lead screw of FIG. 62;

FIG. 64 depicts a side elevational view of the lead screw of FIG. 62;

FIG. 74B depicts a cross-sectional perspective view of the shaft assembly of FIG. 34, with the rod member of FIG. 74A moved to a second longitudinal position;

FIG. 75A depicts a cross-sectional top view of the shaft assembly of FIG. 34, with an articulation section of the shaft assembly in a straight configuration;

FIG. 75B depicts a cross-sectional top view of the shaft assembly of FIG. 34, with the articulation section of FIG. 75B moved to a first articulated configuration;

FIG. 75C depicts a cross-sectional top view of the shaft assembly of FIG. 34, with the articulation section of FIG. 75B moved to a second articulated configuration;

Figure 1:
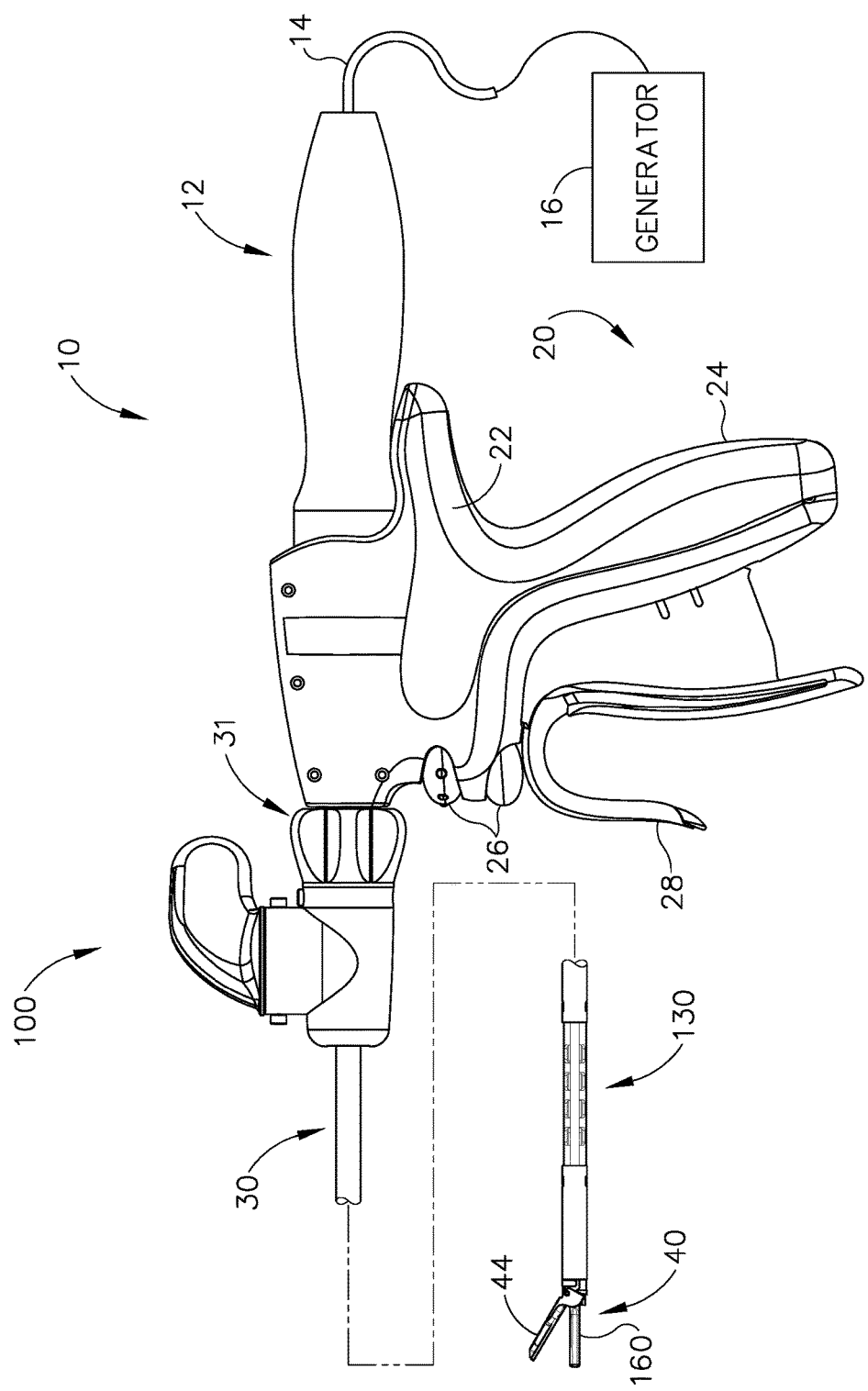
FIG. 1 depicts a side elevational view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIG. 1 shows an exemplary ultrasonic surgical instrument (10). At least part of instrument (10) may be constructed and operable in accordance with at least some of the teachings of any of the various patents, patent application publications, and patent applications that are cited herein. As described therein and as will be described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (10) of the present example comprises a handle assembly (20), a shaft assembly (30), and an end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. End effector (40) includes an ultrasonic blade (160) and a pivoting clamp arm (44). Clamp arm (44) is coupled with trigger (28) such that clamp arm (44) is pivotable toward ultrasonic blade (160) in response to pivoting of trigger (28) toward pistol grip (24); and such that clamp arm (44) is pivotable away from ultrasonic blade (160) in response to pivoting of trigger (28) away from pistol grip (24). Various suitable ways in which clamp arm (44) may be coupled with trigger (28) will be apparent to those of ordinary skill in the art in view of the teachings herein. In some versions, one or more resilient members are used to bias clamp arm (44) and/or trigger (28) to the open position shown in FIG. 1.

An ultrasonic transducer assembly (12) extends proximally from body (22) of handle assembly (20). Transducer assembly (12) is coupled with a generator (16) via a cable (14), such that transducer assembly (12) receives electrical power from generator (16). Piezoelectric elements in transducer assembly (12) convert that electrical power into ultrasonic vibrations. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

A. Exemplary End Effector and Acoustic Drivetrain

Figure 2:
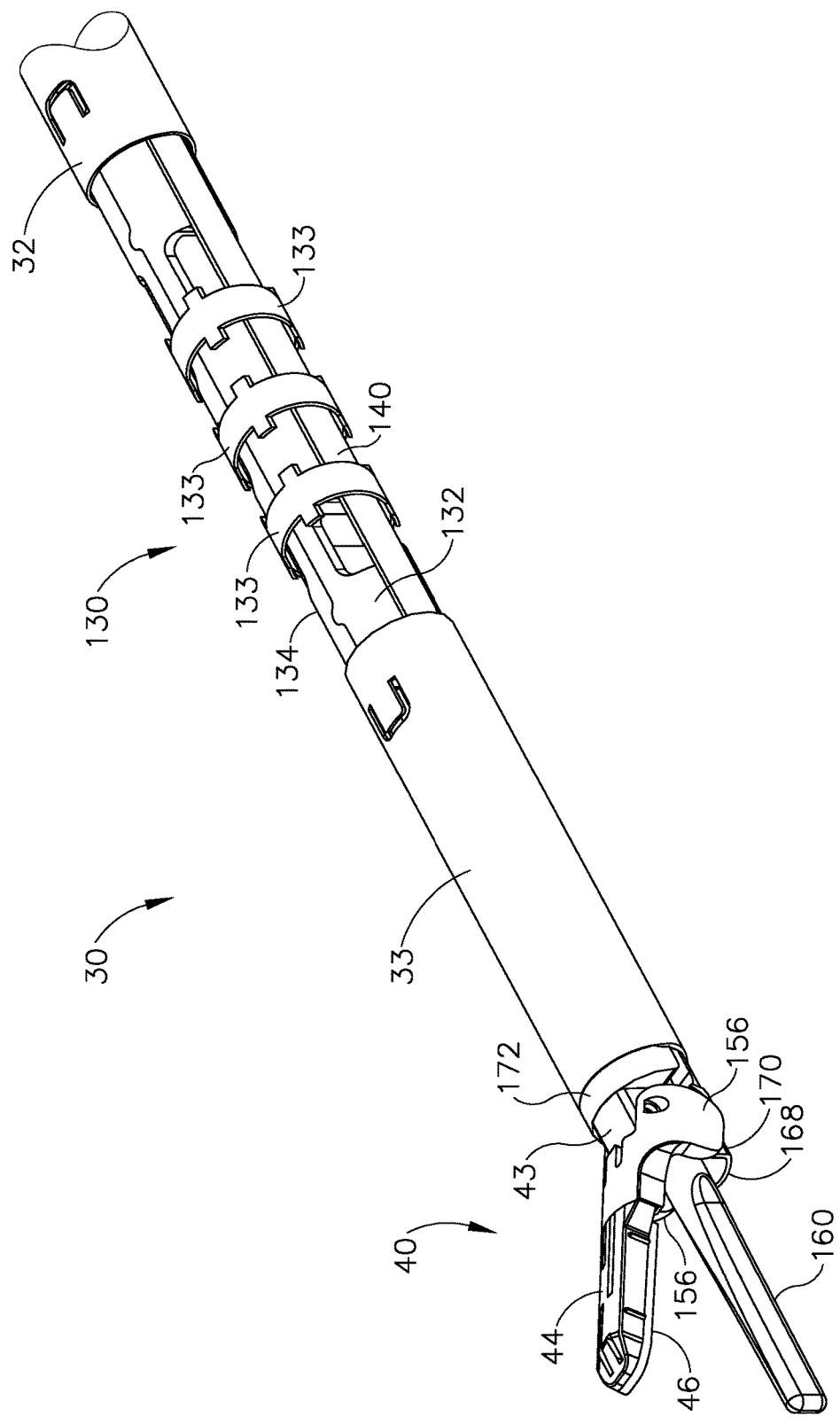
FIG. 2 depicts a perspective view of an articulation section of a shaft assembly and an end effector of the surgical instrument of FIG. 1.
Figure 3:
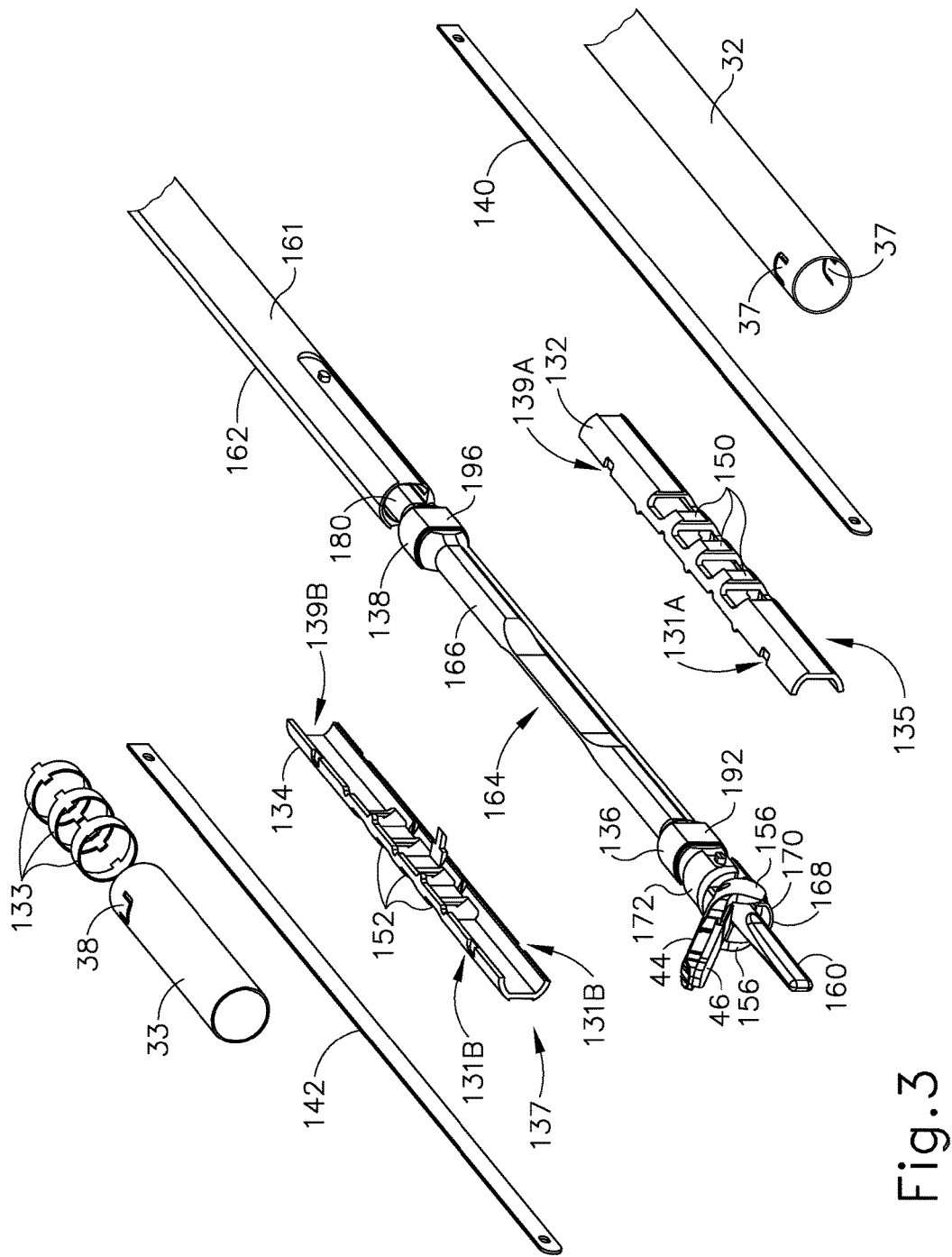
FIG. 3 depicts an exploded perspective view of an articulation section of the shaft assembly of FIG. 2.
Figure 4:
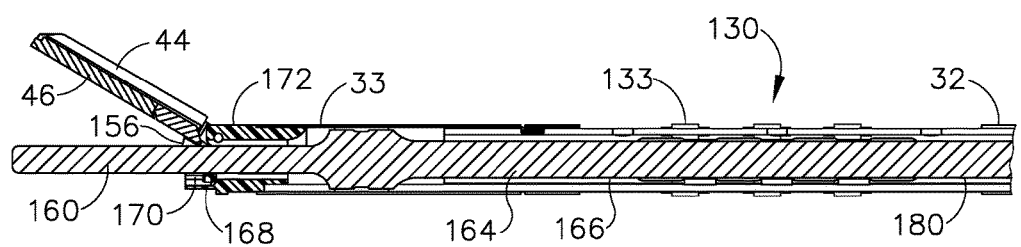
FIG. 4 depicts a cross-sectional side view of the shaft assembly and end effector of FIG. 2.

As best seen in FIGS. 2-4, end effector (40) of the present example comprises clamp arm (44) and ultrasonic blade (160). Clamp arm (44) includes a clamp pad (46) that is secured to the underside of clamp arm (44), facing blade (160). Clamp pad (46) may comprise polytetrafluoroethylene (PTFE) and/or any other suitable material(s). Clamp arm (44) is pivotally secured to a distally projecting tongue (43) of an upper distal shaft element (172), which is fixedly secured within a distal portion of a distal outer sheath (33). Clamp arm (44) is operable to selectively pivot toward and away from blade (160) to selectively clamp tissue between clamp arm (44) and blade (160). A pair of arms (156) extend transversely from clamp arm (44) and are pivotally secured to a lower distal shaft element (170), which is slidably disposed within the distal portion of distal outer sheath (33).

Figure 7:
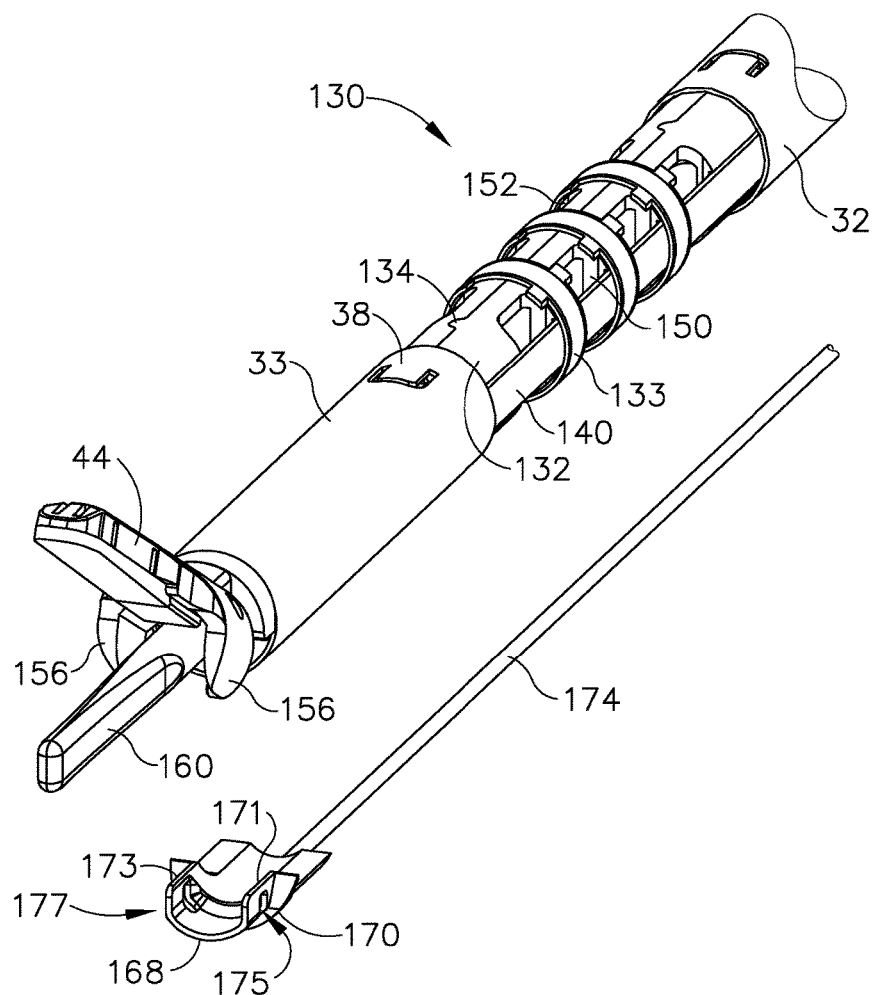
FIG. 7 depicts a partially exploded perspective view of the shaft assembly and end effector of FIG. 2.
Figure 8:
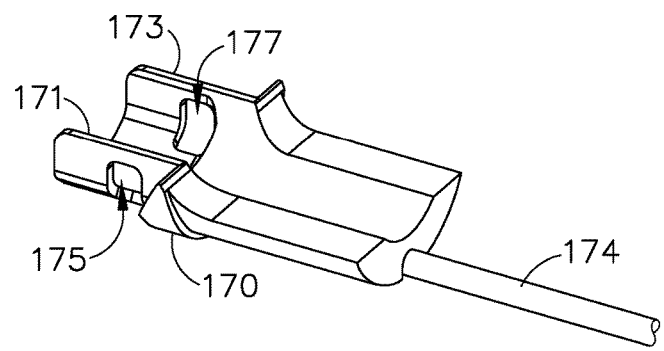
FIG. 8 depicts a perspective view of a distal collar and a drive cable of the shaft assembly of FIG. 2.

As best seen in FIGS. 7-8, a cable (174) is secured to lower distal shaft element (170). Cable (174) is operable to translate longitudinally relative to an articulation section (130) of shaft assembly (30) to selectively pivot clamp arm (44) toward and away from blade (160). In particular, cable (174) is coupled with trigger (28) such that cable (174) translates proximally in response to pivoting of trigger (28) toward pistol grip (24), and such that clamp arm (44) thereby pivots toward blade (160) in response to pivoting of trigger (28) toward pistol grip (24). In addition, cable (174) translates distally in response to pivoting of trigger (28) away from pistol grip (24), such that clamp arm (44) pivots away from blade (160) in response to pivoting of trigger (28) away from pistol grip (24). Clamp arm (44) may be biased toward the open position, such that (at least in some instances) the operator may effectively open clamp arm (44) by releasing a grip on trigger (28).

Figure 10A:
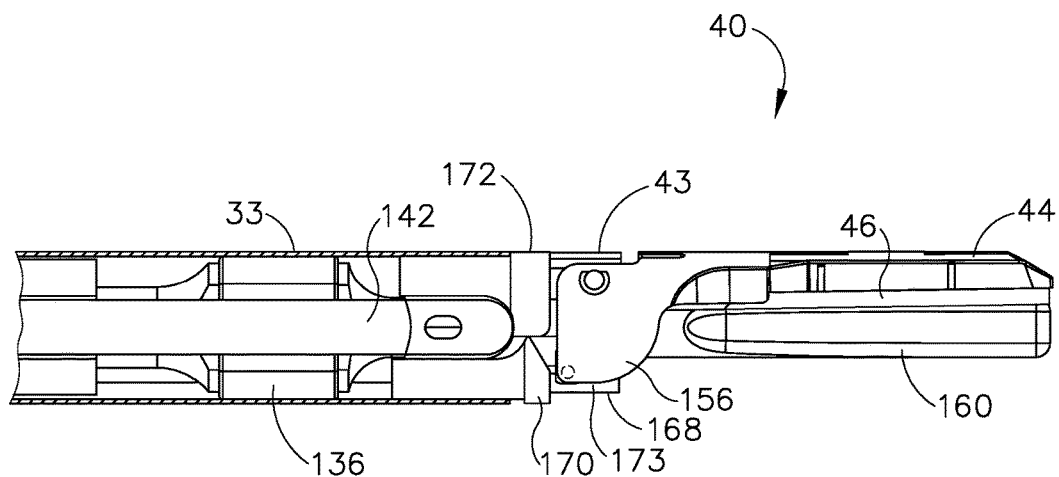
FIG. 10A depicts a side elevational view of an exemplary alternative end effector and the distal portion of a shaft assembly, configured for incorporation in the instrument of FIG. 1, with a clamp arm of the end effector in a closed position, and with an outer sheath shown in cross-section to reveal components within the outer sheath.
Figure 10B:
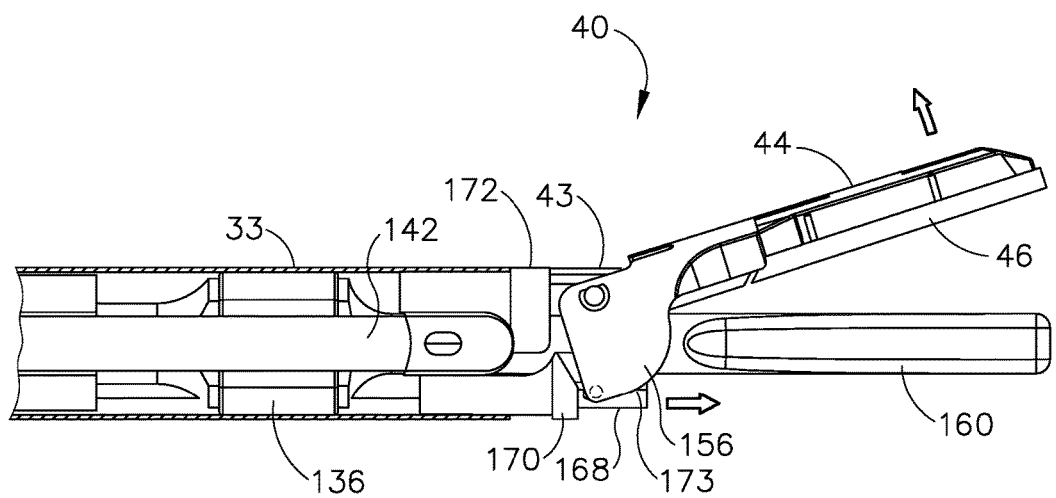
FIG. 10B depicts a side elevational view of the shaft assembly and end effector of FIG. 10A, with the clamp arm moved to a partially open position.
Figure 10C:
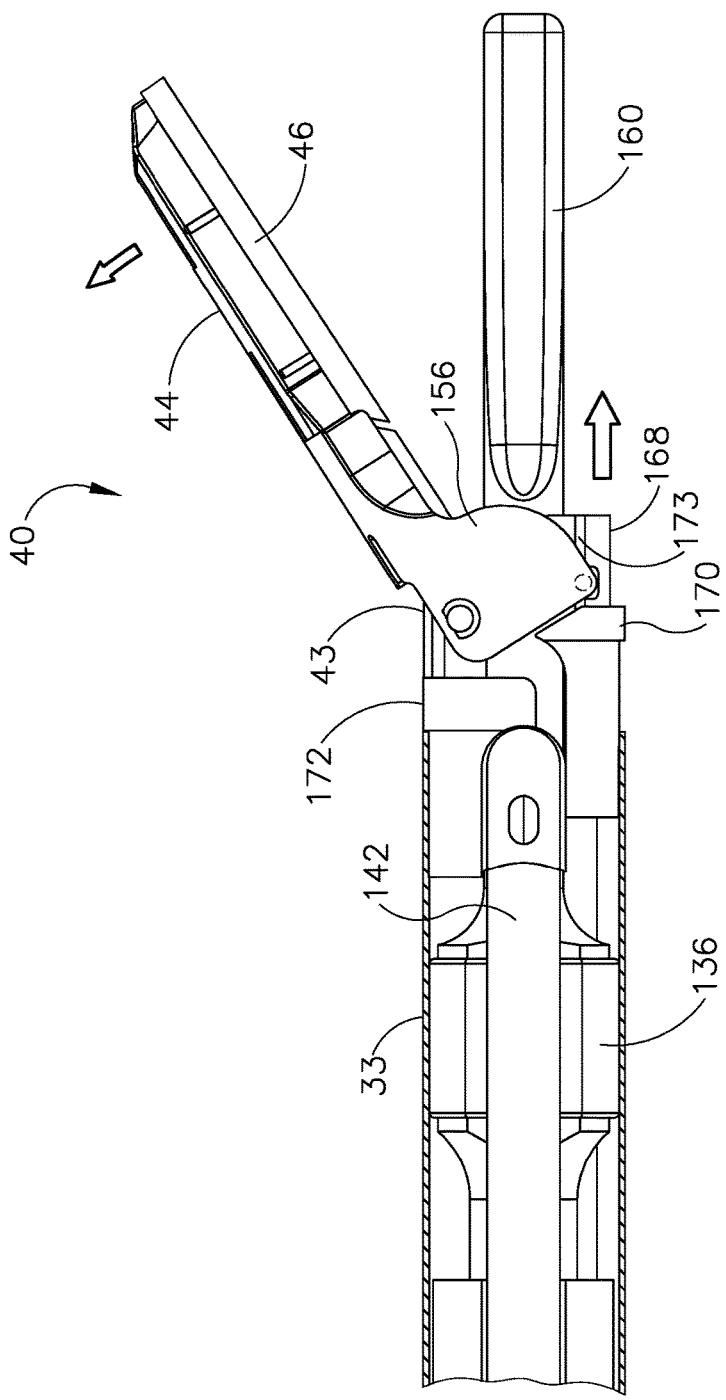
FIG. 10C depicts a side elevational view of the shaft assembly and end effector of FIG. 10A, with the clamp arm moved to a fully open position.

As shown in FIGS. 7-8, cable (174) is secured to a proximal end of lower distal shaft element (170). Lower distal shaft element (170) comprises a pair of distal flanges (171, 173) extending from a semi-circular base (168). Flanges (171, 173) each comprise a respective opening (175, 177). Clamp arm (44) is rotatably coupled to lower distal shaft element (170) via a pair of inwardly extending integral pins (41, 45). Pins (41, 45) extend inwardly from arms (156) of clamp arm (44) and are rotatably disposed within respective openings (175, 177) of lower distal shaft element (170). As shown in FIGS. 10A-10C, longitudinal translation of cable (174) causes longitudinal translation of lower distal shaft element (170) between a proximal position (FIG. 10A) and a distal position (FIG. 10C). Longitudinal translation of lower distal shaft element (170) causes rotation of clamp arm (44) between a closed position (FIG. 10A) and an open position (FIG. 10C).

Blade (160) of the present example is operable to vibrate at ultrasonic frequencies in order to effectively cut through and seal tissue, particularly when the tissue is being compressed between clamp pad (46) and blade (160). Blade (160) is positioned at the distal end of an acoustic drivetrain. This acoustic drivetrain includes transducer assembly (12) and an acoustic waveguide (180). Acoustic waveguide (180) comprises a flexible portion (166). Transducer assembly (12) includes a set of piezoelectric discs (not shown) located proximal to a horn (not shown) of waveguide (180). The piezoelectric discs are operable to convert electrical power into ultrasonic vibrations, which are then transmitted along waveguide (180), including flexible portion (166) of waveguide (180) to blade (160) in accordance with known configurations and techniques. By way of example only, this portion of the acoustic drivetrain may be configured in accordance with various teachings of various references that are cited herein.

As best seen in FIG. 3, flexible portion (166) of waveguide (180) includes a distal flange (136), a proximal flange (138), and a narrowed section (164) located between flanges (136, 138). In the present example, flanges (136, 138) are located at positions corresponding to nodes associated with resonant ultrasonic vibrations communicated through flexible portion (166) of waveguide (180). Narrowed section (164) is configured to allow flexible portion (166) of waveguide (180) to flex without significantly affecting the ability of flexible portion (166) of waveguide (180) to transmit ultrasonic vibrations. By way of example only, narrowed section (164) may be configured in accordance with one or more teachings of U.S. Pub. No. 2014/0005701, issued as U.S. Pat. No. 9,393,037 on Jul. 19, 2016, and/or U.S. Pub. No. 2014/0114334, issued as U.S. Pat. No. 9,095,367 on Aug. 4, 2015, the disclosures of which are incorporated by reference herein. It should be understood that waveguide (180) may be configured to amplify mechanical vibrations transmitted through waveguide (180). Furthermore, waveguide (180) may include features operable to control the gain of the longitudinal vibrations along waveguide (180) and/or features to tune waveguide (180) to the resonant frequency of the system. Various suitable ways in which waveguide (180) may be mechanically and acoustically coupled with transducer assembly (12) will be apparent to those of ordinary skill in the art in view of the teachings herein.

In the present example, the distal end of blade (160) is located at a position corresponding to an anti-node associated with resonant ultrasonic vibrations communicated through flexible portion (166) of waveguide (180), in order to tune the acoustic assembly to a preferred resonant frequency $f_o$ when the acoustic assembly is not loaded by tissue. When transducer assembly (12) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through waveguide (180) to reach blade (160), thereby providing oscillation of blade (160) at the resonant ultrasonic frequency. Thus, when tissue is secured between blade (160) and clamp pad (46), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (44) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, other suitable configurations for end effector (40) will be apparent to those of ordinary skill in the art in view of the teachings herein.

B. Exemplary Shaft Assembly and Articulation Section

Shaft assembly (30) of the present example extends distally from handle assembly (20). As shown in FIGS. 2-7, shaft assembly (30) includes distal outer sheath (33) and a proximal outer sheath (32) that enclose clamp arm (44) drive features and the above-described acoustic transmission features. Shaft assembly (30) further includes an articulation section (130), which is located at a distal portion of shaft assembly (30), with end effector (40) being located distal to articulation section (130). As shown in FIG. 1, a knob (31) is secured to a proximal portion of proximal outer sheath (32). Knob (31) is rotatable relative to body (22), such that shaft assembly (30) is rotatable about the longitudinal axis defined by outer sheath (32), relative to handle assembly (20). Such rotation may provide rotation of end effector (40), articulation section (130), and shaft assembly (30) unitarily. Of course, rotatable features may simply be omitted if desired.

Articulation section (130) is operable to selectively position end effector (40) at various lateral deflection angles relative to a longitudinal axis defined by outer sheath (32). Articulation section (130) may take a variety of forms. By way of example only, articulation section (130) may be configured in accordance with one or more teachings of U.S. Pub. No. 2012/0078247, issued as U.S. Pat. No. 9,402,682 on Aug. 2, 2016, the disclosure of which is incorporated by reference herein. As another merely illustrative example, articulation section (130) may be configured in accordance with one or more teachings of U.S. Pub. No. 2014/0005701, issued as U.S. Pat. No. 9,393,037 on Jul. 19, 2016 and/or U.S. Pub. No. 2014/0114334, issued as U.S. Pat. No. 9,095,367 on Aug. 4, 2015, the disclosures of which are incorporated by reference herein. Various other suitable forms that articulation section (130) may take will be apparent to those of ordinary skill in the art in view of the teachings herein. As yet another merely illustrative example, articulation section (130) may be configured in accordance with one or more teachings of U.S. Pub. No. 2012/0078248, entitled "Articulation Joint Features for Articulating Surgical Device," published Mar. 29, 2012, issued as U.S. Pat. No. 9,220,559 on Dec. 29, 2015, the disclosure of which is incorporated by reference herein.

As best seen in FIGS. 2-6B articulation section (130) of this example comprises a set of three retention collars (133) and a pair of ribbed body portions (132, 134), with a pair of articulation bands (140, 142) extending along respective channels (135, 137) defined between interior surfaces of retention collars (133) and exterior surfaces of ribbed body portions (132, 134). Ribbed body portions (132, 134) are longitudinally positioned between flanges (136, 138) of flexible portion (166) of waveguide (180). In some versions, ribbed body portions (132, 134) snap together about flexible portion (166) of waveguide (180). Ribbed body portions (132, 134) are configured to flex with flexible portion (166) of waveguide (180) when articulation section (130) bends to achieve an articulated state.

FIG. 3 shows ribbed body portions (132, 134) in greater detail. In the present example, ribbed body portions (132, 134) are formed of a flexible plastic material, though it should be understood that any other suitable material may be used. Ribbed body portion (132) comprises a set of three ribs (150) that are configured to promote lateral flexing of ribbed body portion (132). Of course, any other suitable number of ribs (150) may be provided. Ribbed body portion (132) also defines a channel (135) that is configured to receive articulation band (140) while allowing articulation band (140) to slide relative to ribbed body portion (132). Similarly, ribbed body portion (134) comprises a set of three ribs (152) that are configured to promote lateral flexing of ribbed body portion (134). Of course, any other suitable number of ribs (152) may be provided. Ribbed body portion (134) also defines a channel (137) that is configured to receive articulation band (142) while allowing articulation band (142) to slide relative to ribbed body portion (137).

Figure 5:
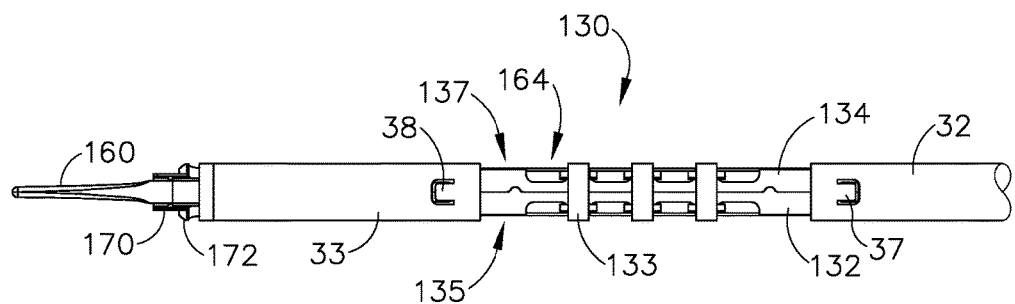
FIG. 5 depicts a top plan view of the shaft assembly and end effector of FIG. 2.

As best seen in FIG. 5, ribbed body portions (132, 134) are laterally interposed between articulation bands (140, 142) and flexible portion (166) of waveguide (180). Ribbed body portions (132, 134) mate with each other such that they together define an internal passage sized to accommodate flexible portion (166) of waveguide (180) without contacting waveguide (180). In addition, when ribbed body portions (132, 134) are coupled together, a pair of complementary distal notches (131A, 131B) formed in ribbed body portions (132, 134) align to receive a pair of inwardly projecting resilient tabs (38) of distal outer sheath (33). This engagement between tabs (38) and notches (131A, 131B) longitudinally secures ribbed body portions (132, 134) relative to distal outer sheath (33). Similarly, when ribbed body portions (132, 134) are coupled together, a pair of complementary proximal notches (139A, 139B) formed in ribbed body portions (132, 134) align to receive a pair of inwardly projecting resilient tabs (37) of proximal outer sheath (32). This engagement between tabs (37) and notches (139A, 139B) longitudinally secures ribbed body portions (132, 134) relative to proximal outer sheath (32). Of course, any other suitable kinds of features may be used to couple ribbed body portions (132, 134) with proximal outer sheath (32) and/or distal outer sheath (33).

Figure 6A:
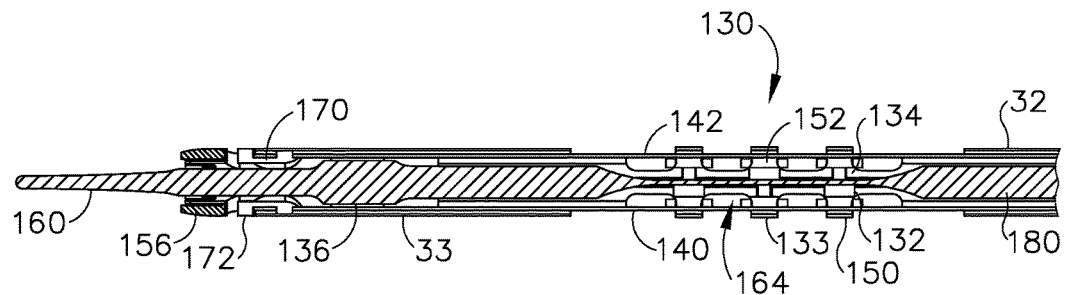
FIG. 6A depicts a cross-sectional top view of the shaft assembly and end effector of FIG. 2 in a straight configuration.
Figure 6B:
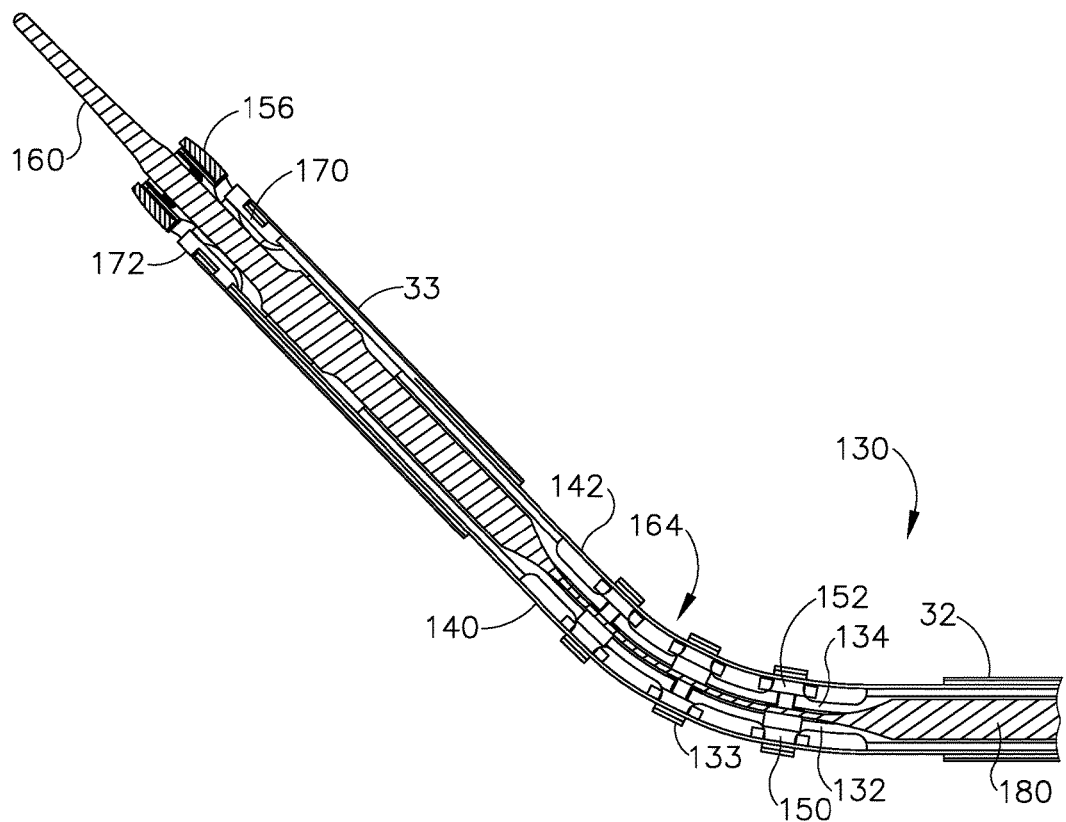
FIG. 6B depicts a cross-sectional top view of the shaft assembly and end effector of FIG. 2 in an articulated configuration.

The distal ends of articulation bands (140, 142) are unitarily secured to upper distal shaft element (172). When articulation bands (140, 142) translate longitudinally in an opposing fashion, this will cause articulation section (130) to bend, thereby laterally deflecting end effector (40) away from the longitudinal axis of shaft assembly (30) from a straight configuration as shown in FIG. 6A to an articulated configuration as shown in FIG. 6B. In particular, end effector (40) will be articulated toward the articulation band (140, 142) that is being pulled proximally. During such articulation, the other articulation band (140, 142) may be pulled distally by upper distal shaft element (172). Alternatively, the other articulation band (140, 142) may be driven distally by an articulation control. Ribbed body portions (132, 134) and narrowed section (164) are all sufficiently flexible to accommodate the above-described articulation of end effector (40). Furthermore, flexible acoustic waveguide (166) is configured to effectively communicate ultrasonic vibrations from waveguide (180) to blade (160) even when articulation section (130) is in an articulated state as shown in FIG. 6B.

As best seen in FIG. 3, each flange (136, 138) of waveguide (180) includes a respective pair of opposing flats (192, 196). Flats (192, 196) are oriented along vertical planes that are parallel to a vertical plane extending through narrowed section (164) of flexible portion (166). Flats (192, 196) are configured to provide clearance for articulation bands (140, 142). In particular, flats (196) of proximal flange (138) accommodate articulation bands (140, 142) between proximal flange (138) and the inner diameter of proximal outer sheath (32): while flats (192) of distal flange (136) accommodate articulation bands (140, 142) between distal flange (136) and the inner diameter of distal outer sheath (33). Of course, flats (192, 196) could be substituted with a variety of features, including but not limited to slots, channels, etc., with any suitable kind of profile (e.g., square, flat, round, etc.). In the present example, flats (192, 196) are formed in a milling process, though it should be understood that any other suitable process(es) may be used. Various suitable alternative configurations and methods of forming flats (192, 196) will be apparent to those of ordinary skill in the art in view of the teachings herein. It should also be understood that waveguide (180) may include flats formed in accordance with at least some of the teachings of U.S. Pub. No. 2013/0289592, entitled "Ultrasonic Device for Cutting and Coagulating," filed Apr. 23, 2013, issued as U.S. Pat. No. 10,238,416 on Mar. 16, 2019, the disclosure of which is incorporated by reference herein.

In the present example, outer rings (133) are located at longitudinal positions corresponding to ribs (150, 152), such that three rings (133) are provided for three ribs (150, 152). Articulation band (140) is laterally interposed within channel (135) between rings (133) and ribbed body portion (132); while articulation band (142) is laterally interposed within channel (137) between rings (133) and ribbed body portion (134). Rings (133) are configured to keep articulation bands (140, 142) in a parallel relationship, particularly when articulation section (130) is in a bent configuration (e.g., similar to the configuration shown in FIG. 6B). In other words, when articulation band (140) is on the inner diameter of a curved configuration presented by a bent articulation section (130), rings (133) may retain articulation band (140) such that articulation band (140) follows a curved path that complements the curved path followed by articulation band (142). It should be understood that channels (135, 137) are sized to accommodate respective articulation bands (140, 142) in such a way that articulation bands (140, 142) may still freely slide through articulation section (130), even with rings (133) being secured to ribbed body portions (150, 152). It should also be understood that rings (133) may be secured to ribbed body portions (132, 134) in various ways, including but not limited to interference fitting, adhesives, welding, etc.

When articulation bands (140, 142) are translated longitudinally in an opposing fashion, a moment is created and applied to a distal end of distal outer sheath (33) via upper distal shaft element (172). This causes articulation section (130) and narrowed section (164) of flexible portion (166) of waveguide (180) to articulate, without transferring axial forces in articulation bands (140, 142) to waveguide (180). It should be understood that one articulation band (140, 142) may be actively driven distally while the other articulation band (140, 142) is passively permitted to retract proximally. As another merely illustrative example, one articulation band (140, 142) may be actively driven proximally while the other articulation band (140, 142) is passively permitted to advance distally. As yet another merely illustrative example, one articulation band (140, 142) may be actively driven distally while the other articulation band (140, 142) is actively driven proximally. Various suitable ways in which articulation bands (140, 142) may be driven will be apparent to those of ordinary skill in the art in view of the teachings herein.

Figure 9:
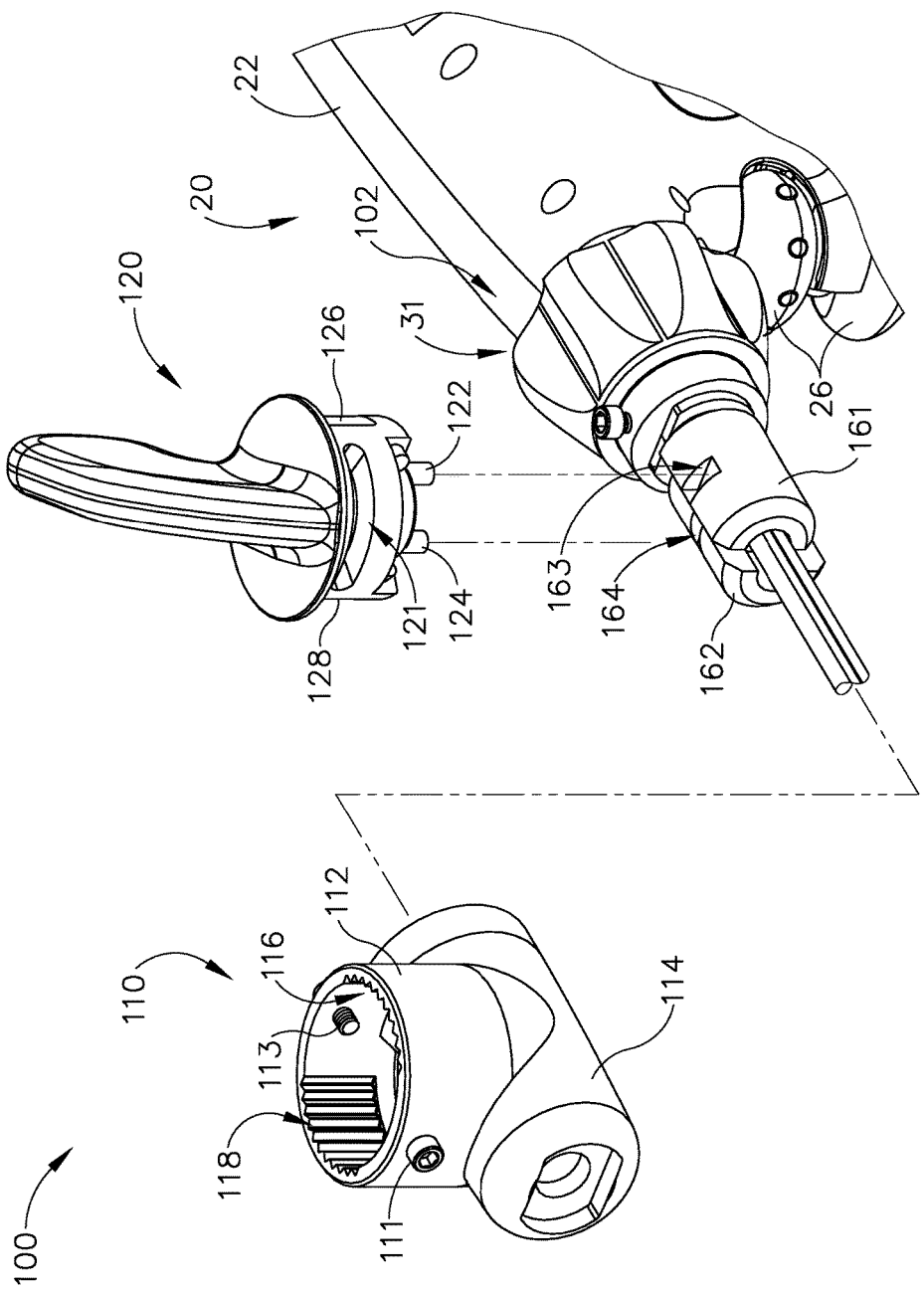
FIG. 9 depicts a partially exploded perspective view of an articulation control assembly of the instrument of FIG. 1.

As best seen in FIG. 9, an articulation control assembly (100) is secured to a proximal portion of outer sheath (32). Articulation control assembly (100) comprises a housing (110) and a rotatable knob (120). Housing (110) comprises a pair of perpendicularly intersecting cylindrical portions (112, 114). Knob (120) is rotatably disposed within a first hollow cylindrical portion (112) of housing (110) such that knob (120) is operable to rotate within cylindrical portion (112) of housing (110). Shaft assembly (30) is slidably and rotatably disposed within a second cylindrical portion (114). Shaft assembly (30) comprises a pair of translatable members (161, 162), both of which extend slidably and longitudinally through the proximal portion of outer sheath (32). Translatable members (161, 162) are longitudinally translatable within second cylindrical portion (114) between a distal position and a proximal position. Translatable members (161, 162) are mechanically coupled with respective articulation bands (140, 142) such that longitudinal translation of translatable member (161) causes longitudinal translation of articulation band (140), and such that longitudinal translation of translatable member (162) causes longitudinal translation of articulation band (142).

Knob (120) comprises a pair of pins (122, 124) extending downwardly from a bottom surface of knob (120). Pins (122, 124) extend into second cylindrical portion (114) of housing (110) and are rotatably and slidably disposed within a respective pair of channels (163, 164) formed in top surfaces of translatable members (161, 162). Channels (163, 164) are positioned on opposite sides of an axis of rotation of knob (120), such that rotation of knob (120) about that axis causes opposing longitudinal translation of translatable members (161, 162). For instance, rotation of knob (120) in a first direction causes distal longitudinal translation of translatable member (161) and articulation band (140), and proximal longitudinal translation of translatable member (162) and articulation band (142); and rotation of knob (120) in a second direction causes proximal longitudinal translation of translatable member (161) and articulation band (140), and distal longitudinal translation of translatable member (162) and articulation band (142). Thus, it should be understood that rotation of rotation knob (120) causes articulation of articulation section (130).

Housing (110) of articulation control assembly (100) comprises a pair of set screws (111, 113) extending inwardly from an interior surface of first cylindrical portion (112). With knob (120) rotatably disposed within first cylindrical portion (112) of housing (110), set screws (111, 113) are slidably disposed within a pair of arcuate channels (121, 123) formed in knob (120). Thus, it should be understood that rotation of knob (120) will be limited by movement of set screws (111, 113) within channels (121, 123). Set screws (111, 113) also retain knob (120) in housing (110), preventing knob (120) from traveling vertically within first cylindrical portion (112) of housing (110).

An interior surface of first cylindrical portion (112) of housing (110) comprises a first angular array of teeth (116) and a second angular array of teeth (118) formed in an interior surface of first cylindrical portion (112). Rotation knob (120) comprises a pair of outwardly extending engagement members (126, 128) that are configured to engage teeth (116, 118) of first cylindrical portion (112) in a detent relationship to thereby selectively lock knob (120) in a particular rotational position. The engagement of engagement members (126, 128) with teeth (116, 118) may be overcome by an operator applying sufficient rotational force to knob (120); but absent such force, the engagement will suffice to maintain the straight or articulated configuration of articulation section (130). It should therefore be understood that the ability to selectively lock knob (120) in a particular rotational position lock will enable an operator to selectively lock articulation section (130) in a particular deflected position relative to the longitudinal axis defined by outer sheath (32).

In some versions of instrument (10), articulation section (130) of shaft assembly (30) is operable to achieve articulation angles up to between approximately 15° and approximately 30°, both relative to the longitudinal axis of shaft assembly (30) when shaft assembly (30) is in a straight (non-articulated) configuration. Alternatively, articulation section (130) may be operable to achieve any other suitable articulation angles.

In some versions of instrument (10), narrowed section (164) of waveguide (180) has a thickness between approximately 0.01 inches and approximately 0.02 inches. Alternatively, narrowed section (164) may have any other suitable thickness. Also in some versions, narrowed section (164) has a length of between approximately 0.4 inches and approximately 0.65 inches. Alternatively, narrowed section (164) may have any other suitable length. It should also be understood that the transition regions of waveguide (180) leading into and out of narrowed section (164) may be quarter rounded, tapered, or have any other suitable configuration.

In some versions of instrument (10), flanges (136, 138) each have a length between approximately 0.1 inches and approximately 0.2 inches. Alternatively, flanges (136, 138) may have any other suitable length. It should also be understood that the length of flange (136) may differ from the length of flange (138). Also in some versions, flanges (136, 138) each have a diameter between approximately 0.175 inches and approximately 0.2 inches. Alternatively, flanges (136, 138) may have any other suitable outer diameter. It should also be understood that the outer diameter of flange (136) may differ from the outer diameter of flange (138).

While the foregoing exemplary dimensions are provided in the context of instrument (10) as described above, it should be understood that the same dimensions may be used in any of the other examples described herein. It should also be understood that the foregoing exemplary dimensions are merely optional. Any other suitable dimensions may be used.

II. Exemplary Alternative Articulation Control Configurations with Perpendicular Rotary Knob When an operator wishes to control articulation of articulation section (130) in instrument (10) as described above, the operator may need to use both hands. In particular, the operator may need to grasp pistol grip (24) with one hand and grasp knob (120) with the other hand, holding handle assembly (20) stationary via pistol grip (24) while the operator rotates knob (120). It may be desirable to provide control of articulation section (130) without requiring the operator to use both hands. This may enable the operator to have a free hand to grasp other instruments or otherwise use as they see fit. An exemplary alternative instrument (200) is described below in which an operator may firmly grasp instrument (200) and control articulation of an articulation section (330) using just one single hand. Various suitable ways in which the below teachings may be modified will be apparent to those of ordinary skill in the art in view of the teachings herein.

A. Overview

FIGS. 11-27C depict an exemplary electrosurgical instrument (200) that includes a handle assembly (220), a shaft assembly (230) extending distally from handle assembly (220), and an end effector (240) disposed at a distal end of shaft assembly (230). Handle assembly (220) of the present example comprises a body (222) including a pistol grip (224) and a button (226). Handle assembly (220) also includes a trigger (228) that is pivotable toward and away from pistol grip (224) to selectively actuate end effector (240) as described above and as described in one or more of the references cited herein. It should be understood, however, that various other suitable configurations may be used, including but not limited to a scissor grip configuration. End effector (240) includes an ultrasonic blade (260) and a pivoting clamp arm (244). Clamp arm (244) is coupled with trigger (228) such that clamp arm (244) is pivotable toward ultrasonic blade (260) in response to pivoting of trigger (228) toward pistol grip (224); and such that clamp arm (244) is pivotable away from ultrasonic blade (260) in response to pivoting of trigger (228) away from pistol grip (224). Various suitable ways in which clamp arm (244) may be coupled with trigger (228) will be apparent to those of ordinary skill in the art in view of the teachings herein. In some versions, one or more resilient members are used to bias clamp arm (244) and/or trigger (228) to the open position shown in FIGS. 11 and 12.

An ultrasonic transducer assembly (212) extends proximally from body (222) of handle assembly (220). Transducer assembly (212) is coupled with a generator (216) via a cable (214), such that transducer assembly (212) receives electrical power from generator (216). Piezoelectric elements in transducer assembly (212) convert that electrical power into ultrasonic vibrations. Generator (216) may include a power source and control module that is configured to provide a power profile to transducer assembly (212) that is particularly suited for the generation of ultrasonic vibrations through transducer assembly (212). By way of example only, generator (216) may comprise a GEN 300 sold by Ethicon Endo-Surgery, Inc. of Cincinnati, Ohio. In addition or in the alternative, generator (216) may be constructed in accordance with at least some of the teachings of U.S. Pub. No. 2011/0087212, issued as U.S. Pat. No. 8,986, 302 on Mar. 24, 2015, entitled "Surgical Generator for Ultrasonic and Electrosurgical Devices," published Apr. 14, 2011, the disclosure of which is incorporated by reference herein. It should also be understood that at least some of the functionality of generator (216) may be integrated into handle assembly (220), and that handle assembly (220) may even include a battery or other on-board power source such that cable (214) is omitted. Still other suitable forms that generator (216) may take, as well as various features and operabilities that generator (216) may provide, will be apparent to those of ordinary skill in the art in view of the teachings herein.

An operator may activate button (226) to selectively activate transducer assembly (212) to thereby activate ultrasonic blade (260). In the present example, a single button (226) is provided. Button (226) may be depressed to activate ultrasonic blade (260) at a low power and to activate ultrasonic blade (260) at a high power. For instance, button (226) may be pressed through a first range of motion to activate ultrasonic blade (260) at a low power; and through a second range of motion to activate ultrasonic blade (260) at a high power. Of course, any other suitable number of buttons and/or otherwise selectable power levels may be provided. For instance, a foot pedal may be provided to selectively activate transducer assembly (212). Button (226) of the present example is positioned such that an operator may readily fully operate instrument (200) with a single hand. For instance, the operator may position their thumb about pistol grip (224), position their middle, ring, and/or little finger about trigger (228), and manipulate button (226) using their index finger. Alternatively, any other suitable techniques may be used to grip and operate instrument (200); and button (226) may be located at any other suitable positions.

In some versions, button (226) also serves as a mechanical lockout against trigger (224), such that trigger (224) cannot be fully actuated unless button (226) is being pressed simultaneously. Examples of how such a lockout may be provided are disclosed in one or more of the references cited herein. It should be understood that pistol grip (222), trigger (224), and button (226) may be modified, substituted, supplemented, etc. in any suitable way, and that the descriptions of such components herein are merely illustrative.

B. Exemplary End Effector and Acoustic Drivetrain

Figure 11:
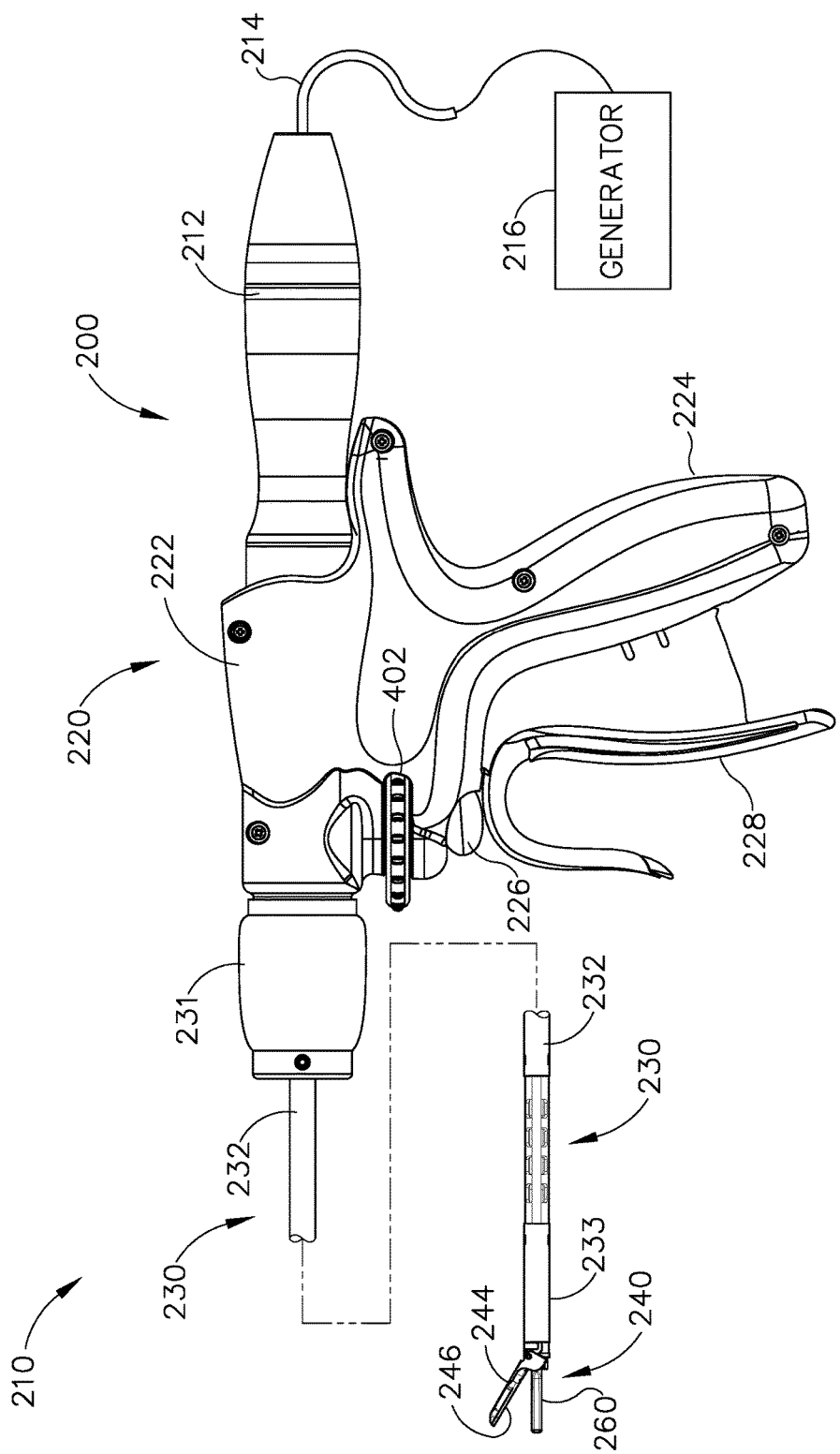
FIG. 11 depicts a side elevational view of another exemplary ultrasonic surgical instrument.
Figure 12:
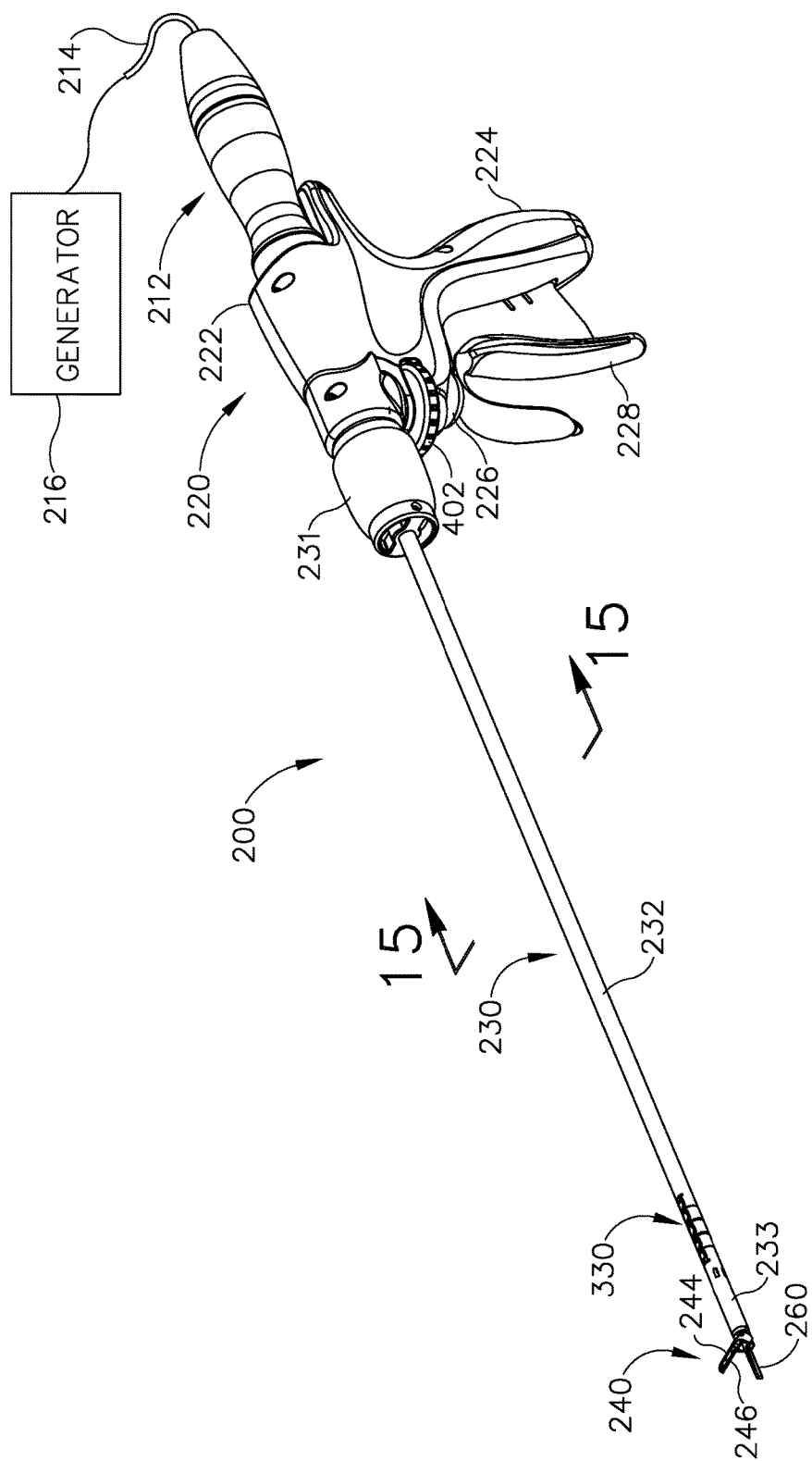
FIG. 12 depicts a perspective view of the instrument of FIG. 11.
Figure 13:
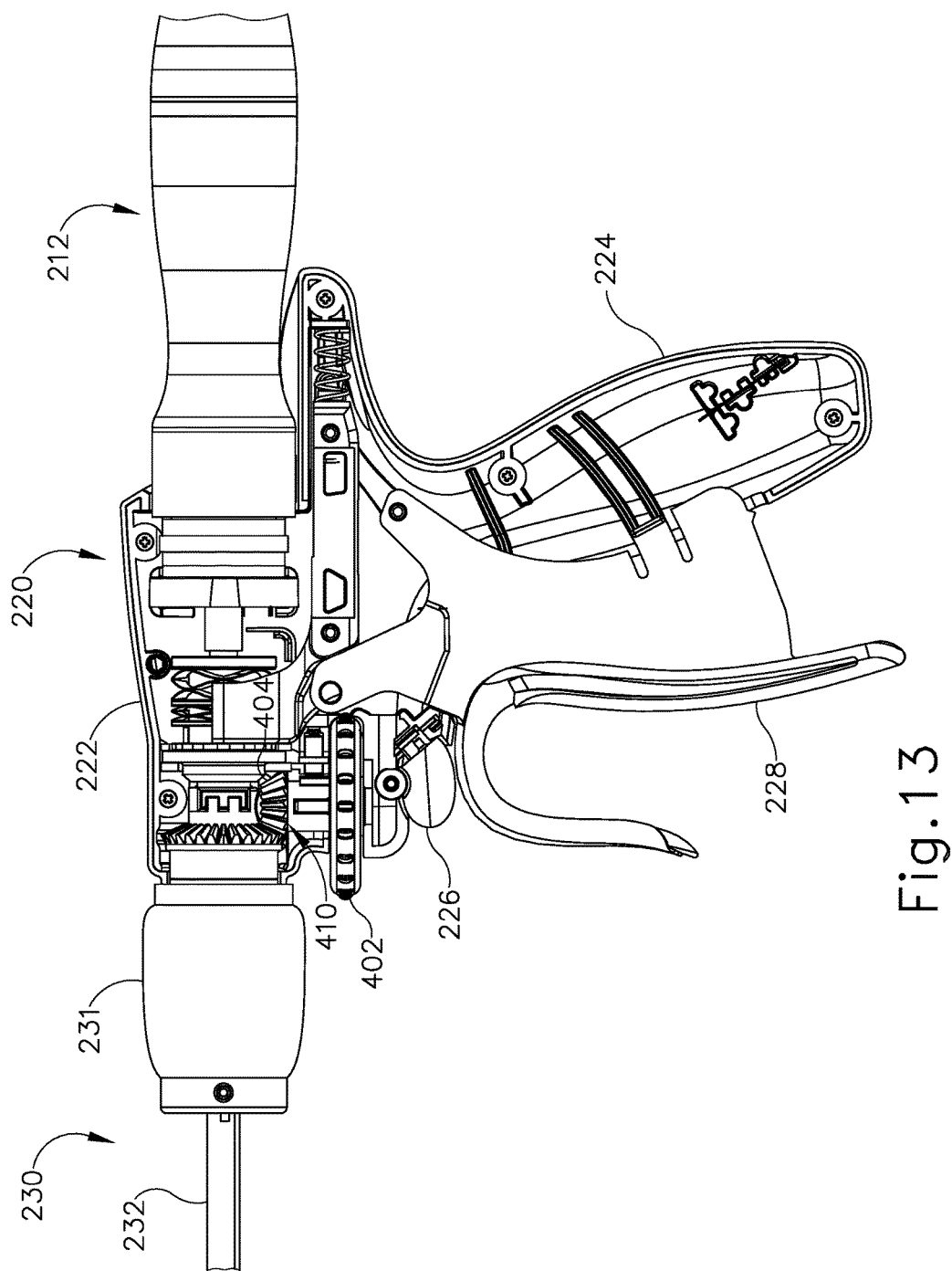
FIG. 13 depicts a side elevational view of a proximal portion of the instrument of FIG. 11 with a shrouding half removed.

As best seen in FIGS. 11 and 12, end effector (240) of the present example comprises clamp arm (244) and ultrasonic blade (260). Clamp arm (244) includes a clamp pad (246) that is secured to the underside of clamp arm (244), facing ultrasonic blade (260). Clamp pad (246) may comprise PTFE and/or any other suitable material(s). Clamp arm (244) is operable to selectively pivot toward and away from ultrasonic blade (260) to selectively clamp tissue between clamp arm (244) and blade (260).

Figure 15:
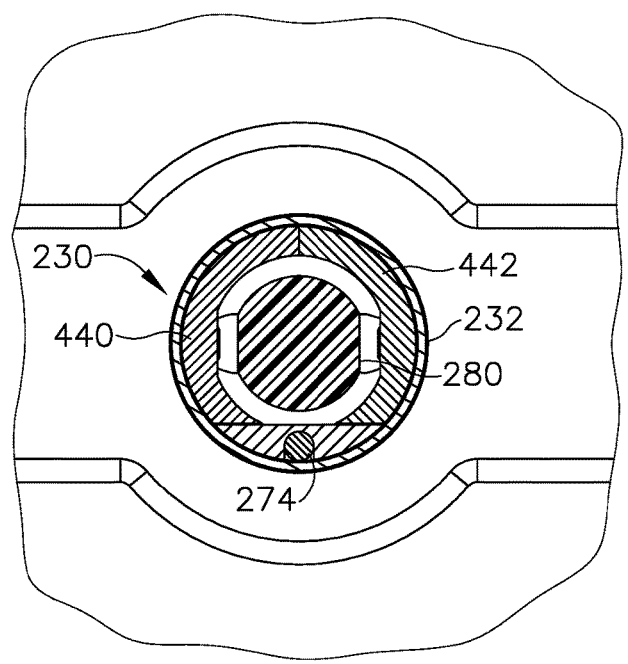
FIG. 15 depicts a cross-sectional front view of a shaft assembly of the instrument of FIG. 11.
Figure 16:
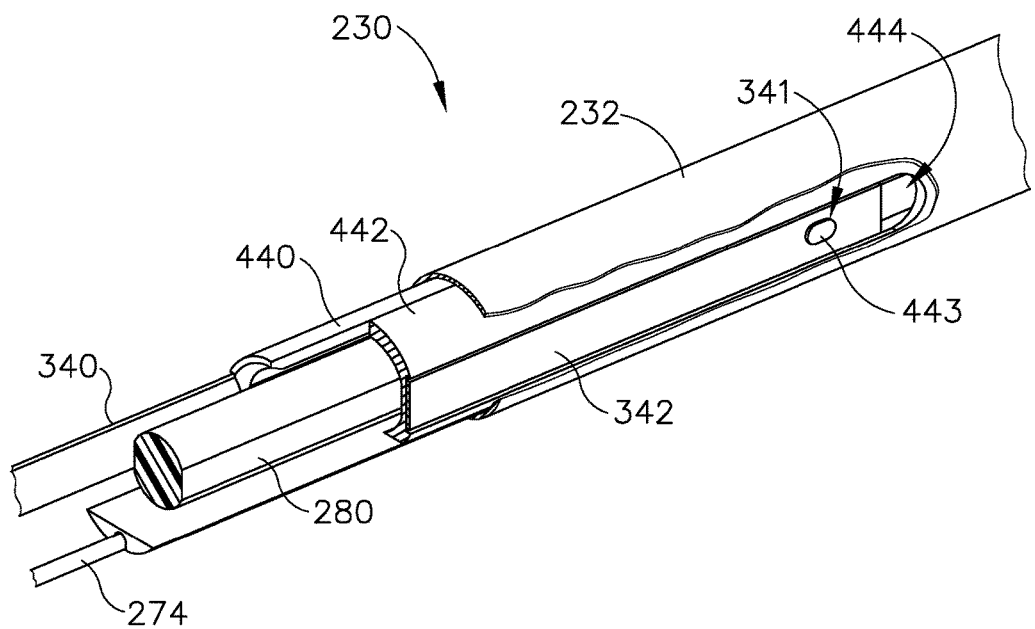
FIG. 16 depicts a perspective view of internal components of the shaft assembly of FIG. 15.

As with clamp arm (44) discussed above, clamp arm (244) of the present example is pivotally secured to a cable (274). Cable (274) is slidably disposed within an outer sheath (232) of shaft assembly (230) as shown in FIGS. 15-16. Cable (274) is operable to translate longitudinally relative to an articulation section (330) of shaft assembly (230) to selectively pivot clamp arm (244) toward and away from blade (260). In particular, cable (274) is coupled with trigger (228) such that cable (274) translates proximally in response to pivoting of trigger (228) toward pistol grip (224), and such that clamp arm (244) thereby pivots toward blade (260) in response to pivoting of trigger (228) toward pistol grip (224). In addition, cable (274) translates distally in response to pivoting of trigger (228) away from pistol grip (224), such that clamp arm (244) pivots away from blade (260) in response to pivoting of trigger (228) away from pistol grip (224). Clamp arm (244) may be biased toward the open position, such that (at least in some instances) the operator may effectively open clamp arm (244) by releasing a grip on trigger (228). It should be understood that clamp arm (244) is merely optional, such that clamp arm (244) may be omitted if desired.

Blade (260) of the present example is operable to vibrate at ultrasonic frequencies in order to effectively cut through and seal tissue, particularly when the tissue is being compressed between clamp pad (246) and blade (260). Blade (260) is positioned at the distal end of an acoustic drivetrain. This acoustic drivetrain includes transducer assembly (212) and an acoustic waveguide (280). Acoustic waveguide (280) comprises a flexible portion (266). Transducer assembly (212) includes a set of piezoelectric discs (not shown) located proximal to a horn (not shown) of waveguide (280). The piezoelectric discs are operable to convert electrical power into ultrasonic vibrations, which are then transmitted along waveguide (280), including flexible portion (266) of waveguide (280) to blade (260) in accordance with known configurations and techniques. By way of example only, this portion of the acoustic drivetrain may be configured in accordance with various teachings of various references that are cited herein.

As with flexible portion (166) of waveguide (180) discussed above, flexible portion (266) of waveguide (280) includes a narrowed section (264). Narrowed section (264) is configured to allow flexible portion (266) of waveguide (280) to flex without significantly affecting the ability of flexible portion (266) of waveguide (280) to transmit ultrasonic vibrations. By way of example only, narrowed section (264) may be configured in accordance with one or more teachings of U.S. Pub. No. 2014/0005701, issued as U.S. Pat. No. 9,393,037 on Jul. 19, 2016 and/or U.S. Pub. No. 2014/0114334, issued as U.S. Pat. No. 9,095,367 on Aug. 4, 2015, the disclosures of which are incorporated by reference herein. It should be understood that waveguide (280) may be configured to amplify mechanical vibrations transmitted through waveguide (280). Furthermore, waveguide (280) may include features operable to control the gain of the longitudinal vibrations along waveguide (280) and/or features to tune waveguide (280) to the resonant frequency of the system. Various suitable ways in which waveguide (280) may be mechanically and acoustically coupled with transducer assembly (212) will be apparent to those of ordinary skill in the art in view of the teachings herein.

In the present example, the distal end of blade (260) is located at a position corresponding to an anti-node associated with resonant ultrasonic vibrations communicated through flexible portion (266) of waveguide (280), in order to tune the acoustic assembly to a preferred resonant frequency $f_o$ when the acoustic assembly is not loaded by tissue. When transducer assembly (212) is energized, the distal end of blade (260) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (212) of the present example is activated, these mechanical oscillations are transmitted through waveguide (280) to reach blade (260), thereby providing oscillation of blade (260) at the resonant ultrasonic frequency. Thus, when tissue is secured between blade (260) and clamp pad (246), the ultrasonic oscillation of blade (260) may simultaneously sever the tissue and denature the proteins in adjacent tissue cells, thereby providing a coagulative effect with relatively little thermal spread. In some versions, an electrical current may also be provided through blade (260) and clamp arm (244) to also cauterize the tissue. While some configurations for an acoustic transmission assembly and transducer assembly (212) have been described, still other suitable configurations for an acoustic transmission assembly and transducer assembly (212) will be apparent to one or ordinary skill in the art in view of the teachings herein. Similarly, other suitable configurations for end effector (240) will be apparent to those of ordinary skill in the art in view of the teachings herein.

C. Exemplary Shaft Assembly and Articulation Section

Shaft assembly (230) of the present example extends distally from handle assembly (220). As best seen in FIGS. 11 and 12, shaft assembly (230) includes distal outer sheath (233) and a proximal outer sheath (232) that enclose the drive features of clamp arm (244) and the above-described acoustic transmission features. Shaft assembly (230) further includes an articulation section (330), which is located at a distal portion of shaft assembly (230), with end effector (240) being located distal to articulation section (330).

Articulation section (330) of the present example is configured and operable substantially similar to articulation section (130) discussed above except for the differences discussed below. In particular, articulation section (330) is operable to selectively position end effector (240) at various lateral deflection angles relative to a longitudinal axis defined by outer sheath (232). Articulation section (330) may take a variety of forms. By way of example only, articulation section (330) may be configured in accordance with one or more teachings of U.S. Pub. No. 2012/0078247, issued as U.S. Pat. No. 9,402,682 on Aug. 2, 2016, the disclosure of which is incorporated by reference herein. As another merely illustrative example, articulation section (330) may be configured in accordance with one or more teachings of U.S. Pub. No. 2014/0005701, issued as U.S. Pat. No. 9,393,037 on Jul. 19, 2016 and/or U.S. Pub. No. 2014/0114334, issued as U.S. Pat. No. 9,095,367 on Aug. 4, 2015, the disclosures of which are incorporated by reference herein. Various other suitable forms that articulation section (330) may take will be apparent to those of ordinary skill in the art in view of the teachings herein.

Figure 27A:
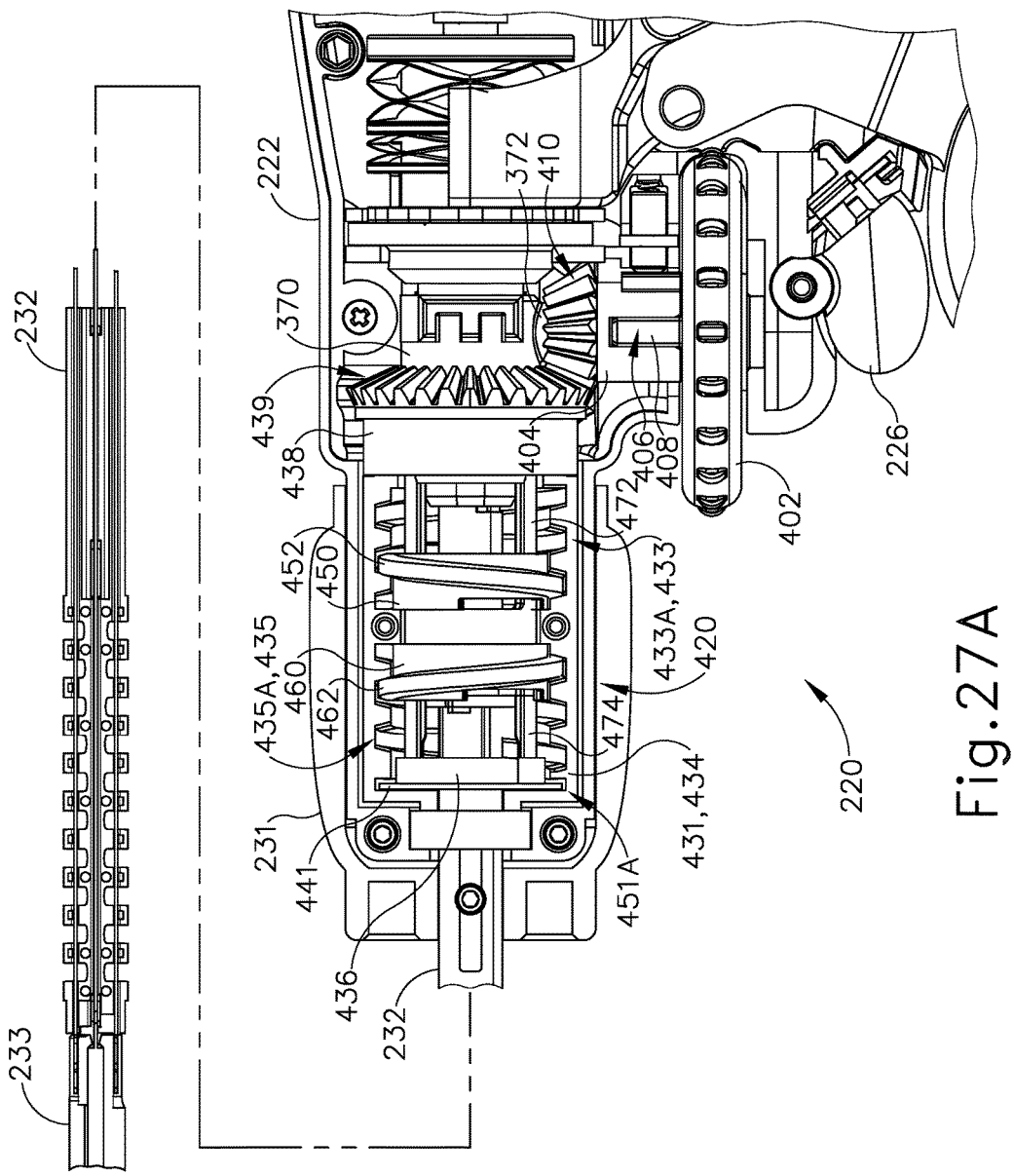
FIG. 27A depicts a detailed side elevational view of the instrument of FIG. 11 with a shrouding half removed, and a cross-sectional top view of an articulation section of the shaft assembly of FIG. 15, with the articulation section in a substantially straight configuration.
Figure 27B:
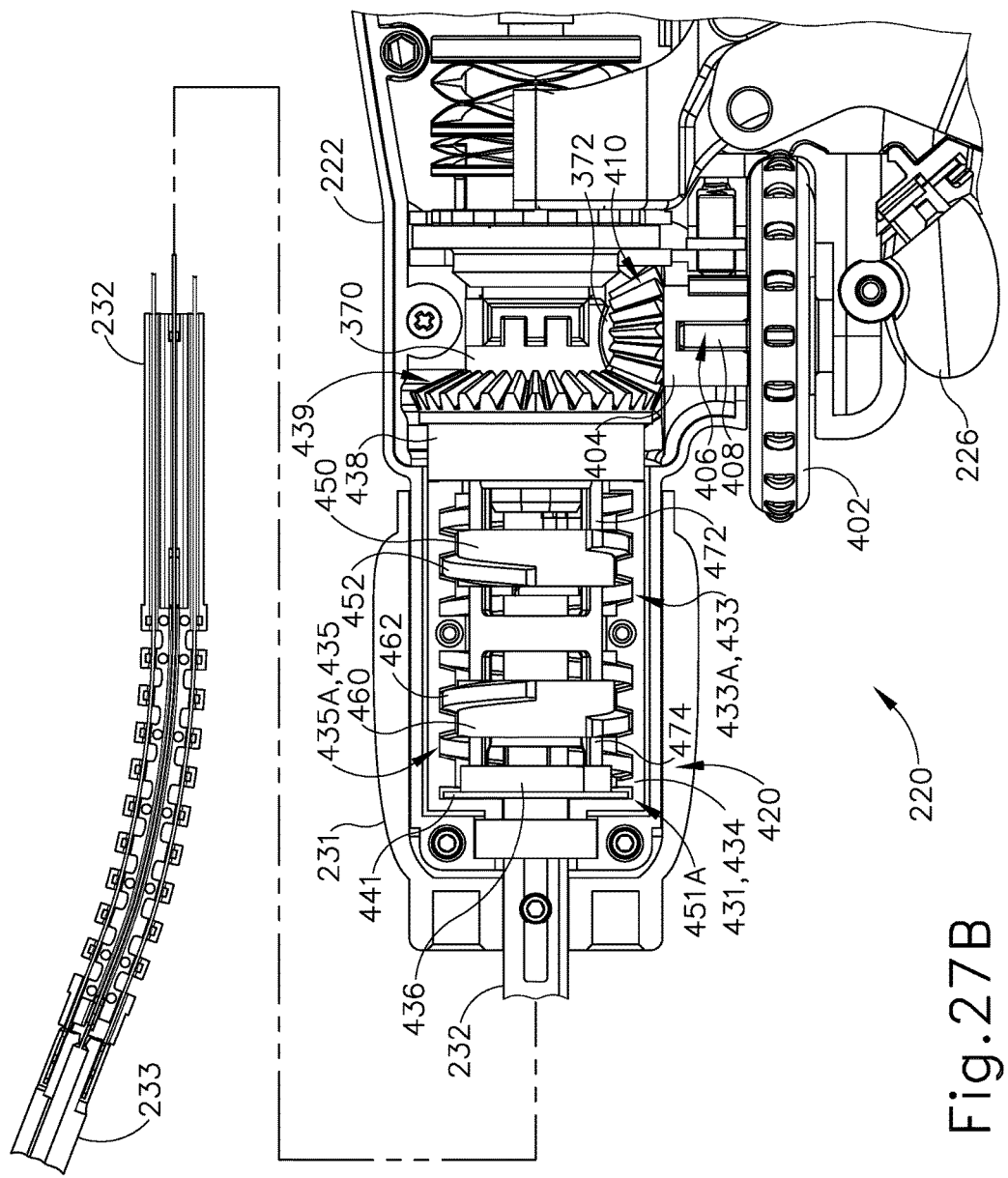
FIG. 27B depicts a detailed side elevational view of the instrument of FIG. 11 with a shrouding half removed, and a cross-sectional top view of the articulation section of FIG. 27A, with the articulation section in a first stage of articulation.
Figure 27C:
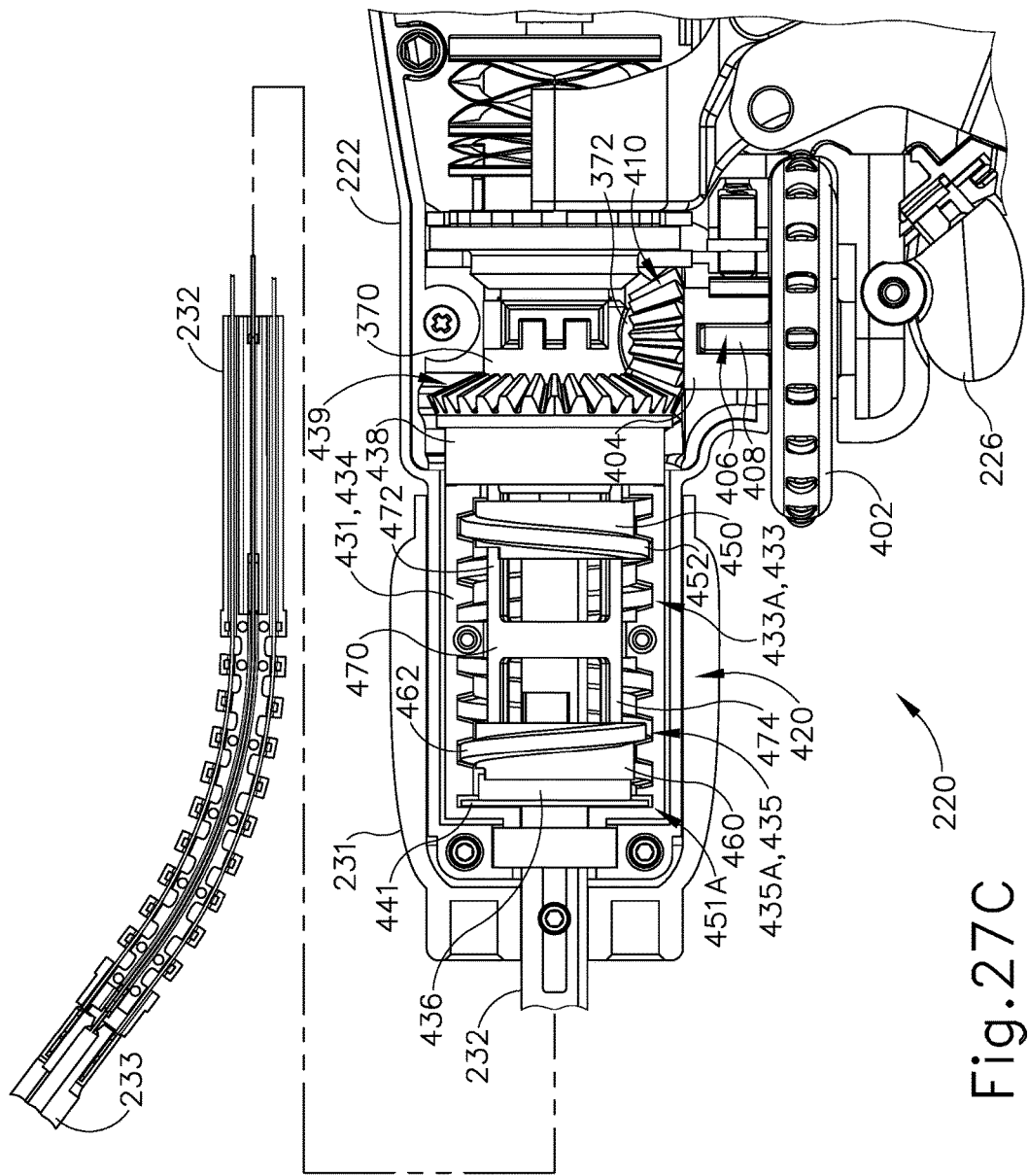
FIG. 27C depicts a detailed side elevational view of the instrument of FIG. 11 with a shrouding half removed, and a cross-sectional top view of the articulation section of FIG. 27A, with the articulation section in a second stage of articulation.

As shown in FIGS. 15-16, shaft assembly (230) further comprises a pair of articulation bands (340, 342) and a pair of translatable rods (440, 442). Articulation bands (340, 342) are configured to operate substantially similar to articulation bands (140, 142) discussed above, except for any differences discussed below. For instance, when articulation bands (340, 342) translate longitudinally in an opposing fashion, this will cause articulation section (330) to bend, thereby laterally deflecting end effector (240) away from the longitudinal axis of shaft assembly (230) from a straight configuration as shown in FIG. 27A to an articulated configuration as shown in FIGS. 27B and 27C. In particular, end effector (240) will be articulated toward the articulation band (340, 342) that is being pulled proximally. During such articulation, the other articulation band (340, 342) may be pulled distally. Alternatively, the other articulation band (340, 342) may be driven distally by articulation control assembly (400), which is described in greater detail below. Flexible acoustic waveguide (266) is configured to effectively communicate ultrasonic vibrations from waveguide (280) to blade (260) even when articulation section (330) is in an articulated state as shown in FIGS. 27B and 27C.

Translatable members (440, 442) are slidably disposed within the proximal portion of outer sheath (232). Translatable members (440, 442) extend longitudinally through the proximal portion of outer sheath (232) along opposite sides of outer sheath (232) and adjacent an interior surface of outer sheath (232). As shown in FIG. 16, an elongate recess (444) is formed in an exterior surface of a distal portion of each translatable member (440, 442). Elongate recesses (444) are configured to receive a proximal portion of each articulation band (340, 342). Each translatable member (440, 442) further includes a pin (443) projecting outwardly from an interior surface of each elongate recess (444). An opening (341) formed in a proximal end of each articulation band (340, 342) is configured to receive a respective pin (443) of translatable members (440, 442). Pins (443) and openings (341, 343) thus function to mechanically couple translatable members (440, 442) with articulation bands (340, 342) such that longitudinal translation of translatable member (440) causes concurrent longitudinal translation of articulation band (340), and such that longitudinal translation of translatable member (442) causes concurrent longitudinal translation of articulation band (342).

When translatable members (440, 442) and articulation bands (340, 342) are translated longitudinally in an opposing fashion, a moment is created and applied to a distal end of distal outer sheath (233) in the same manner as described above with respect to articulation section (130). This causes articulation section (330) and narrowed section (264) of flexible portion (266) of waveguide (280) to articulate, without transferring axial forces in articulation bands (340, 342) to waveguide (280) as described above. It should be understood that one articulation band (340, 342) may be actively driven distally while the other articulation band (340, 342) is passively permitted to retract proximally. As another merely illustrative example, one articulation band (340, 342) may be actively driven proximally while the other articulation band (340, 342) is passively permitted to advance distally. As yet another merely illustrative example, one articulation band (340, 342) may be actively driven distally while the other articulation band (340, 342) is actively driven proximally. Various suitable ways in which articulation bands (340, 342) may be driven will be apparent to those of ordinary skill in the art in view of the teachings herein.

As shown in FIGS. 11-14, a rotation knob (231) is secured to a proximal portion of proximal outer sheath (232). Rotation knob (231) is rotatable relative to body (222), such that shaft assembly (230) is rotatable about the longitudinal axis defined by outer sheath (232), relative to handle assembly (220). Such rotation may provide rotation of end effector (240), articulation section (330), and shaft assembly (230) unitarily. Of course, rotatable features may simply be omitted if desired.

D. Exemplary Articulation Control Assembly

Figure 14:
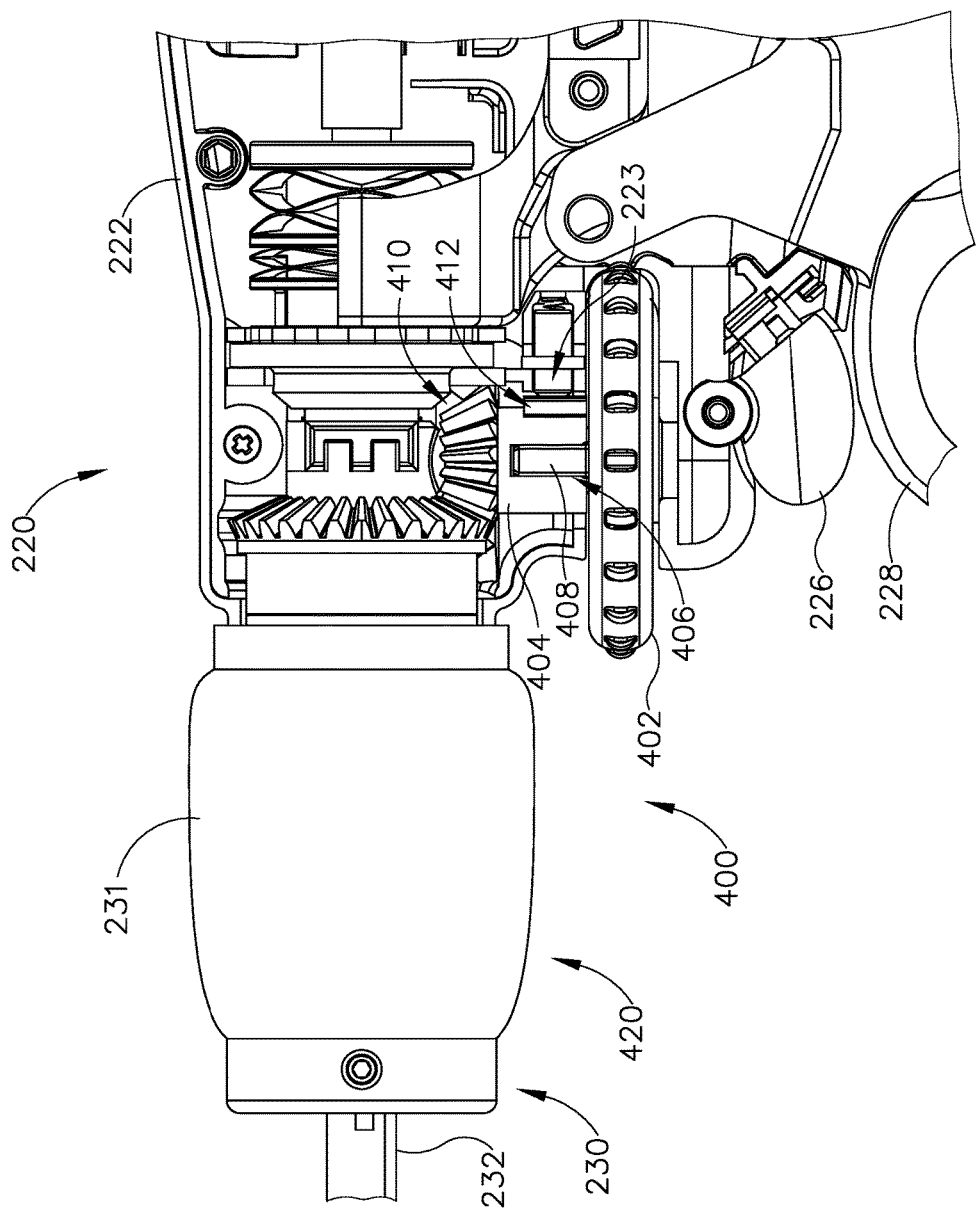
FIG. 14 depicts a detailed side elevational view of the instrument of FIG. 11 with a shrouding half removed.

FIGS. 17-27C show the components and operation of an articulation control assembly (400) that is configured to provide control for articulation of articulation section (330). Articulation control assembly (400) comprises an articulation control knob (402) and a bevel gear (404). Articulation control knob (402) is rotatably disposed within a distal portion of body (222) of handle assembly (220). As best seen in FIG. 14, articulation control knob (402) is oriented within body (222) and relative to shaft assembly (230) such that articulation control knob (402) is configured to rotate about an axis that is perpendicular to the longitudinal axis defined by shaft assembly (230). A portion of articulation control knob (402) is exposed relative to body (222) such that an operator may engage articulation control knob (402) to thereby rotate articulation control knob (402). For example, while gripping body (222) via pistol grip (224), an operator may use his or her index finger or thumb to rotate articulation control knob (402). It should therefore be understood that the operator may rotate knob (402) using the same hand that grasps pistol grip (224). As will be described in more detail below, rotation of articulation control knob (402) is configured to cause articulation of articulation section (330). Since the operator may use the same hand to rotate knob (402) and simultaneously grasp pistol grip (224), articulation control assembly (400) of this example provides full control of instrument (200)—including pivoting of trigger (228), actuation of button (226), and actuation of knob (402)—with just one single hand, such the operator's other hand may be completely free during the entire period when any and all functionality of instrument (200) is being used.

Figure 17:
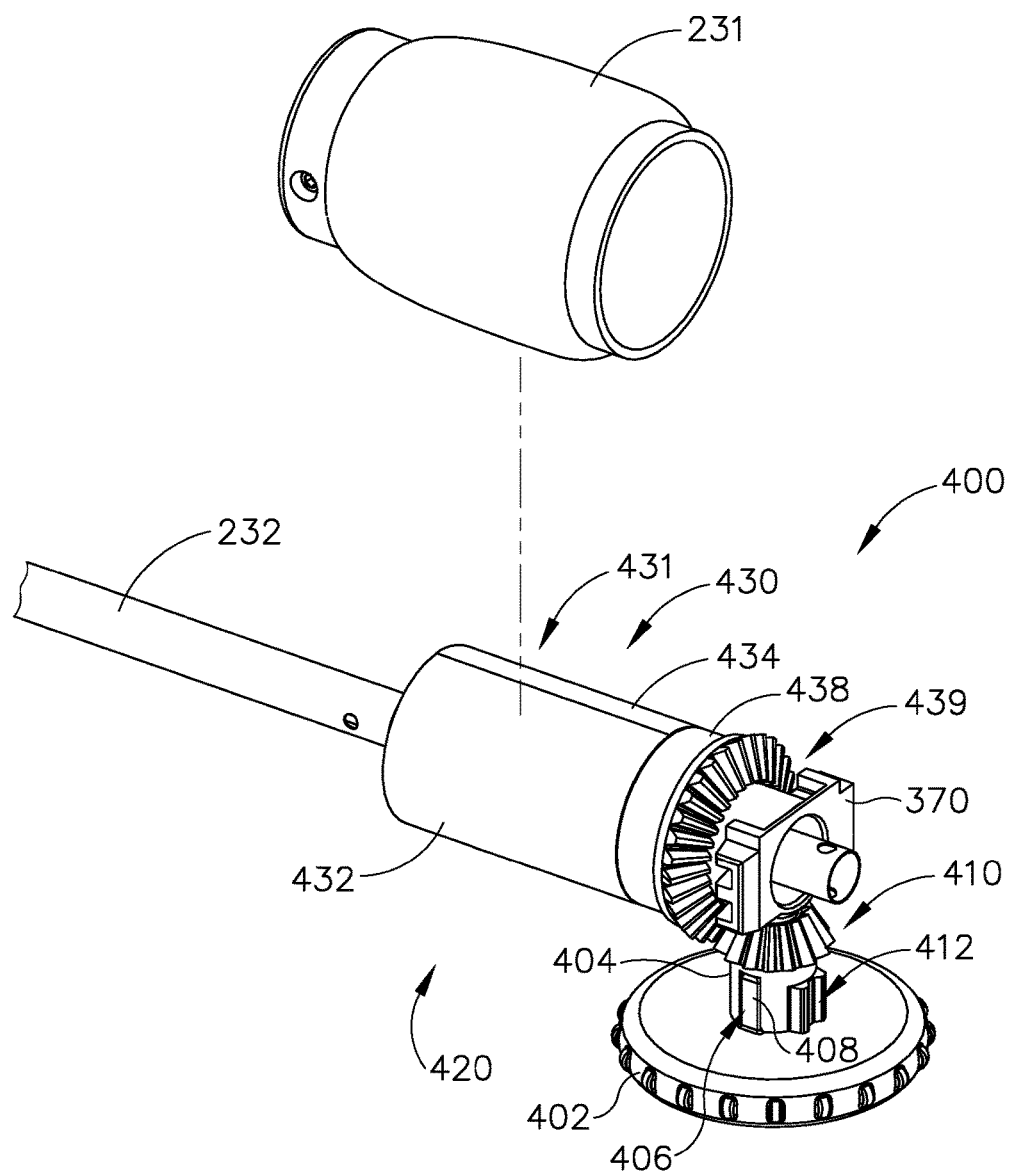
FIG. 17 depicts a partially exploded perspective view of an articulation control assembly of the instrument of FIG. 11.
Figure 18:
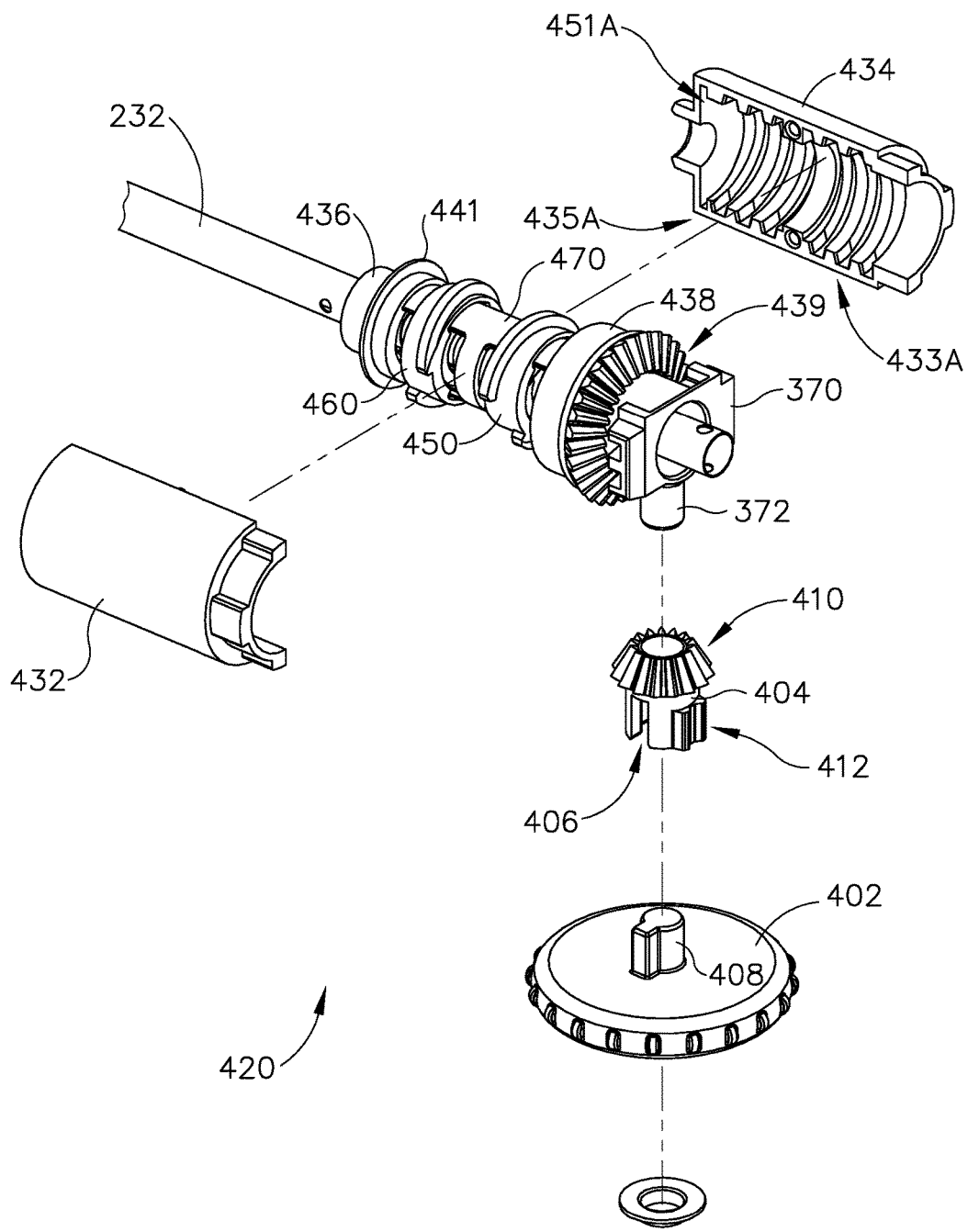
FIG. 18 depicts an exploded perspective view of a drive assembly of the articulation control assembly of FIG. 17.
Figure 19:
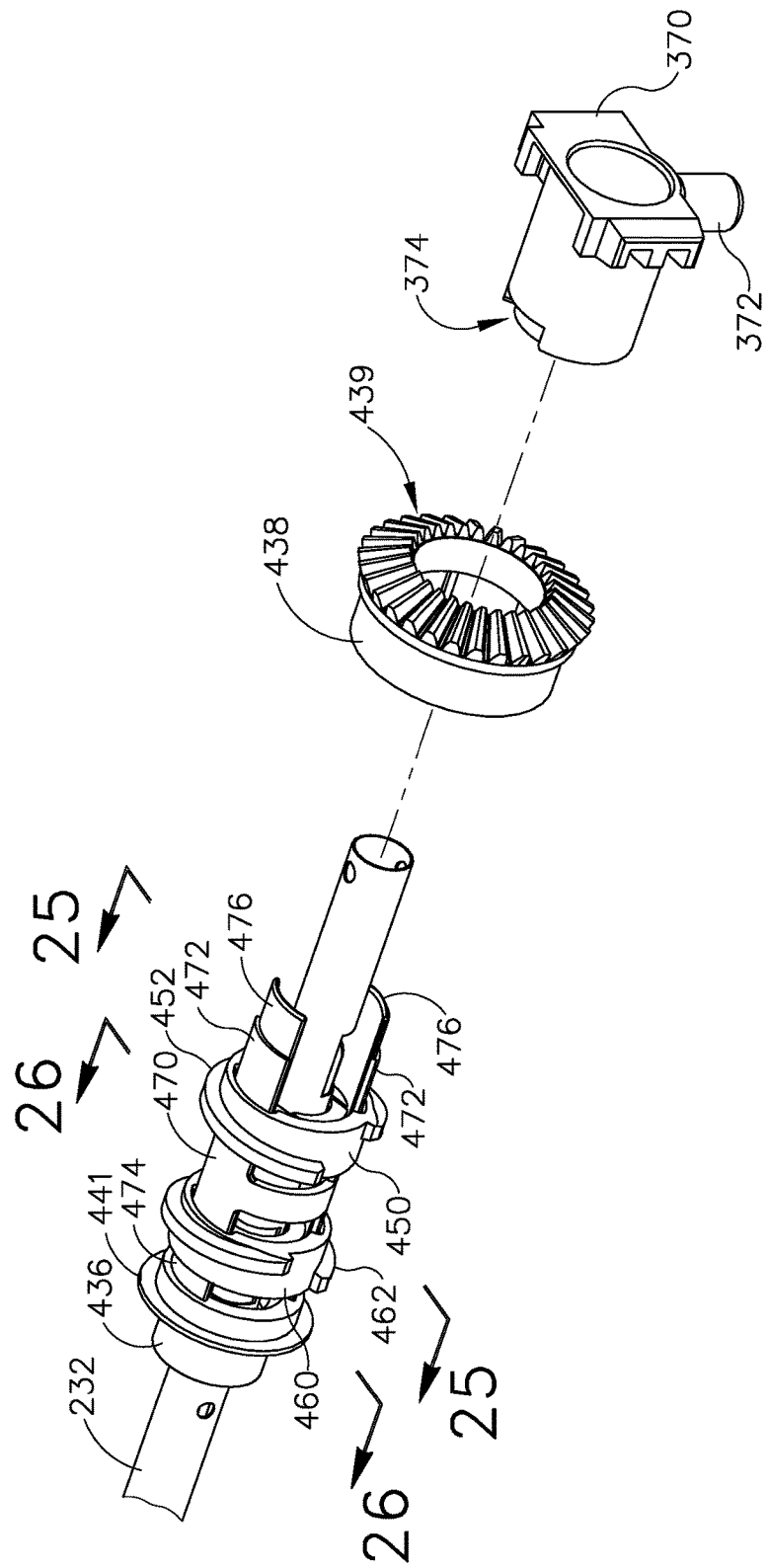
FIG. 19 depicts another partially exploded perspective view of the drive assembly of FIG. 18.

Articulation control assembly (400) further includes a structural frame (370) secured within a proximal portion of an interior of body (222) of handle assembly (220) such that structural frame (370) is configured to remain stationary within body (222). As best seen in FIGS. 17 and 18, bevel gear (404) is rotatably disposed about a cylindrical projection (372) of structural frame (370). As best seen in FIG. 14, bevel gear (404) is mechanically coupled with articulation control knob (402) via a slot (406) formed in bevel gear (404) and a mating key (408) projecting from a top surface of articulation control knob (402) such that rotation of articulation control knob (402) causes concurrent rotation of bevel gear (404) about cylindrical projection (372) of structural frame (370). Bevel gear (404) includes a plurality of teeth (410) and a detent feature (412). As will be described in more detail below, teeth (410) of bevel gear (404) mesh with teeth (439) of a bevel gear (438) of a drive assembly (420), such that rotation of bevel gear (404) drives articulation of articulation section (330).

Detent feature (412) is configured to selectively engage a complementary, resiliently biased detent feature (223) of handle assembly (220) as best seen in FIG. 14. Detent feature (412) is positioned to engage detent feature (223) when control knob (402) is rotated to a "neutral" position associated with articulation section (330) being in a straight configuration. It should therefore be understood that detent features (224, 412) may cooperate to provide the operator with tactile feedback via control knob (402) to indicate that articulation section (330) is in the straight configuration. Detent features (224, 412) may also cooperate to provide some degree of mechanical resistance to rotation of knob (402) from the neutral position, thereby resisting inadvertent articulation of articulation section (330) that might otherwise result from incidental contact between knob (402) and the operator's hand, etc.

In addition to or in lieu of including detent features (224, 412), knob (402) may include a visual indicator that is associated with articulation section (330) being in a substantially straight configuration. Such a visual indicator may align with a corresponding visual indicator on body (222) of handle assembly (220). Thus, when an operator has rotated knob (402) to make articulation section (330) approach a substantially straight configuration, the operator may observe such indicators to confirm whether articulation section (330) has in fact reached a substantially straight configuration. By way of example only, this may be done right before instrument (200) is withdrawn from a trocar to reduce the likelihood of articulation section (330) snagging on a distal edge of the trocar. Of course, such indicators are merely optional.

As best seen in FIG. 17, articulation control assembly (400) further comprises a drive assembly (420). Drive assembly (420) is secured to a proximal portion of proximal outer sheath (232). Drive assembly (420) is further rotatably disposed within rotation knob (231) such that rotation knob (231) is configured to rotate independently about drive assembly (420) to thereby cause rotation of shaft assembly (230) without causing rotation of drive assembly (420).

Drive assembly (420) comprises a housing (430), a pair of lead screws (450, 460), and a cylindrical guide (470). Housing (430) comprises a pair of mating semi-cylindrical shrouding halves (432, 434) and a bevel gear (438). When coupled to one another, shrouding halves (432, 434) form a cylindrical shroud (431). A proximal end of shroud (431) is coupled with and closed-off by bevel gear (438). Shroud (431), together with bevel gear (438), form housing (430) which substantially encompasses the internal components of drive assembly (420) as will be described in more detail below.

Bevel gear (438) includes a plurality of teeth (439). Teeth (439) of bevel gear (438) are configured to engage teeth (410) of bevel gear (404) such that rotation of bevel gear (404) causes concurrent rotation of bevel gear (438). It should therefore be understood that rotation of articulation control knob (402) is configured to cause concurrent rotation of housing (430) via bevel gears (404, 438).

As best seen in FIG. 18, shrouding halves (432, 434) each include proximal internal threading (433A) formed in an interior surface of each shrouding half (432, 434). Internal threadings (433A) are configured to align with one another when shrouding halves (432, 434) are coupled together to form a continuous internal proximal threading (433) within housing (430). Shrouding halves (432, 434) each further include distal internal threading (435A) formed in an interior surface of each shrouding half (432, 434). Internal threadings (435A) are configured to align with one another when shrouding halves (432, 434) are coupled together to form a continuous internal distal threading (435) within housing (430). Threadings (433, 435) have opposing pitch angles or orientations in this example, such that the pitch orientation of threading (433) is opposite the pitch orientation of threading (435).

As shown in FIGS. 20-21, a first lead screw (450) includes exterior threading (452) that is configured to engage with threading (433) of housing (430). As shown in FIGS. 22-23 a second lead screw (460) includes exterior threading (462) that is configured to engage with threading (435) of housing (430). The pitch angle of threading (452) complements the pitch angle of threading (433); while the pitch angle of threading (462) complements the pitch angle of threading (435). As described in greater detail below, both lead screws (450, 460) are permitted to translate within drive assembly (420) but are prevented from rotating within drive assembly (420). It should therefore be understood that, due to the opposing pitch angles, rotation of housing (430) in a first direction will drive lead screw (450) distally while simultaneously driving lead screw (460) proximally; and rotation of housing (430) in a second direction will drive lead screw (450) proximally while simultaneously driving lead screw (460) distally.

Figure 24A:
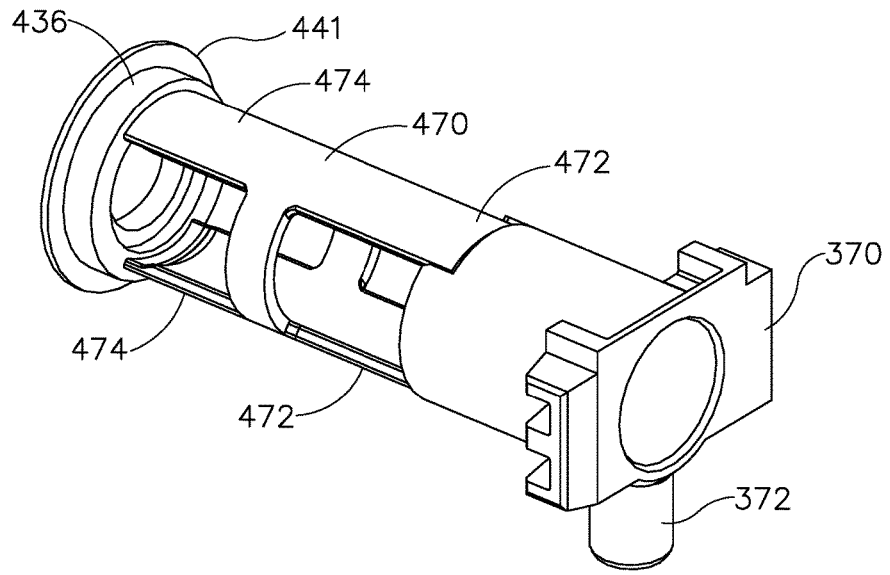
FIG. 24A depicts a perspective view of a cylindrical guide of the drive assembly of FIG. 18.
Figure 24B:
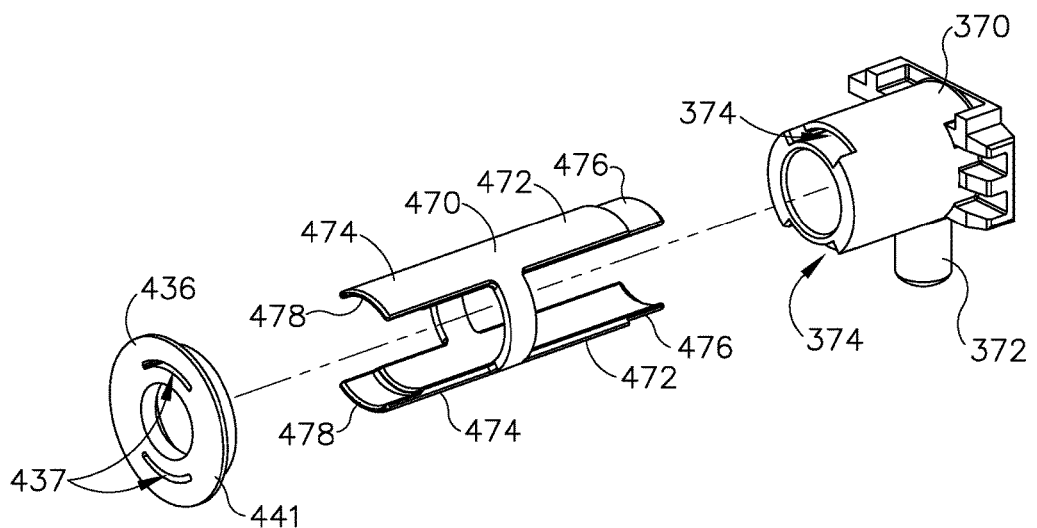
FIG. 24B depicts a partially exploded perspective view of the cylindrical guide of FIG. 24A.

As best seen in FIGS. 21 and 23, a through-bore (454, 464) formed in each lead screw (450, 460) includes a pair of recesses (456, 466) formed in radially opposing sides of an interior surface of through-bores (454, 464). Cylindrical guide (470) is positioned within housing (430) about the proximal portion of outer sheath (232). As shown in FIGS. 24A and 24B, cylindrical guide (470) is secured to a distal end of structural frame (370) via a pair of semi-circular recesses (374) formed in the distal end of structural frame (370) and a pair of semi-circular projections (476) extending proximally from cylindrical guide (470). Thus, with structural frame (370) secured within the proximal portion of the interior of body (222) of handle assembly (220) as described above, cylindrical guide (470) is configured to remain stationary within housing (430). A bearing member (436) is coupled to a distal end of cylindrical guide (470) via a pair of semi-circular recesses (437) formed in bearing member (436) and a pair of semi-circular projections (478) extending distally from cylindrical guide (470). A circular flange (441) of bearing member (436) is rotatable disposed within a pair of mating circular recesses (451A) formed in a distal end of shroud halves (432, 434) such that housing (430) is operable to rotate about bearing member (436).

Figure 25:
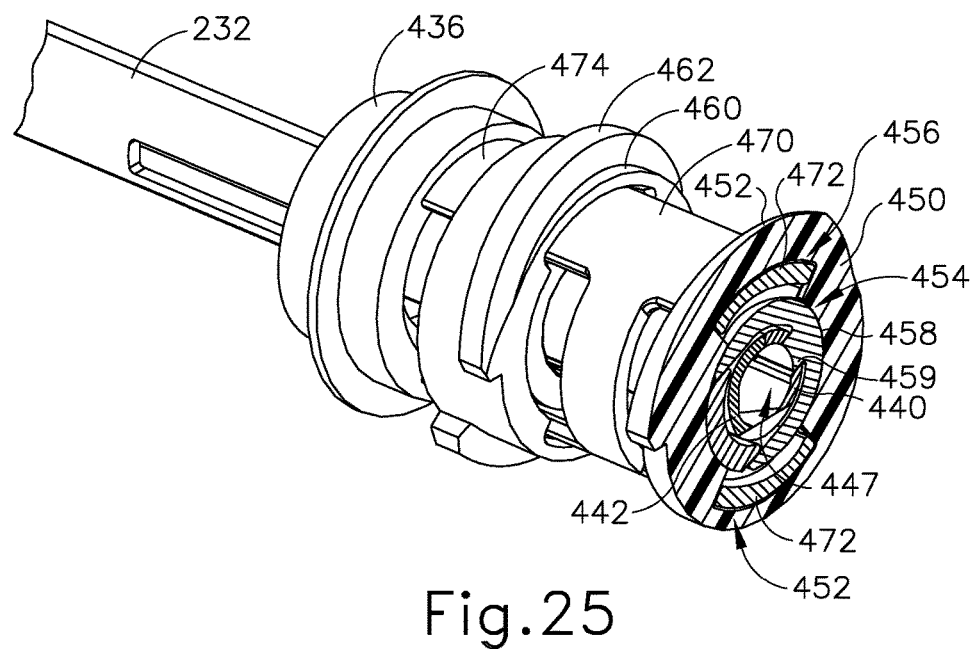
FIG. 25 depicts a cross-sectional perspective view of the drive assembly of FIG. 18, taken along the line 25-25 of FIG. 19.
Figure 26:
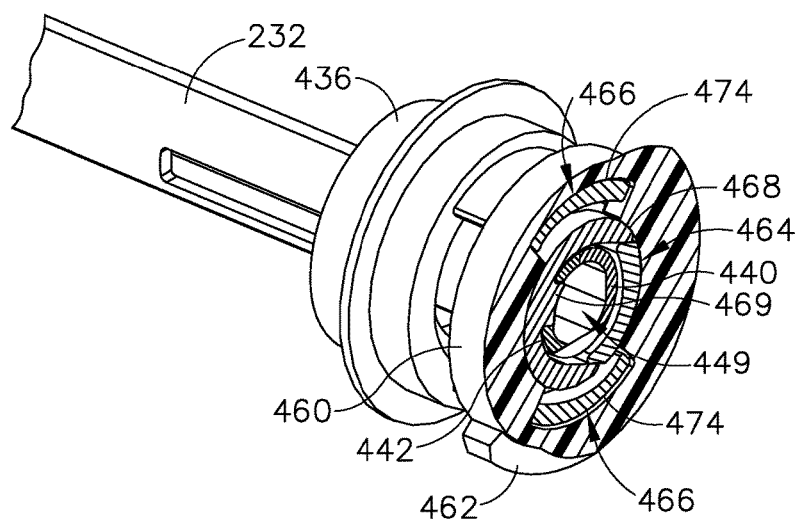
FIG. 26 depicts a cross-sectional perspective view of the drive assembly of FIG. 18, taken along the line 26-26 of FIG. 19.

As best seen in FIGS. 24A and 24B, cylindrical guide (470) comprises a proximal pair of longitudinal tracks (472) and a distal pair of longitudinal tracks (474) formed in opposing sides of a sidewall of cylindrical guide (470). As shown in FIG. 25, proximal longitudinal tracks (472) are configured to be received within recesses (456) of first lead screw (450) such that first lead screw (450) is slidably disposed along proximal longitudinal tracks (472). As shown in FIG. 26, distal longitudinal tracks (474) are configured to be received within recesses (466) of second lead screw (460) such that second lead screw (460) is slidably disposed along distal longitudinal tracks (474). Thus, lead screws (450, 460) are operable to translate within housing (430) but are prevented from rotating within housing (430).

As shown in FIG. 25, first lead screw (450) is secured to a proximal end of translatable member (440) via a coupler (458). An exterior surface of coupler (458) is secured to an interior surface of through-bore (454) of first lead screw (450). A key (459) of coupler (458) is positioned within a mating slot (447) formed in the proximal end of translatable member (440) such that longitudinal translation of first lead screw (450) causes concurrent translation of translatable member (440) and articulation band (340). Thus, in the present version, first lead screw (450) is operable to both push articulation band (340) distally and pull articulation band (340) proximally, depending on which direction housing (430) is rotated. Other suitable relationships will be apparent to those of ordinary skill in the art in view of the teachings herein.

As shown in FIG. 26, second lead screw (460) is secured to a proximal end of translatable member (442) via a coupler (468). An exterior surface of coupler (468) is secured to an interior surface of through-bore (464) of second lead screw (460). A key (469) of coupler (468) is positioned within a mating slot (449) formed in the proximal end of translatable member (442) such that longitudinal translation of second lead screw (460) causes concurrent translation of translatable member (422) and articulation band (342). Thus, in the present version, second lead screw (460) is operable to both push articulation band (342) distally and pull articulation band (342) proximally, depending on which direction housing (430) is rotated. Other suitable relationships will be apparent to those of ordinary skill in the art in view of the teachings herein.

FIGS. 27A-27C show several of the above described components interacting to bend articulation section (330) to articulate end effector (240) in response to rotation of knob (402) relative to handle assembly (220). It should be understood that in FIGS. 27A-27C depicts a side elevational view of handle assembly (220) and a top plan view of shaft assembly (230), including articulation section (330). In FIG. 27A, articulation section (330) is in a substantially straight configuration. Then, housing (430) is rotated by rotation of articulation knob (402). In particular, rotation of articulation knob (402) is communicated to housing (430) via meshing bevel gears (410, 438). The resulting rotation of housing (430) which causes first lead screw (450) to translate proximally and second lead screw (460) to advance distally. This proximal translation of first lead screw (450) pulls articulation band (340) proximally via translatable member (440), which causes articulation section (330) to start bending as shown in FIG. 27B. This bending of articulation section (330) pulls articulation band (342) distally. The distal advancement of second lead screw (460) in response to rotation of housing (430) enables articulation band (342) and translatable member (442) to advance distally. In some other versions, the distal advancement of second lead screw (460) actively drives translatable member (442) and articulation band (342) distally. As the operator continues rotating housing (430) by rotating articulation knob (402), the above described interactions continue in the same fashion, resulting in further bending of articulation section (330) as shown in FIG. 27C.

It should be understood that, after reaching the articulation state in FIG. 27C by rotating knob (402) in a first direction, rotation of knob (402) in a second (opposite) direction will cause articulation section (330) to return to the straight configuration shown in FIG. 27A. As noted above, detent features (224, 412) may cooperate to provide tactile feedback via knob (402) to indicate that articulation section (330) has reached the straight configuration. Still further rotation of knob (402) in that second direction will eventually result in articulation section (330) deflecting in a direction opposite to that shown in FIGS. 27B-27C.

The angles of threading (433, 435, 452, 462) are configured such that articulation section (330) will be effectively locked in any given articulated position, such that transverse loads on end effector (240) will generally not bend articulation section (330), due to friction between threading (433, 435, 452, 462). In other words, articulation section (330) will only change its configuration when housing (430) is rotated via knob (402). While the angles of threading may substantially prevent bending of articulation section (330) in response to transverse loads on end effector (240), the angles may still provide ready rotation of housing (430) to translate lead screws (450, 460). By way of example only, the angles of threading (433, 435, 452, 462) may be approximately +/−2 degrees or approximately +/−3 degrees. Other suitable angles will be apparent to those of ordinary skill in the art in view of the teachings herein. It should also be understood that threading (433, 435, 452, 462) may have a square or rectangular cross-section or any other suitable configuration.

In some instances, manufacturing inconsistencies may result in articulation bands (340, 342) and/or translatable members (440, 442) having slightly different lengths. In addition or in the alternative, there may be inherent manufacturing related inconsistencies in the initial positioning of lead screws (450, 460) relative to housing (430) and/or other inconsistencies that might result in undesirable positioning/relationships of articulation bands (340, 342) and/or translatable members (440, 442). Such inconsistencies may result in lost motion or slop in the operation of the articulation features of instrument (200). To address such issues, tensioner gears (not shown) may be incorporated into drive assembly (420) to adjust the longitudinal position of translatable members (440, 442) relative to lead screws (450, 460). Lead screws (450, 460) may remain substantially stationary during such adjustments. Articulation section (330) may remain substantially straight during such adjustments and may even be held substantially straight during such adjustments.

In addition to or in lieu of the foregoing, drive assembly (420) may be configured and operable in accordance with at least some of the teachings of U.S. Pub. No. 2013/0023868, entitled "Surgical Instrument with Contained Dual Helix Actuator Assembly," published Jan. 24, 2013, issued as U.S. Pat. No. 9,545,253 on Jan. 17, 2017, the disclosure of which is incorporated by reference herein; in U.S. Pub. No. 2012/0078243, entitled "Control Features for Articulating Surgical Device," published Mar. 29, 2012, issued as U.S. Pat. No. 9,877,720 on Jan. 30, 2018, the disclosure of which is incorporated by reference herein; and in U.S. Pub. No. 2012/0078244, entitled "Control Features for Articulating Surgical Device," published Mar. 29, 2012, now abandoned, the disclosure of which is incorporated by reference herein.

III. Exemplary Motorized Articulation Control Assembly and Rigidizing Member

In some versions of instruments (10, 200) it may be desirable to provide motorized control of articulation section (130, 330). This may further promote single-handed use of the instrument, such that two hands are not required in order to control articulation section (130, 300).

It may also be desirable to provide features that are configured to selectively provide rigidity to articulation sections (130, 330). For instance, because of various factors such as manufacturing tolerances, design limitations, material limitations, and/or other factors, some versions of articulation sections (130, 330) may be susceptible to some "play" or other small movement of the articulation section despite being relatively fixed in a given position, such that articulation sections (130, 330) are not entirely rigid. It may be desirable to reduce or eliminate such play in articulation sections (130, 330), particularly when articulation sections (130, 330) are in a straight, non-articulated configuration. Features may thus be provided to selectively rigidize articulation sections (130, 330). Various examples of features that are configured to selectively provide rigidity to articulation sections (130, 330) and/or to limit or prevent inadvertent deflection of end effectors (40, 240) will be described in greater detail below. Other examples will be apparent to those of ordinary skill in the art according to the teachings herein. It should be understood that the examples of shaft assemblies and/or articulation sections described below may function substantially similar to shaft assemblies (30, 230) discussed above.

It should also be understood that articulation sections (130, 330) may still be at least somewhat rigid before being modified to include the rigidizing features described below, such that the rigidizing features described below actually just increase the rigidity of articulation sections (130, 330) rather than introducing rigidity to otherwise non-rigid articulation sections (130, 330). For instance, articulation sections (130, 330) in the absence of features as described below may be rigid enough to substantially maintain a straight or articulated configuration; yet may still provide "play" of about 1 mm or a fraction thereof such that the already existing rigidity of articulation sections (130, 330) may be increased. Thus, terms such as "provide rigidity," "providing rigidity," "rigidize," and "rigidizing," etc. shall be understood to include just increasing rigidity that is already present in some degree. The terms "provide rigidity," "providing rigidity," "rigidize," and "rigidizing," etc. should not be read as necessarily requiring articulation sections (130, 330) to completely lack rigidity before the rigidity is "provided."

A. Overview

Figure 30:
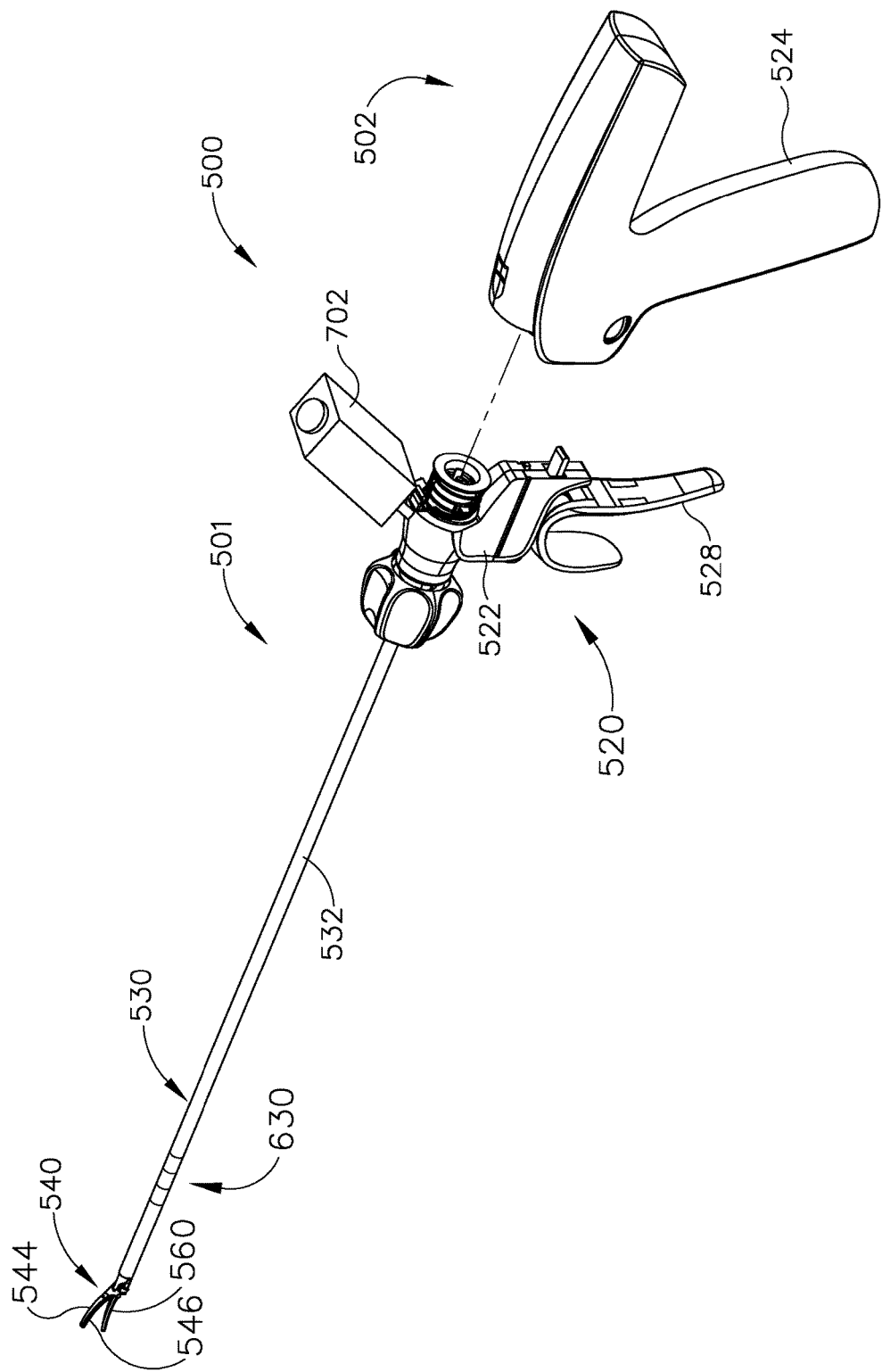
FIG. 30 depicts a perspective view of the instrument of FIG. 28, with a disposable portion separated from a reusable portion.

FIGS. 28-30 show an exemplary ultrasonic surgical instrument (500) that is configured to be used in minimally invasive surgical procedures (e.g., via a trocar or other small diameter access port, etc.). As will be described in greater detail below, instrument (500) is operable to cut tissue and seal or weld tissue (e.g., a blood vessel, etc.) substantially simultaneously. Instrument (500) of this example comprises a disposable assembly (501) and a reusable assembly (502). The distal portion of reusable assembly (502) is configured to removably receive the proximal portion of disposable assembly (501), as seen in FIGS. 29-30, to form instrument (500). By way of example only, instrument (500) may be configured and operable in accordance with at least some of the teachings of U.S. patent application Ser. No. 14/623,812, entitled "Ultrasonic Surgical Instrument with Removable Handle Assembly," filed Feb. 17, 2015, issued as U.S. Pat. No. 10,010,340 on Jul. 3, 2018, the disclosure of which is incorporated by reference herein.

In an exemplary use, assemblies (501, 502) are coupled together to form instrument (500) before a surgical procedure, the assembled instrument (500) is used to perform the surgical procedure, and then assemblies (501, 502) are decoupled from each other for further processing. In some instances, after the surgical procedure is complete, disposable assembly (501) is immediately disposed of while reusable assembly (502) is sterilized and otherwise processed for re-use. By way of example only, reusable assembly (502) may be sterilized in a conventional relatively low temperature, relatively low pressure, hydrogen peroxide sterilization process. Alternatively, reusable assembly (502) may be sterilized using any other suitable systems and techniques (e.g., autoclave, etc.). In some versions, reusable assembly (502) may be sterilized and reused approximately 100 times. Alternatively, reusable assembly (502) may be subject to any other suitable life cycle. For instance, reusable assembly (502) may be disposed of after a single use, if desired. While disposable assembly (501) is referred to herein as being "disposable," it should be understood that, in some instances, disposable assembly (501) may also be sterilized and otherwise processed for re-use. By way of example only, disposable assembly (501) may be sterilized and reused approximately 2-30 times, using any suitable systems and techniques. Alternatively, disposable assembly (501) may be subject to any other suitable life cycle.

In some versions, disposable assembly (501) and/or reusable assembly (502) includes one or more features that are operable to track usage of the corresponding assembly (501, 502), and selectively restrict operability of the corresponding assembly (501, 502) based on use. For instance, disposable assembly (501) and/or reusable assembly (502) may include one or more counting sensors and a control logic (e.g., microprocessor, etc.) that is in communication with the counting sensor(s). The counting sensor(s) may be able to detect the number of times the ultrasonic transducer of instrument (500) is activated, the number of surgical procedures the corresponding assembly (501, 502) is used in, the number of trigger closures, and/or any other suitable conditions associated with use. The control logic may track data from the counting sensor(s) and compare the data to one or more threshold values. When the control logic determines that one or more threshold values have been exceeded, the control logic may execute a control algorithm to disable operability of one or more components in the corresponding assembly (501, 502). In instances where the control logic stores two or more threshold values (e.g., a first threshold for number of activations and a second threshold for number of surgical procedures, etc.), the control logic may disable operability of one or more components in the corresponding assembly (501, 502) the first time one of those thresholds is exceeded, or on some other basis.

In versions where a control logic is operable to disable instrument (500) based on the amount of use, the control logic may also determine whether instrument (500) is currently being used in a surgical procedure, and refrain from disabling instrument (500) until that particular surgical procedure is complete. In other words, the control logic may allow the operator to complete the current surgical procedure but prevent instrument (500) from being used in a subsequent surgical procedure. Various suitable forms that counters or other sensors may take will be apparent to those of ordinary skill in the art in view of the teachings herein. Various suitable forms that a control logic may take will also be apparent to those of ordinary skill in the art in view of the teachings herein. Similarly, various suitable control algorithms that may be used to restrict usage of instrument (500) will be apparent to those of ordinary skill in the art in view of the teachings herein. Of course, some versions of instrument (500) may simply omit features that track and/or restrict the amount of usage of instrument (500).

As shown in FIGS. 31-75C, disposable assembly (501) of the present example comprises a body portion (520), a shaft assembly (530) extending distally from body portion (520), and an end effector (540) disposed at a distal end of shaft assembly (530). Body portion (520) of the present example comprises a housing (522) which includes a button (526). Button (526) is operable just like button (226) described above. Body portion (520) also includes a trigger (528) that is pivotable toward and away from a pistol grip (524) of reusable assembly (502) to selectively actuate end effector (540) as described above and as described in one or more of the references cited herein. It should be understood, however, that various other suitable configurations may be used, including but not limited to a scissor grip configuration. End effector (540) includes an ultrasonic blade (560) and a pivoting clamp arm (544). Clamp arm (544) is coupled with trigger (528) such that clamp arm (544) is pivotable toward ultrasonic blade (560) in response to pivoting of trigger (528) toward pistol grip (524); and such that clamp arm (544) is pivotable away from ultrasonic blade (560) in response to pivoting of trigger (528) away from pistol grip (524). Various suitable ways in which clamp arm (544) may be coupled with trigger (528) will be apparent to those of ordinary skill in the art in view of the teachings herein. In some versions, one or more resilient members are used to bias clamp arm (544) and/or trigger (528) to the open position shown in FIGS. 28-30. It should also be understood that clamp arm (544) may be omitted if desired.

B. Exemplary End Effector and Acoustic Drivetrain

As discussed above, end effector (540) of the present example comprises clamp arm (544) and ultrasonic blade (560). Clamp arm (544) includes a clamp pad (546) that is secured to the underside of clamp arm (544), facing ultrasonic blade (560). Clamp pad (546) may comprise PTFE and/or any other suitable material(s). Clamp arm (544) is operable to selectively pivot toward and away from ultrasonic blade (560) to selectively clamp tissue between clamp arm (544) and blade (560).

As with clamp arms (44, 244) discussed above, clamp arm (544) of the present example is pivotally secured to a cable (574). Cable (574) is slidably disposed within an outer sheath (532) of shaft assembly (530) as shown in FIG. 34. Cable (574) is operable to translate longitudinally relative to an articulation section (630) of shaft assembly (530) to selectively pivot clamp arm (544) toward and away from blade (560). In particular, cable (574) is coupled with trigger (528) such that cable (574) translates proximally in response to pivoting of trigger (528) toward pistol grip (524), and such that clamp arm (544) thereby pivots toward blade (560) in response to pivoting of trigger (528) toward pistol grip (524). In addition, cable (574) translates distally in response to pivoting of trigger (528) away from pistol grip (524), such that clamp arm (544) pivots away from blade (560) in response to pivoting of trigger (528) away from pistol grip (524). Clamp arm (544) may be biased toward the open position, such that (at least in some instances) the operator may effectively open clamp arm (544) by releasing a grip on trigger (528).

Blade (560) of the present example is operable to vibrate at ultrasonic frequencies in order to effectively cut through and seal tissue, particularly when the tissue is being compressed between clamp pad (546) and blade (560). Blade (560) is positioned at the distal end of an acoustic drivetrain. Acoustic waveguide (580) comprises a flexible portion (266). As with flexible portions (166, 266) of waveguides (180, 280) discussed above, flexible portion (566) of waveguide (580) includes a narrowed section (564). Narrowed section (564) is configured to allow flexible portion (566) of waveguide (580) to flex without significantly affecting the ability of flexible portion (566) of waveguide (580) to transmit ultrasonic vibrations. By way of example only, narrowed section (564) may be configured in accordance with one or more teachings of U.S. Pub. No. 2014/0005701, issued as U.S. Pat. No. 9,393,037 on Jul. 19, 2016 and/or U.S. Pub. No. 2014/0114334, issued as U.S. Pat. No. 9,095,367 on Aug. 4, 2015, the disclosures of which are incorporated by reference herein. It should be understood that waveguide (580) may be configured to amplify mechanical vibrations transmitted through waveguide (580). Furthermore, waveguide (580) may include features operable to control the gain of the longitudinal vibrations along waveguide (580) and/or features to tune waveguide (580) to the resonant frequency of the system.

In the present example, the distal end of blade (560) is located at a position corresponding to an anti-node associated with resonant ultrasonic vibrations communicated through flexible portion (566) of waveguide (580), in order to tune the acoustic assembly to a preferred resonant frequency $f_o$ when the acoustic assembly is not loaded by tissue. When tissue is secured between blade (560) and clamp pad (546), the ultrasonic oscillation of blade (560) may simultaneously sever the tissue and denature the proteins in adjacent tissue cells, thereby providing a coagulative effect with relatively little thermal spread. In some versions, an electrical current may also be provided through blade (560) and clamp arm (544) to also cauterize the tissue.

C. Exemplary Shaft Assembly, Articulation Section, and Rigidizing Features

Shaft assembly (530) of the present example extends distally from body portion (520). As best seen in FIGS. 33-34, shaft assembly (530) includes distal outer sheath (533) and a proximal outer sheath (532) that enclose the drive features of clamp arm (544) and the above-described acoustic transmission features. Shaft assembly (530) further includes an articulation section (530), which is located at a distal portion of shaft assembly (530), with end effector (540) being located distal to articulation section (630).

Articulation section (630) of the present example is configured to operate substantially similar to articulation sections (130, 330) discussed above except for any differences discussed below. In particular, articulation section (630) is operable to selectively position end effector (540) at various lateral deflection angles relative to a longitudinal axis defined by outer sheath (532). Articulation section (630) may take a variety of forms. By way of example only, articulation section (630) may be configured in accordance with one or more teachings of U.S. Pub. No. 2012/0078247, issued as U.S. Pat. No. 9,402,682 on Aug. 2, 2016, the disclosure of which is incorporated by reference herein. As another merely illustrative example, articulation section (630) may be configured in accordance with one or more teachings of U.S. Pub. No. 2014/0005701, issued as U.S. Pat. No. 9,393,037 on Jul. 19, 2016 and/or U.S. Pub. No. 2014/0114334, issued as U.S. Pat. No. 9,095,367 on Aug. 4, 2015, the disclosures of which are incorporated by reference herein. Various other suitable forms that articulation section (630) may take will be apparent to those of ordinary skill in the art in view of the teachings herein.

As shown in FIGS. 33-35, shaft assembly (530) further comprises a pair of articulation bands (540, 542) and a pair of translatable rods (640, 642). Articulation bands (540, 542) are configured to operate substantially similar to articulation bands (140, 142, 340, 342) discussed above, except for any differences discussed below. For instance, when articulation bands (540, 542) translate longitudinally in an opposing fashion, this will cause articulation section (530) to bend, thereby laterally deflecting end effector (540) away from the longitudinal axis of shaft assembly (530) from a straight configuration as shown in FIG. 75A to an articulated configuration as shown in FIGS. 75B and 75C. In particular, end effector (540) will be articulated toward the articulation band (540, 542) that is being pulled proximally. During such articulation, the other articulation band (540, 542) may be pulled distally. Alternatively, the other articulation band (540, 542) may be driven distally by an articulation control. Flexible acoustic waveguide (566) is configured to effectively communicate ultrasonic vibrations from waveguide (580) to blade (560) even when articulation section (630) is in an articulated state as shown in FIGS. 75B and 75C.

Translatable members (640, 642) are slidably disposed within the proximal portion of outer sheath (532). Translatable members (640, 642) extend longitudinally through the proximal portion of outer sheath (532) along opposite sides of outer sheath (532) and adjacent an interior surface of outer sheath (532). As best seen in FIG. 35, an elongate recess (644) is formed in an exterior surface of a distal portion of each translatable member (640, 642). Elongate recesses (644) are configured to receive a proximal portion of each articulation band (540, 542). Each translatable member (640, 642) further includes a pin (643) projecting outwardly from an interior surface of each elongate recess (644). An opening (641) formed in a proximal end of each articulation band (640, 642) is configured to receive a respective pin (643) of translatable members (640, 642). Pins (643) and openings (641) thus function to mechanically couple translatable members (640, 642) with articulation bands (540, 542) such that longitudinal translation of translatable member (640) causes concurrent longitudinal translation of articulation band (540), and such that longitudinal translation of translatable member (642) causes concurrent longitudinal translation of articulation band (542).

When translatable members (640, 642) and articulation bands (540, 542) are translated longitudinally in an opposing fashion, a moment is created and applied to a distal end of distal outer sheath (533) in a manner similar to that described above with respect to articulation section (130). This causes articulation section (630) and narrowed section (564) of flexible portion (566) of waveguide (580) to articulate, without transferring axial forces in articulation bands (540, 542) to waveguide (580) as described above. It should be understood that one articulation band (540, 542) may be actively driven distally while the other articulation band (540, 542) is passively permitted to retract proximally. As another merely illustrative example, one articulation band (340, 342) may be actively driven proximally while the other articulation band (540, 542) is passively permitted to advance distally. As yet another merely illustrative example, one articulation band (540, 542) may be actively driven distally while the other articulation band (540, 542) is actively driven proximally. Various suitable ways in which articulation bands (540, 542) may be driven will be apparent to those of ordinary skill in the art in view of the teachings herein.

As shown in FIGS. 33-34, 51-53, 70-72, and 74A-74B, shaft assembly (530) further comprises a rod member (740) slidably disposed within the proximal portion of outer sheath (532). As will be described in more detail below, rod member (740) is operable to translate between a proximal longitudinal position (FIG. 74B) in which rod member (740) is positioned proximally of articulation section (630), and a distal longitudinal position (FIG. 74A) in which rod member (740) extends through articulation section (630) and thereby prevents rigidizes articulation section (740).

Figure 31:
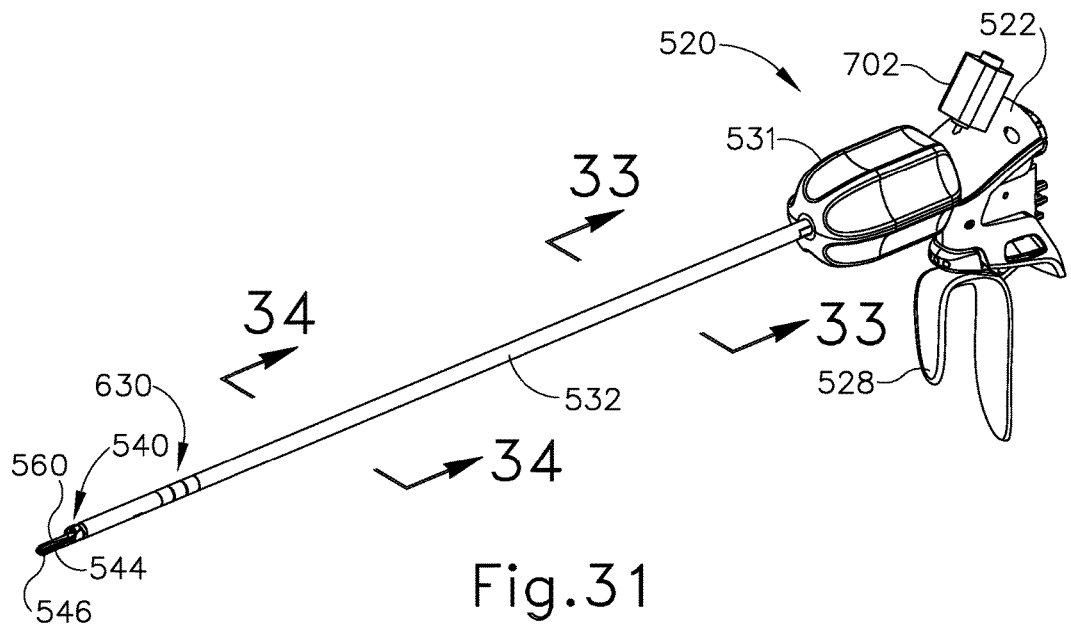
FIG. 31 depicts a perspective view of an exemplary alternative disposable portion that may be used with the reusable portion of the instrument of FIG. 28.
Figure 32:
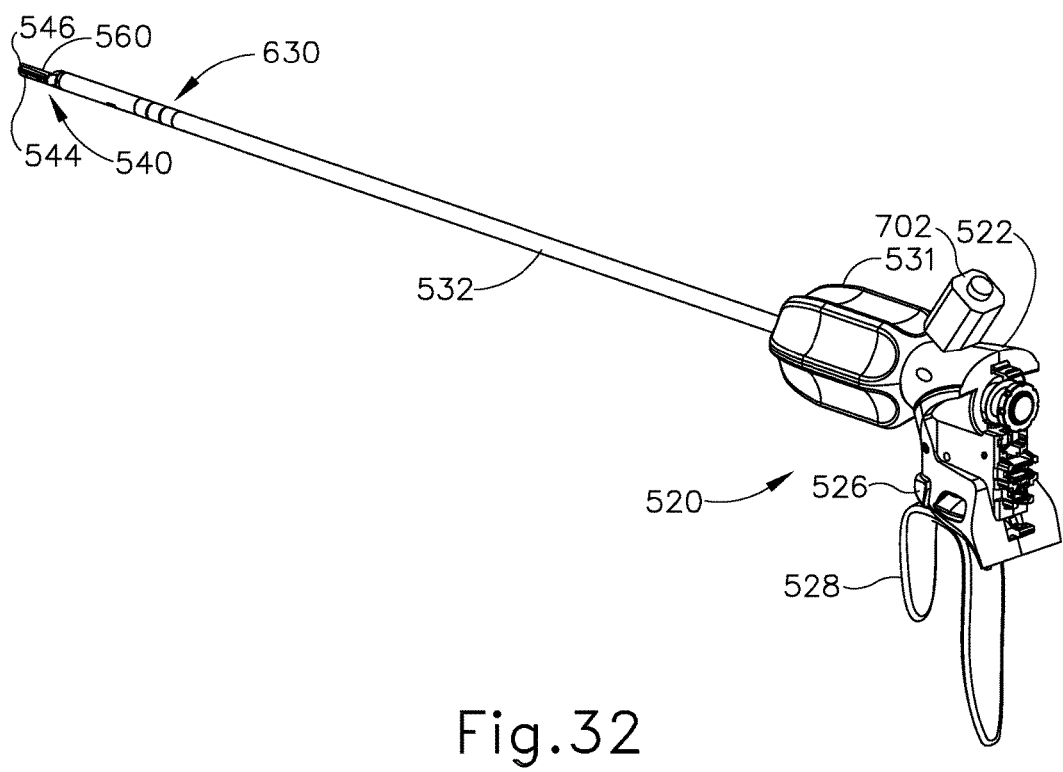
FIG. 32 depicts another perspective view the disposable portion of FIG. 31.
Figure 36:
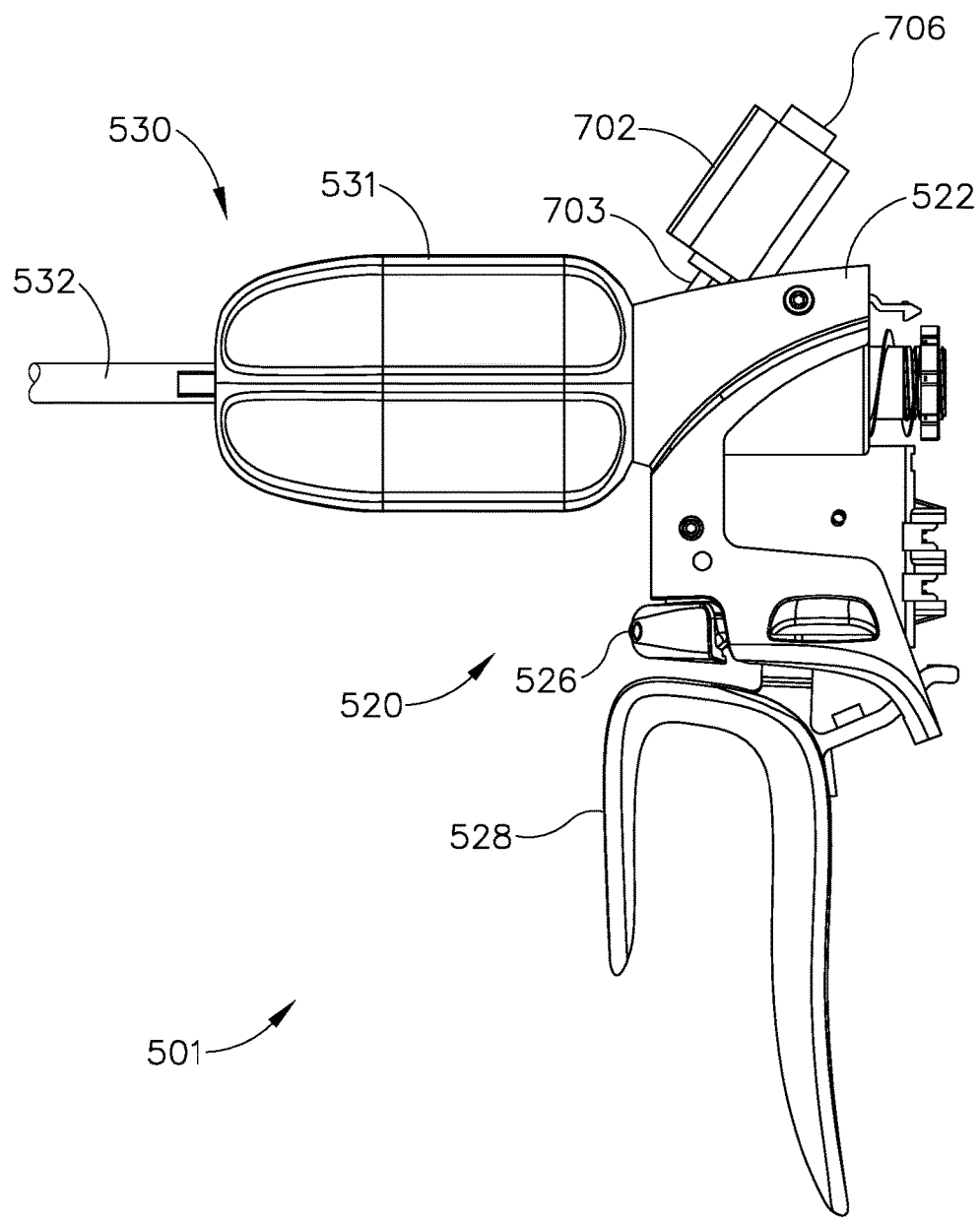
FIG. 36 depicts a side elevational view of a body portion of the disposable portion of FIG. 31.
Figure 37:
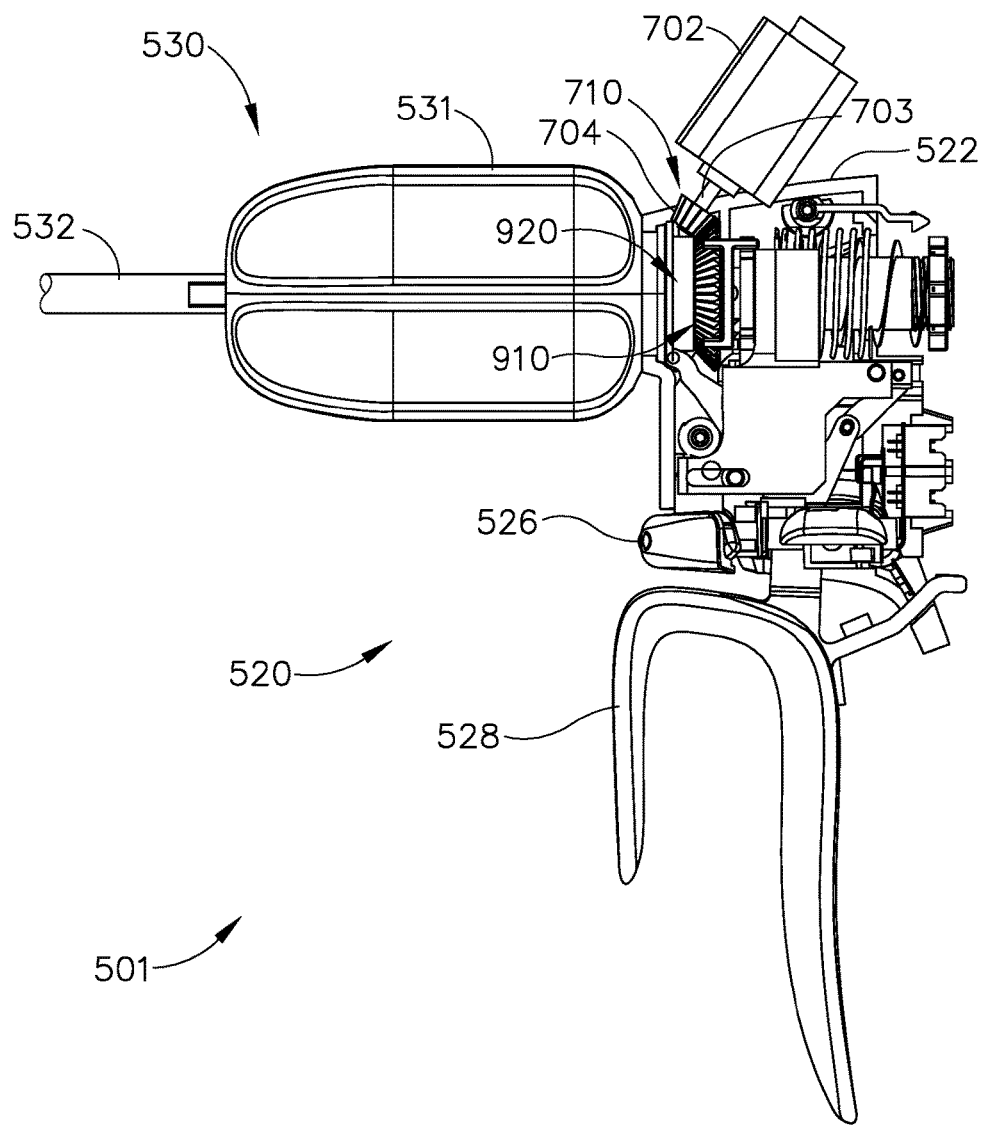
FIG. 37 depicts a side elevational view of the body portion of FIG. 36 with a shrouding half removed.

As shown in FIGS. 31-32, a rotation knob (531) is secured to a proximal portion of proximal outer sheath (532). Rotation knob (531) is rotatable relative to housing (522), such that shaft assembly (530) is rotatable about the longitudinal axis defined by outer sheath (532), relative to body portion (520). Such rotation may provide rotation of end effector (540), articulation section (630), and shaft assembly (530) unitarily. Of course, rotatable features may simply be omitted if desired.

D. Exemplary Articulation Control Assembly

Figure 38:
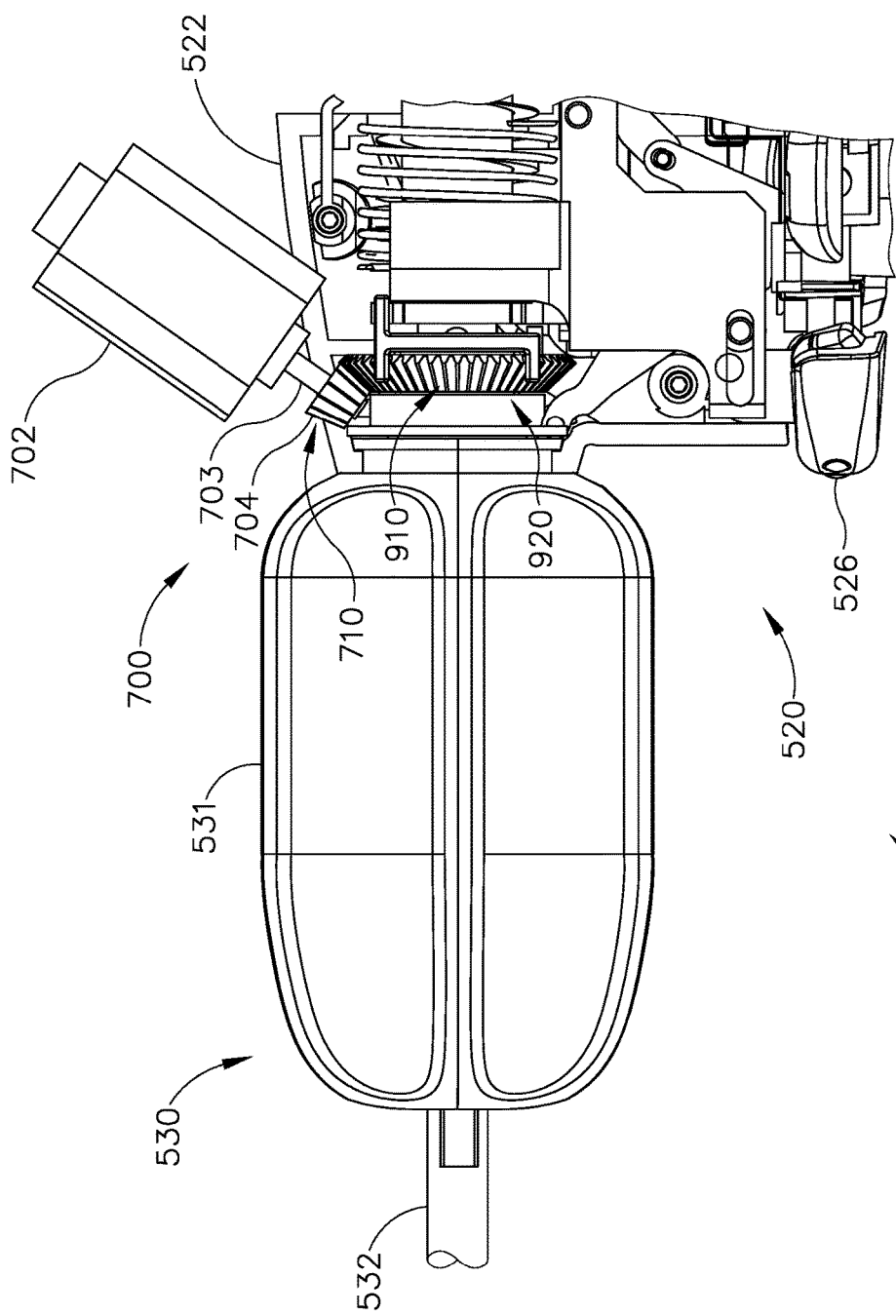
FIG. 38 depicts a detailed side elevational view of the body portion of FIG. 36 with a shrouding half removed.
Figure 39:
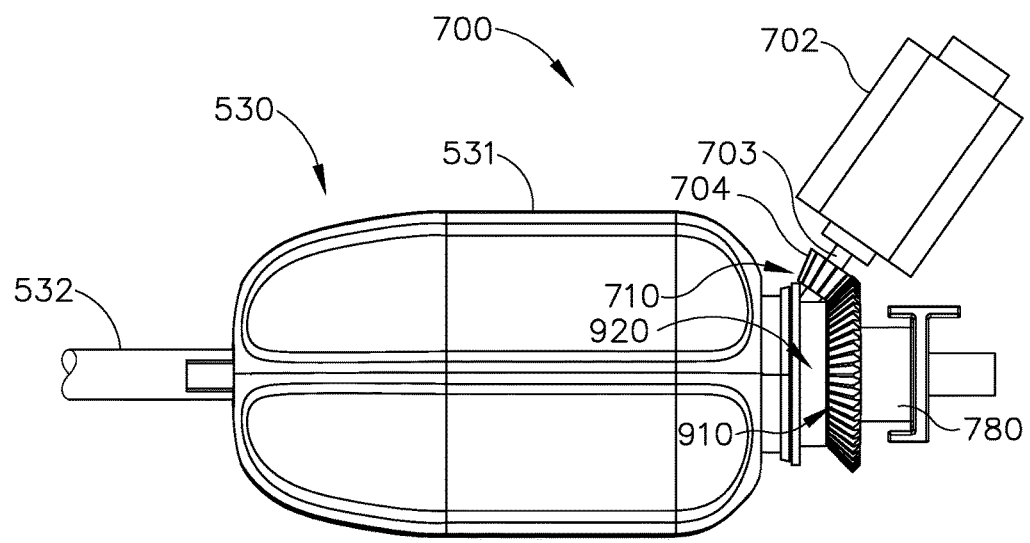
FIG. 39 depicts a side elevational view of an articulation control assembly of the disposable portion of FIG. 31.
Figure 40:
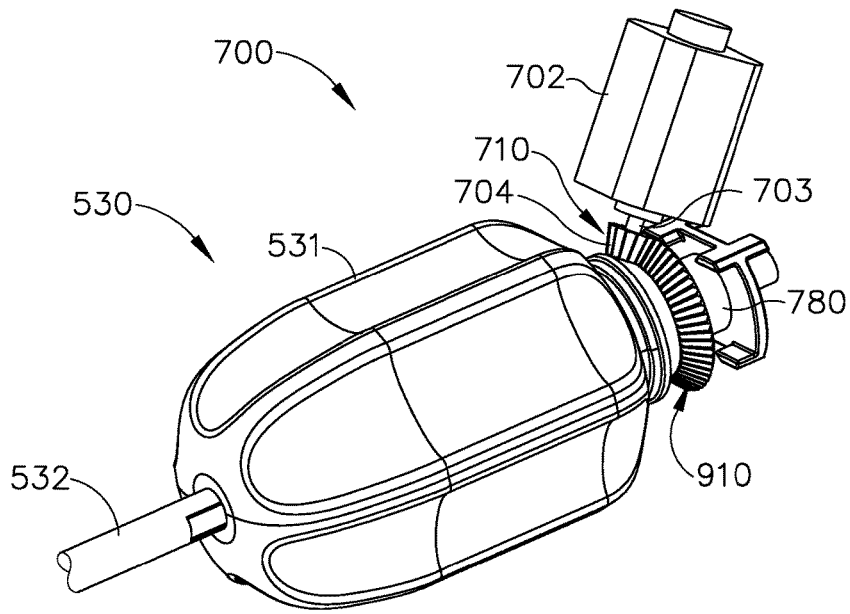
FIG. 40 depicts a perspective view of the articulation control assembly of FIG. 39.

FIGS. 36-75C show the components and operation of an articulation control assembly (700) that is configured to provide control for articulation of articulation section (630). Articulation control assembly (700) of this example comprises a motor (702) and a bevel gear (704). Motor (702) is secured within an upper portion of housing (522) of body portion (520). As best seen in FIG. 38, motor (702) is oriented obliquely relative to shaft assembly (530) such that an axle (703) of motor (702) is configured to rotate about an axis that is oblique to the longitudinal axis defined by shaft assembly (530). Motor (702) comprises a button (706) that is configured to selectively cause motor (702) to rotate axle (703) is a first direction and in a second direction. As best seen in FIG. 38, bevel gear (704) is mechanically coupled with axle (703) of motor (702) such that rotation of axle (703) causes concurrent rotation of bevel gear (704). Bevel gear (704) includes a plurality of teeth (710). As will be described in more detail below, rotation of bevel gear (704) by motor (702) will cause articulation of articulation section (630). In some alternative versions, motor (702) and bevel gear (704) are replaced with a manually rotatable knob and bevel gear similar to knob (402) and bevel gear (404) described above.

Figure 41A:
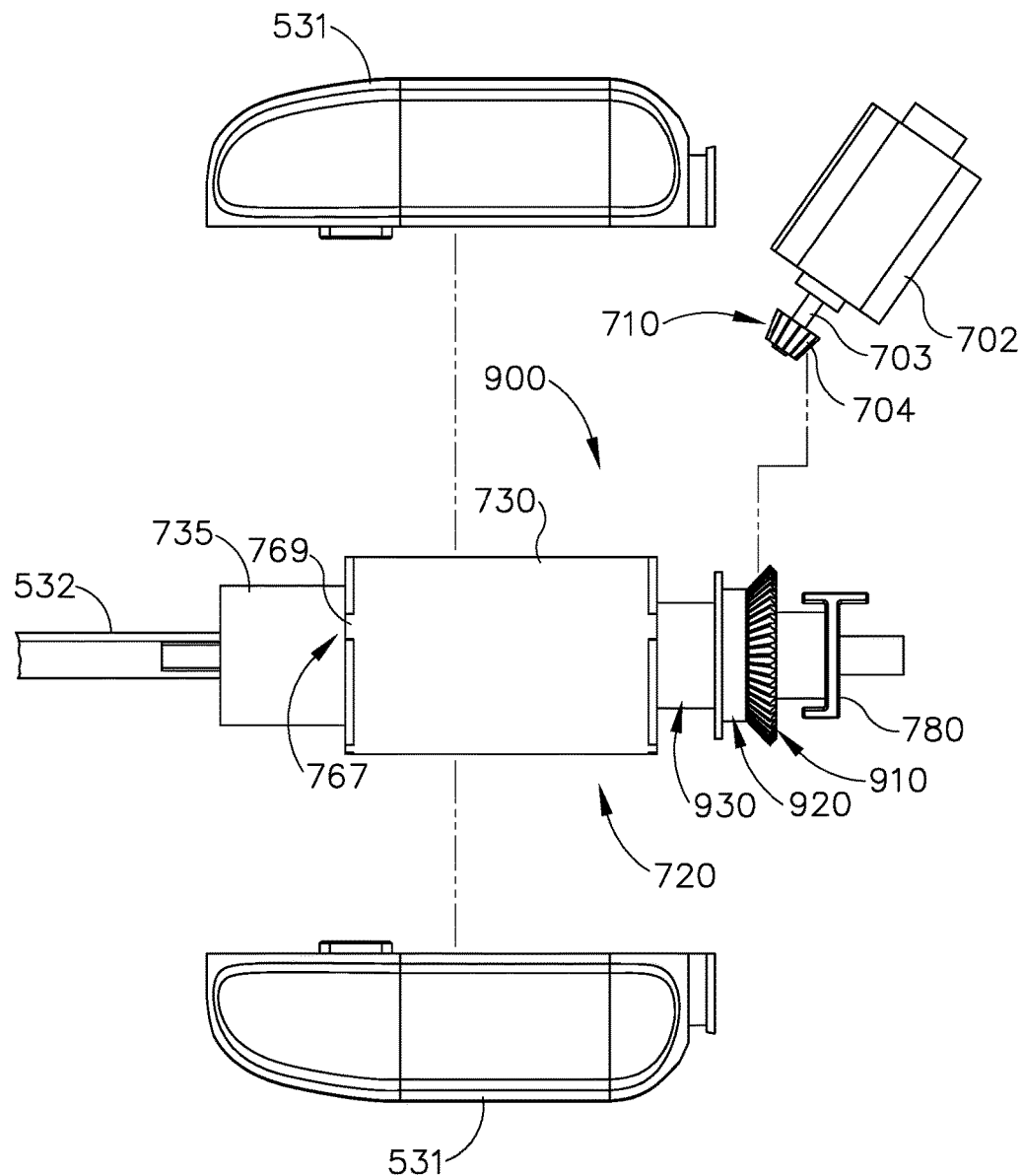
FIG. 41A depicts a partially exploded side elevational view of the articulation control assembly of FIG. 39.
Figure 41B:
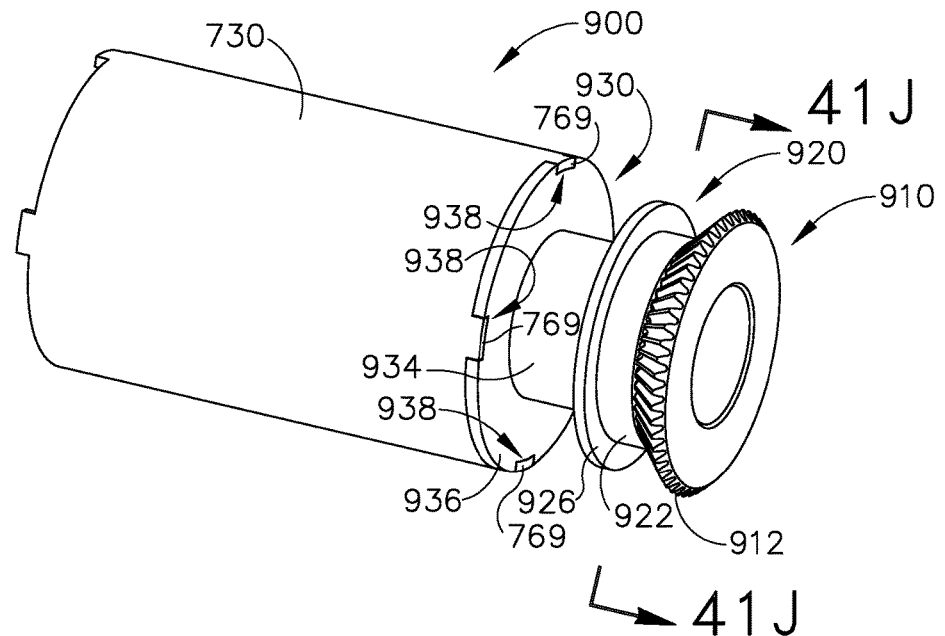
FIG. 41B depicts a perspective view of a gear reduction assembly of the articulation control assembly of FIG. 39.

As best seen in FIG. 41A, articulation control assembly (700) further comprises a drive assembly (720). Drive assembly (720) is secured to a proximal portion of proximal outer sheath (532). Drive assembly (720) is further rotatably disposed within rotation knob (531) such that rotation knob (531) is configured to rotate independently about drive assembly (720) to thereby cause rotation of shaft assembly (530) without causing rotation of drive assembly (720).

Figure 41C:
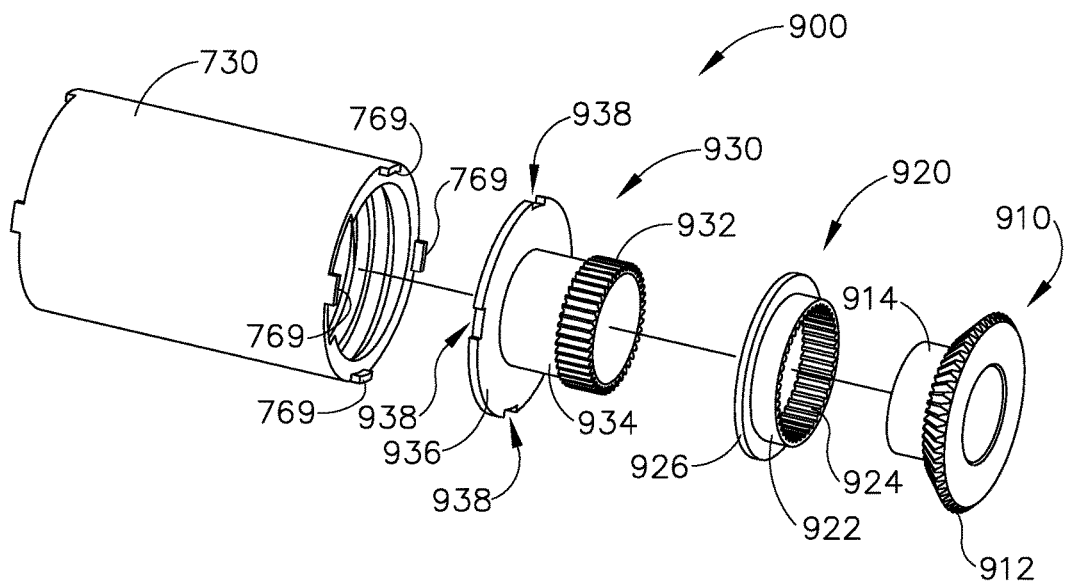
FIG. 41C depicts an exploded perspective view of the gear reduction assembly of FIG. 41B.
Figures 41H, 41I:
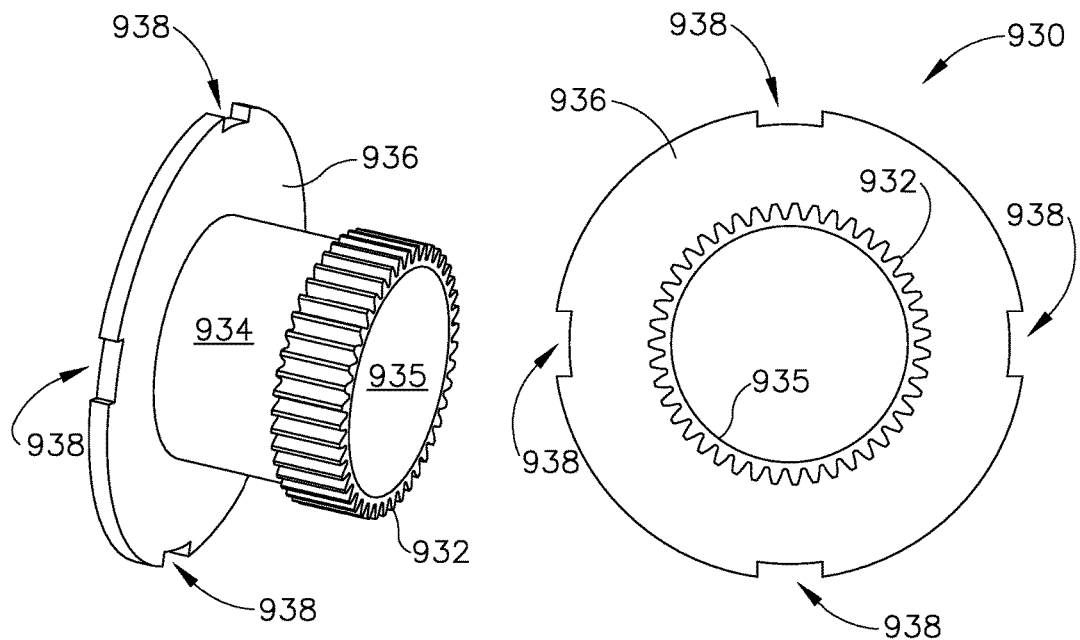
FIG. 41H depicts a perspective view of a flex spline member of the gear reduction assembly of FIG. 41B.
FIG. 41I depicts a rear elevational view of the flex spline member of FIG. 41H.
Figure 41J:
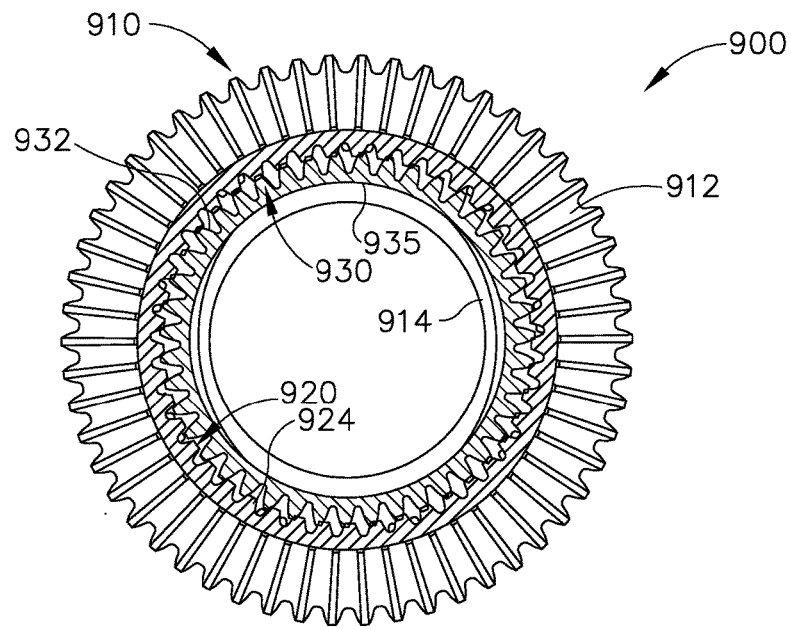
FIG. 41J depicts a cross-sectional view of the gear reduction assembly of FIG. 41B, taken along line 41J-41J of FIG. 41B.
Figure 42:
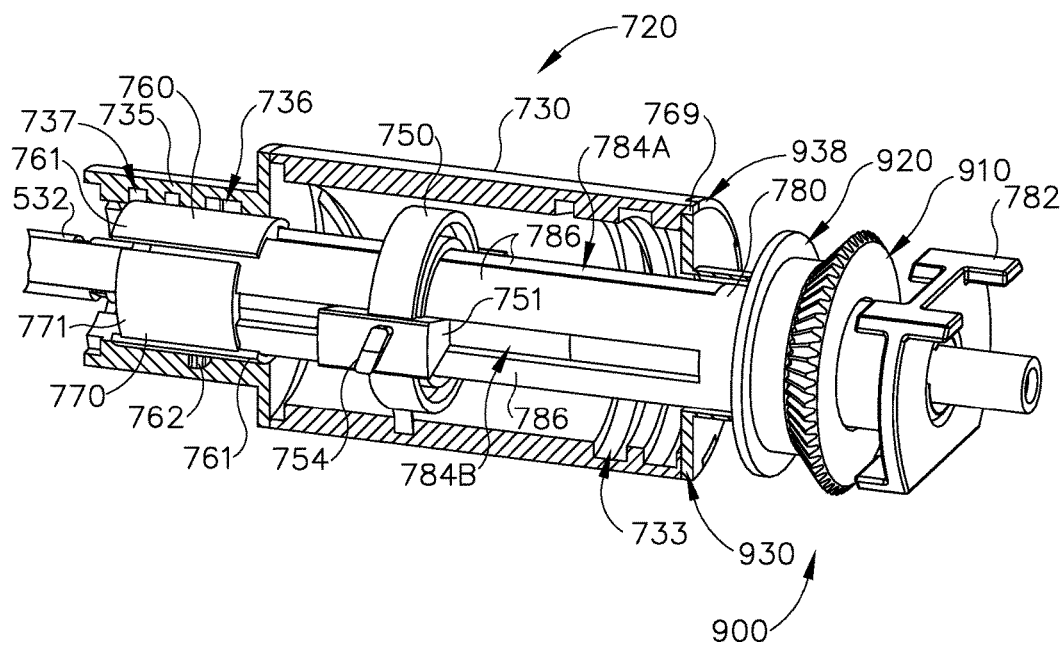
FIG. 42 depicts a partial cross-sectional perspective view of a drive assembly of the articulation control assembly of FIG. 39.

As shown in FIGS. 41A-42, drive assembly (720) comprises a proximal housing (730), a distal housing (735), a plurality of lead screws (750, 760, 770), and a cylindrical guide (780). Distal housing (735) and proximal housing (730) are coupled to one another via a plurality of interlocking tabs (769) and slots (767) such that rotation of proximal housing (730) causes concurrent rotation of distal housing (735). Proximal housing (730) is also coupled with an output flange (936) of a gear reduction assembly (900) through engagement between tabs (769) and slots (938), as will be described in greater detail below, such that rotation of output flange (936) causes concurrent rotation of proximal housing (730). Distal housing (735), proximal housing (730), and gear reduction assembly (900) substantially encompass the internal components of drive assembly (720) as will be described in more detail below.

FIGS. 41B-41J show gear reduction assembly (900) in greater detail. Gear reduction (900) assembly of the present example comprises a bevel gear (910), a fixed spline member (920), and a flex spline member (930). As best seen in FIG. 41C, bevel gear (910), fixed spline member (920), and flex spline member (930) are all coaxially aligned with each other and provide clearance for waveguide (580) and the proximal portions of the rest of shaft assembly (530) to be coaxially disposed therethrough. As best seen in FIGS. 41D-41E, bevel gear (910) comprises an array of bevel gear teeth (912) and an output shaft (914). Bevel gear teeth (912) are configured and positioned to mesh with teeth (710) of bevel gear (704) such that rotation of bevel gear (704) causes concurrent rotation of bevel gear (910). In other words, activation of motor (702) will cause rotation of bevel gear (910). As best seen in FIG. 41E, output shaft (914) has an outer surface with an elliptical profile. This allows output shaft (914) to act as a wave generator within gear reduction assembly (900) as will be described in greater detail below.

FIGS. 41F-41G show fixed spline member (920) in greater detail. Fixed spline member (920) comprises a rigid cylindraceous body (922) with an array of internal teeth (924) and an outwardly extending annular flange (926). Flange (926) is fixedly secured to housing (522) of body portion (520) such that fixed spline member (920) is configured to remain stationary within body portion (520). FIGS. 41H-41I show flex spline member (930) in greater detail. Flex spline member (930) comprises a set external teeth (932) positioned at a proximal end of a cylindraceous body (934). Body (934) is configured to deform radially outwardly yet is also configured to rigidly transfer rotation along the length of body (934). Various suitable materials and configurations that may be used to provide such radial flexing combined with rigid torque transfer will be apparent to those of ordinary skill in the art in view of the teachings herein. Output flange (936) is positioned at the distal end of body (934). As noted above, output flange (936) includes an array of slots (938) that receive tabs (769) of proximal housing (730), such that rotation of flex spline member (930) causes concurrent rotation of proximal housing (730).

As best seen in FIG. 41J, teeth (932) of flex spline member (930) are configured and positioned to mesh with teeth (924) of rigid spline member (920). At any given moment, only some of teeth (932) are engaged with teeth (924). By way of example only, rigid spline member (930) may be configured to have at least two more teeth (924) than flex spline member (930). As also best seen in FIG. 41J, the elliptical outer surface of output shaft (914) of bevel gear (910) bears against the inner surface (935) of body (934) of flex spline member (930). In particular, the elliptical outer surface of output shaft (914) bears against inner surface (935) at the antipodal points of the major axis of the elliptical outer surface of output shaft (914). Thus, as bevel gear (910) is rotated, the points of contact between bevel gear (910) and flex spline member (930) orbit about the central longitudinal axis of gear reduction assembly (900). This causes teeth (932) to engage teeth (924) in orbital paths about the central longitudinal axis of gear reduction assembly (900), with body (934) flexibly deforming to provide this engagement between teeth (924, 932). Rigid spline member (920) remains stationary while flex spline member (930) rotates during such engagement. The rotation of flex spline member (930) provides rotation of proximal housing (730) as noted above. Proximal housing (730) thus rotates in response to rotation of bevel gear (910).

It should be understood from the foregoing that activation of motor (702) will cause rotation of housings (730, 735) via gear reduction assembly (900). It should also be understood that gear reduction assembly (900) provides a strain wave gearing system or harmonic drive system. By way of example only, gear reduction assembly (900) may be further configured and operable in accordance with at least some of the teachings of U.S. Pat. No. 2,906,143, entitled "Strain Wave Gearing," issued Sep. 29, 1959, the disclosure of which is incorporated by reference herein. In the present example, gear reduction assembly (900) provides a gear reduction of approximately 25:1. Alternatively, any other suitable gear reduction may be provided.

As shown in FIGS. 44-47, proximal housing (730) includes internal threading (733) formed in an interior surface of proximal housing (730). As shown in FIGS. 54-58, distal housing (735) includes proximal internal threading 736 formed in an interior surface of distal housing (735); and distal internal threading (737) formed in the interior surface of distal housing (735). Threadings (736, 737) have opposing pitch angles or orientations in this example. In other words, the pitch orientation of threading (736) is opposite to the pitch orientation of threading (737). As should be understood by comparing FIGS. 46, 47, 57, and 58, a proximal portion (733A) of threading (733) of proximal housing (730) has a greater pitch angle than a distal portion (733B) of threading (733) as well as threadings (736, 737) of distal housing (735). As will be described in more detail below, this difference in pitch angles is causes a variance in the speed of longitudinal translation of rod member (740).

Figure 48:
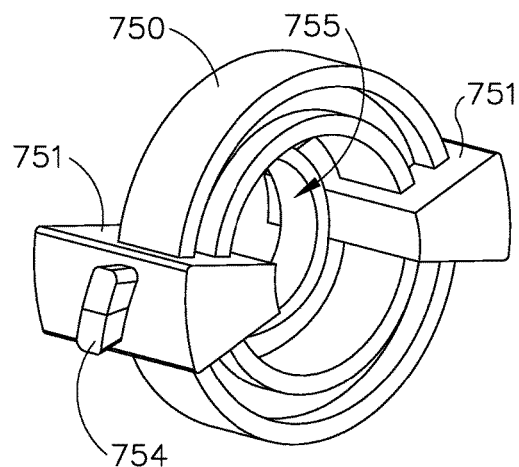
FIG. 48 depicts a perspective view of a lead screw of the drive assembly of FIG. 42.
Figure 49:
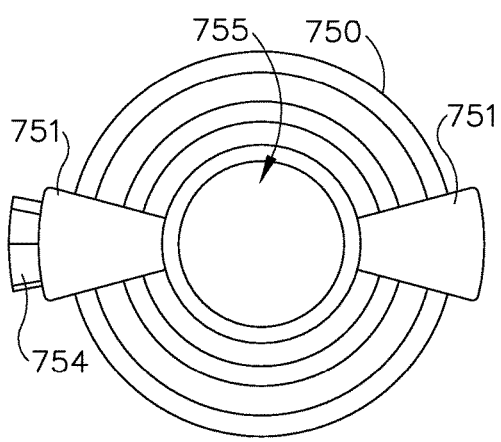
FIG. 49 depicts a front elevational view of the lead screw of FIG. 48.
Figure 50:
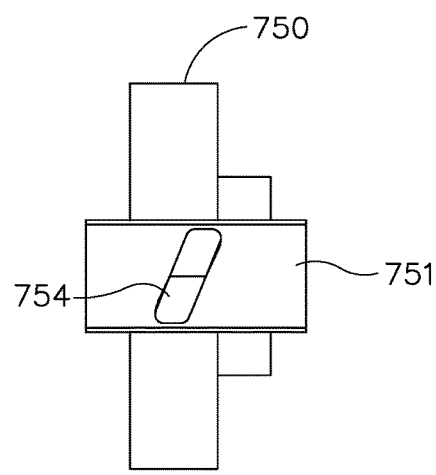
FIG. 50 depicts a side elevational view of the lead screw of FIG. 48.

As shown in FIGS. 48-50, a first lead screw (750) includes a pair of wedge-shaped projections (751) extending outwardly from radially opposing sides of first lead screw (750). First lead screw (750) further includes a discrete exterior thread (754) projecting outwardly from an exterior surface of projection (751). Thread (754) is configured to engage with threading (733) of proximal housing (730). The pitch angle of thread (754) complements the pitch angle of threading (733). As will be described in greater detail below, articulation control assembly (700) is configured to permit lead screw (750) to slide longitudinally within drive assembly (720) yet prevent lead screw (750) from rotating within drive assembly (720). It should therefore be understood that rotation of proximal housing (730) in a first direction will drive lead screw (750) proximally; and rotation of proximal housing (730) in a second direction will drive lead screw (750) distally.

Figures 59, 60:
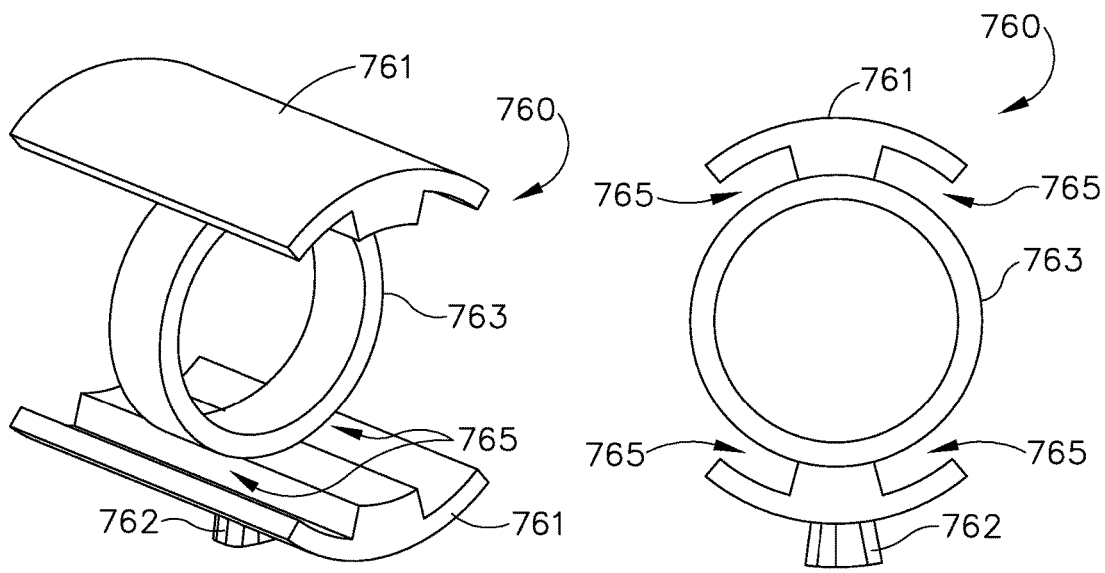
FIG. 59 depicts a perspective view of another lead screw of the drive assembly of FIG. 42.
FIG. 60 depicts a front elevational view of the lead screw of FIG. 59.
Figure 66:
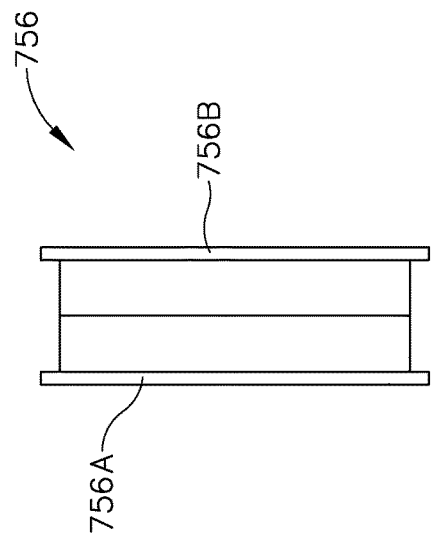
FIG. 66 depicts a side elevational view of the tensioner of FIG. 65.
Figure 68:
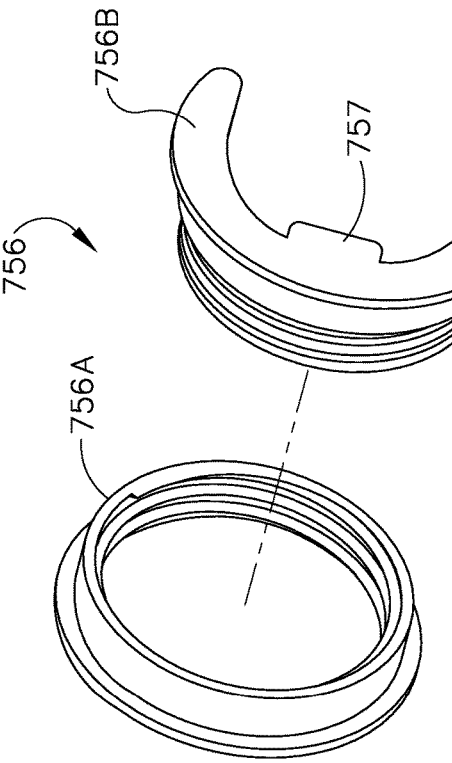
FIG. 68 depicts an exploded perspective view of the tensioner of FIG. 65.
Figure 65:
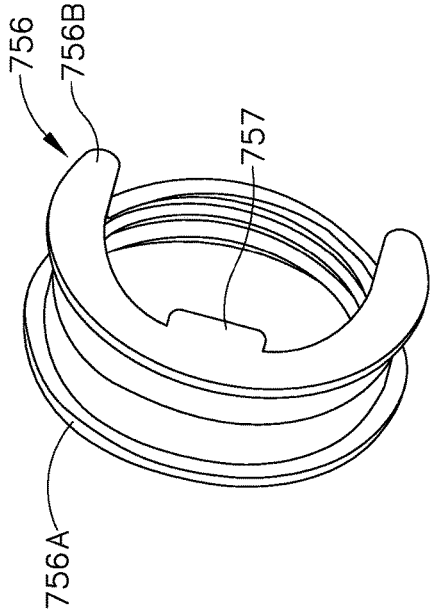
FIG. 65 depicts a perspective view of a tensioner of the drive assembly of FIG. 42.
Figure 67:
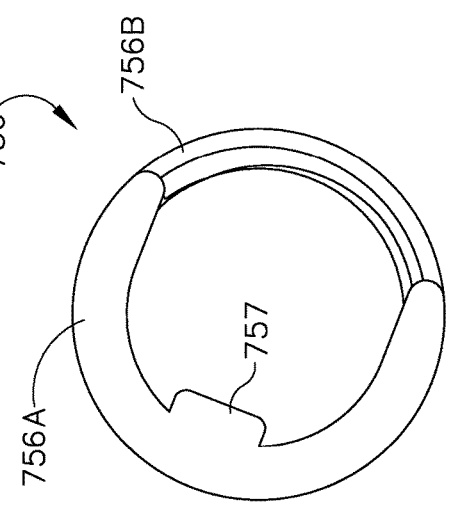
FIG. 67 depicts a front elevational view of the tensioner of FIG. 65.

As shown in FIGS. 59-61, a second lead screw (760) includes a pair of semi-cylindrical flanges (761) extending from radially opposing sides of an annular body (763). Second lead screw (760) further includes a discrete exterior thread (762) projecting outwardly from an exterior surface of flange (761). Thread (762) is configured to engage with proximal internal threading (736) of distal housing (735). As shown in FIGS. 62-64, a third lead screw (770) includes a pair of semi-cylindrical flanges (771) extending from radially opposing sides of an annular body (773). Second lead screw (770) further includes a discrete exterior thread (772) projecting outwardly from an exterior surface of flange (771). Thread (772) is configured to engage with distal internal threading (737) of distal housing (735). The pitch angle of thread (762) complements the pitch angle of threading (736); while the pitch angle of thread (772) complements the pitch angle of threading (737). As will be described in greater detail below, articulation control assembly (700) is configured to permit lead screws (760, 770) to slide longitudinally within drive assembly (720) yet prevent lead screws (760, 770) from rotating within drive assembly (720). It should therefore be understood that, due to the opposing pitch angles of threading (736, 737), rotation of distal housing (735) in a first direction will drive lead screw (760) distally while simultaneously driving lead screw (770) proximally; and rotation of distal housing (735) in a second direction will drive lead screw (760) proximally while simultaneously driving lead screw (770) distally.

Figure 43:
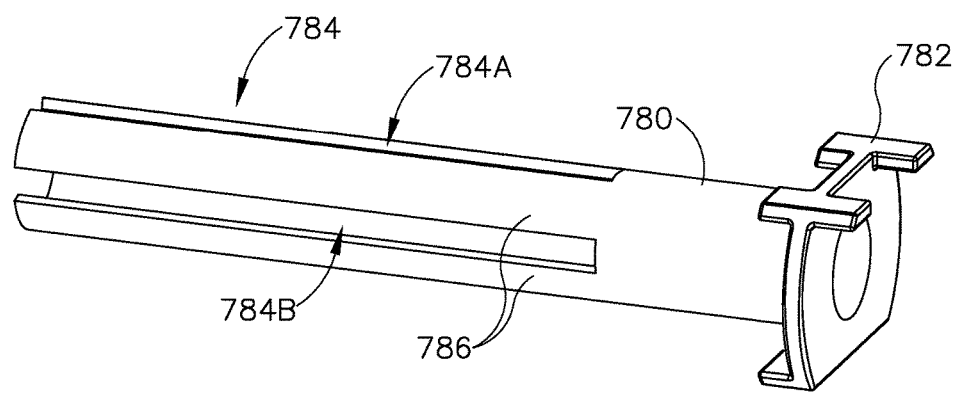
FIG. 43 depicts a perspective view of a cylindrical guide of the drive assembly of FIG. 42.
Figure 44:
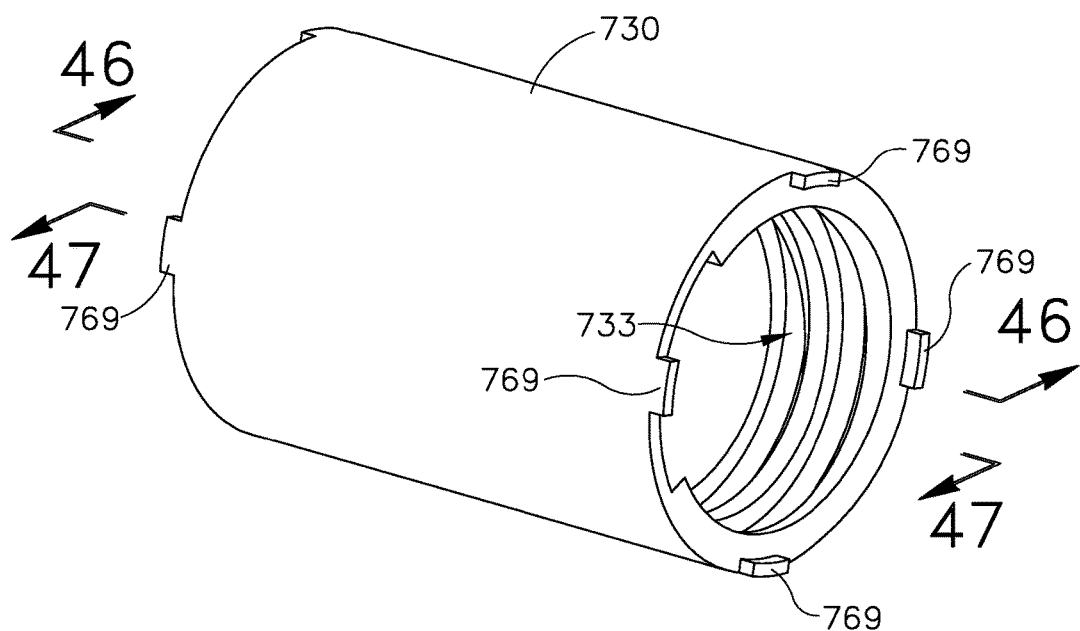
FIG. 44 depicts a perspective view of a proximal rotatable housing of the drive assembly of FIG. 42.
Figure 45:
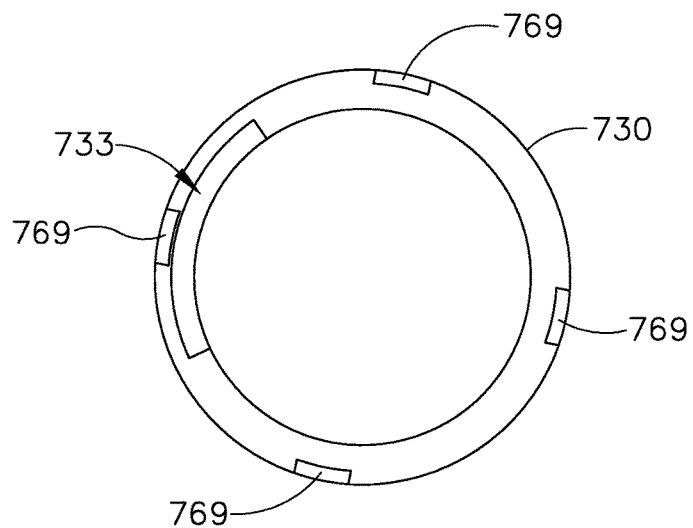
FIG. 45 depicts a front elevational view of the proximal rotatable housing of FIG. 44.
Figure 46:
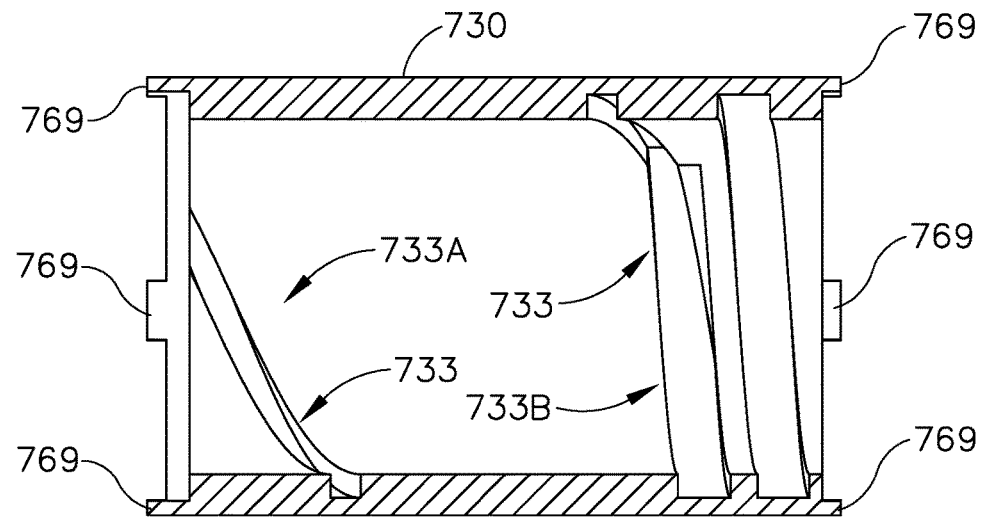
FIG. 46 depicts a cross-sectional side view of the proximal rotatable housing of FIG. 44.
Figure 47:
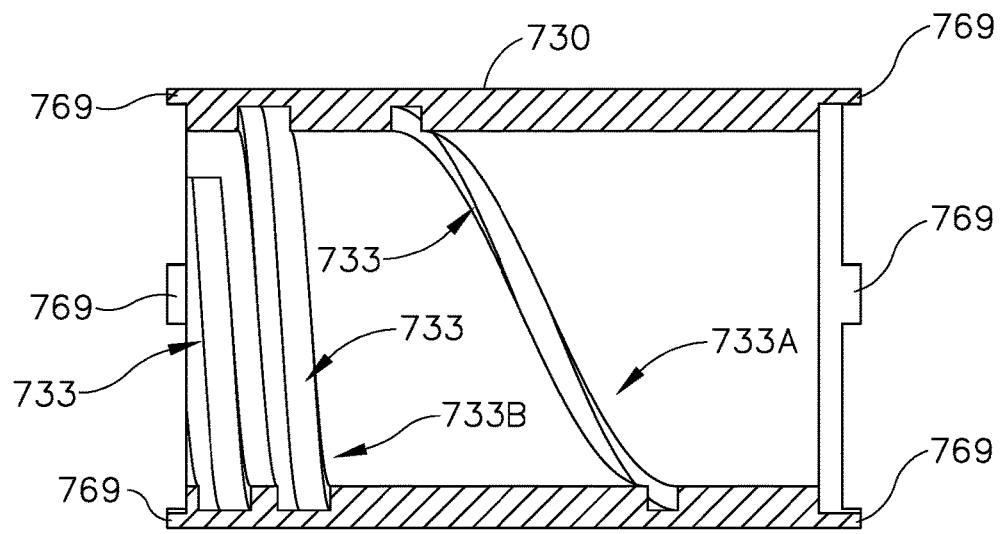
FIG. 47 depicts another cross-sectional side view of the proximal rotatable housing of FIG. 44.

As best seen in FIG. 60, a pair of semi-circular gaps (765) are defined between an interior surface of each flange (761) and an exterior surface of annular body (763) of second lead screw (760). As best seen in FIG. 63, a pair of semi-circular gaps (775) are defined between an interior surface of each flange (771) and an exterior surface of annular body (773) of second lead screw (770). As best seen in FIG. 42, cylindrical guide (780) is positioned within housings (730, 735) about the proximal portion of outer sheath (532). As shown in FIG. 43, a proximal end of cylindrical guide (780) comprises a structural frame (782). Structural frame (782) of cylindrical guide (780) is configured to be fixedly secured within the interior of housing (522) of body portion (520) such that cylindrical guide (780) is configured to remain stationary within body portion (520).

Cylindrical guide (780) comprises a plurality of longitudinal slots (784) formed by a plurality of elongate sidewalls (786) of cylindrical guide (780). In particular, a first pair of longitudinal slots (784A) is formed in radially opposing sides of a sidewall of cylindrical guide (780), and a second pair of longitudinal slots (784B) is formed in radially opposing sides of a sidewall of cylindrical guide (780). As shown in FIG. 25, projections (751) of first lead screw (750) are configured to be received within longitudinal slots (784A) of cylindrical guide (780) such that first lead screw (750) is slidably disposed along longitudinal slots (784A). Thus, lead screw (750) is operable to translate within proximal housing (730) but is prevented from rotating within proximal housing (730).

Figure 70:
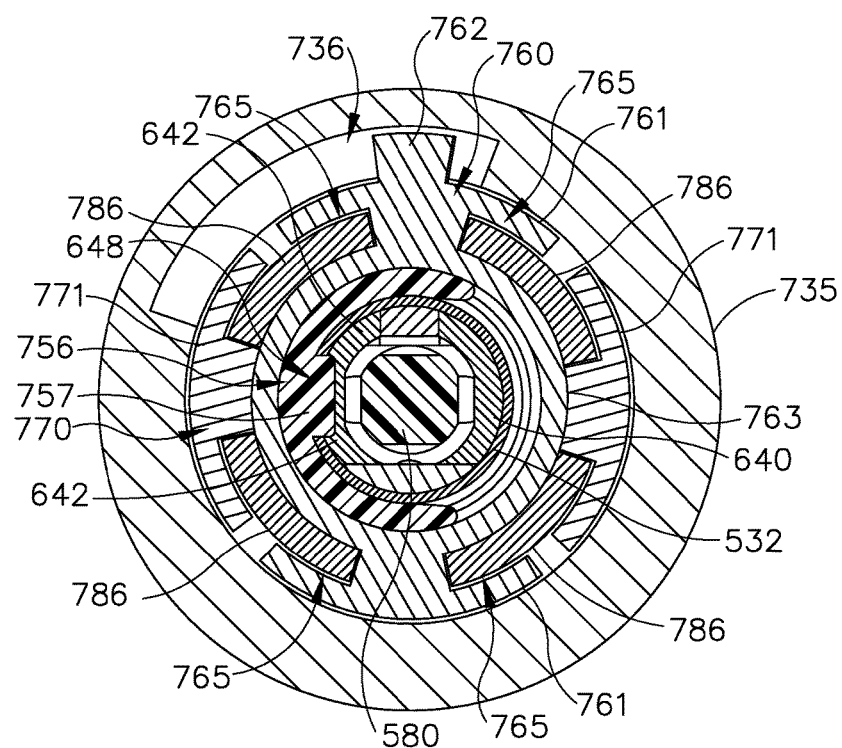
FIG. 70 depicts another cross-sectional rear view of the drive assembly of FIG. 42.
Figure 71:
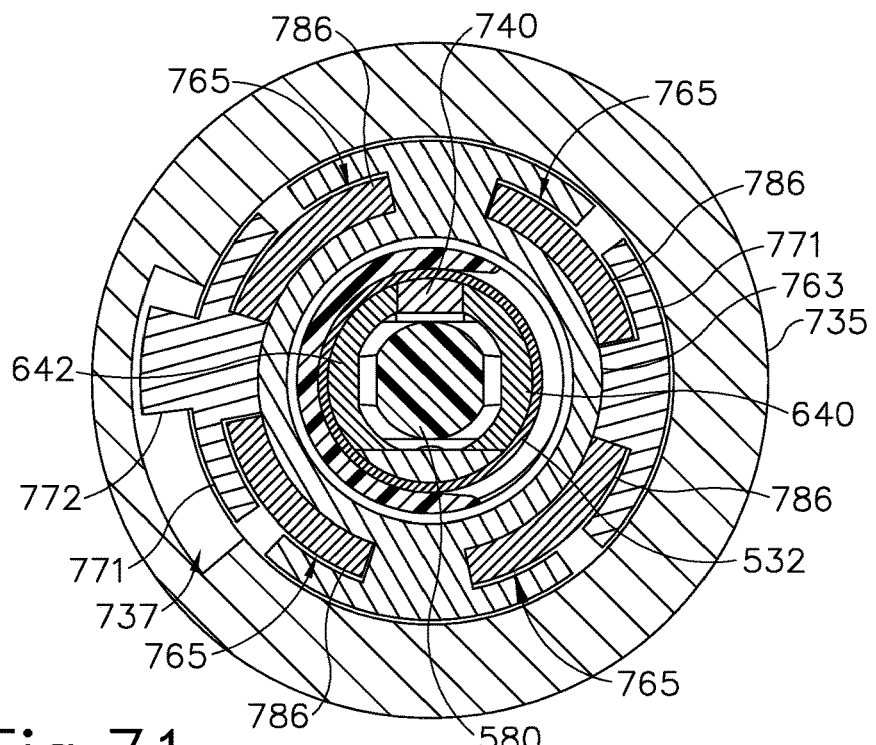
FIG. 71 depicts yet another cross-sectional rear view of the drive assembly of FIG. 42.
Figure 72:
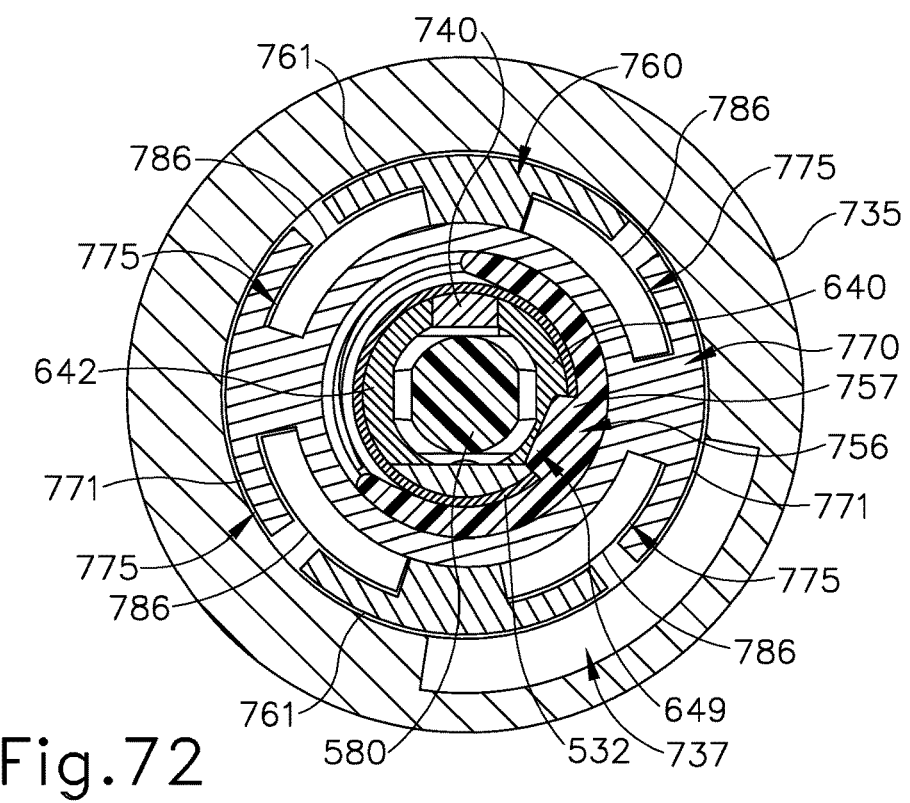
FIG. 72 depicts yet another cross-sectional rear view of the drive assembly of FIG. 42.

As best seen in FIGS. 70 and 71, longitudinal sidewalls (786) of cylindrical guide (780) are configured to be received within gaps (765) of second lead screw (760) such that lead screw (760) is slidably disposed along cylindrical guide (780) within distal housing (735). As best seen in FIG. 72, longitudinal sidewalls (786) of cylindrical guide (780) are configured to be received within gaps (775) of third lead screw (770) such that lead screw (770) is slidably disposed along cylindrical guide (780) within distal housing (735). Thus, lead screws (760, 770) are operable to translate within distal housing (735) but are prevented from rotating within distal housing (735).

Figure 51:
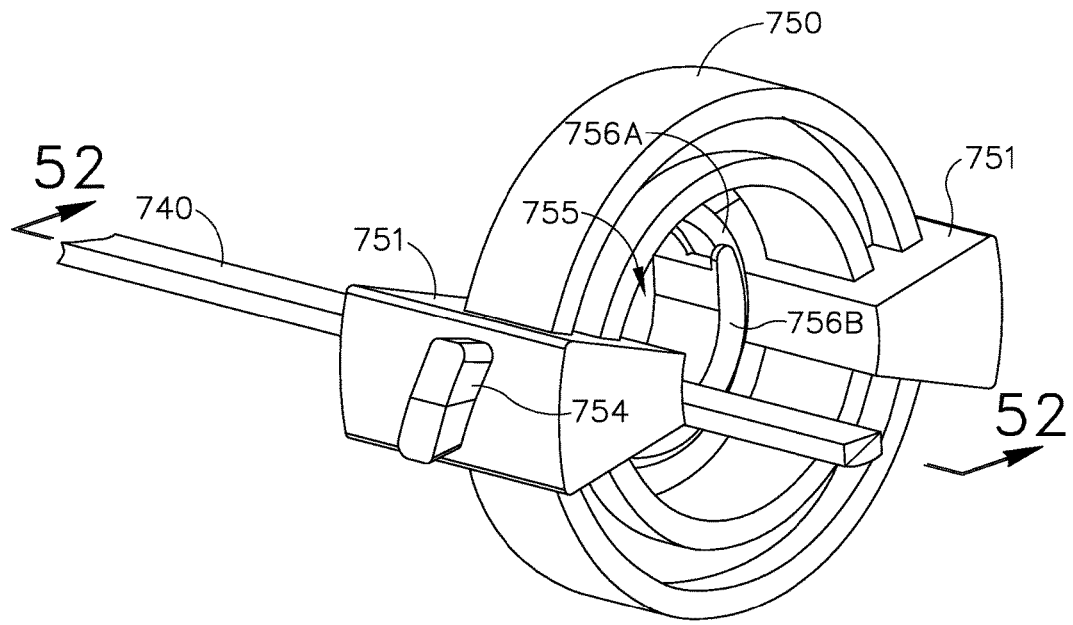
FIG. 51 depicts a perspective view of a translatable assembly of the drive assembly of FIG. 42.
Figure 52:
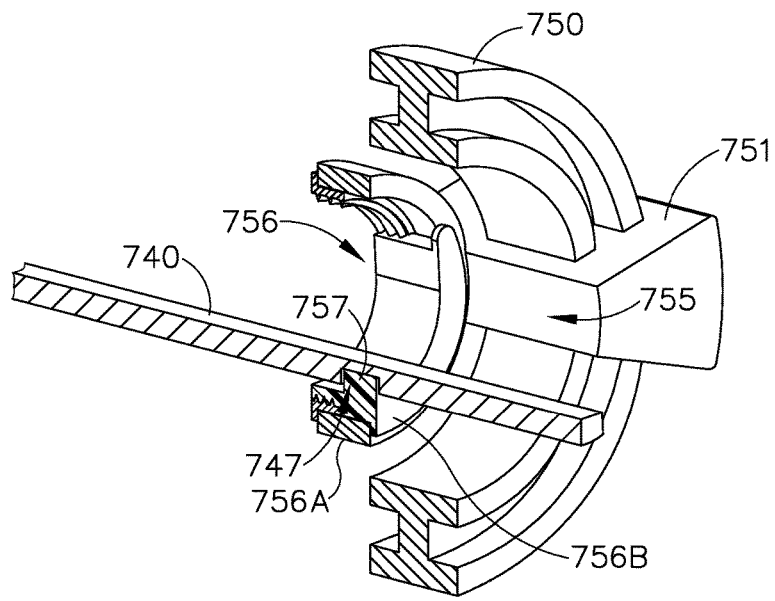
FIG. 52 depicts a cross-sectional perspective view of the translatable assembly of FIG. 51, taken along line 52-52 of FIG. 51.
Figure 54:
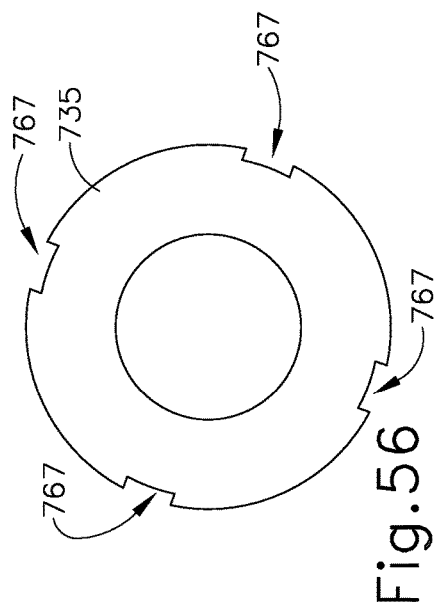
FIG. 54 depicts a perspective view of a distal rotatable housing of the drive assembly of FIG. 42.
Figure 56:
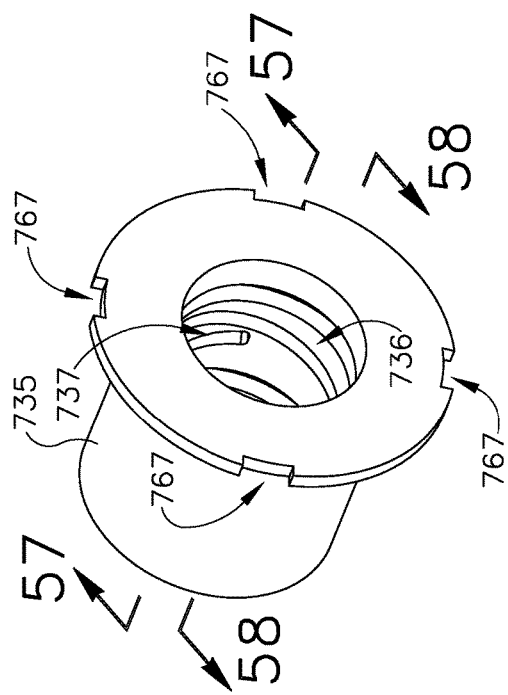
FIG. 56 depicts a front elevational view of the distal rotatable housing of FIG. 54.
Figure 53:
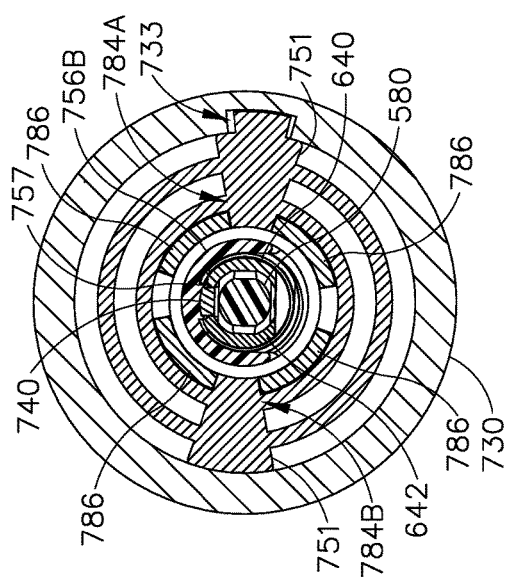
FIG. 53 depicts a cross-sectional rear view of the drive assembly of FIG. 42.
Figure 55:
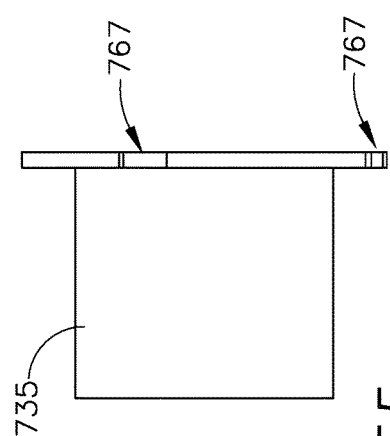
FIG. 55 depicts a side elevational view of the distal rotatable housing of FIG. 54.
Figures 57, 58:
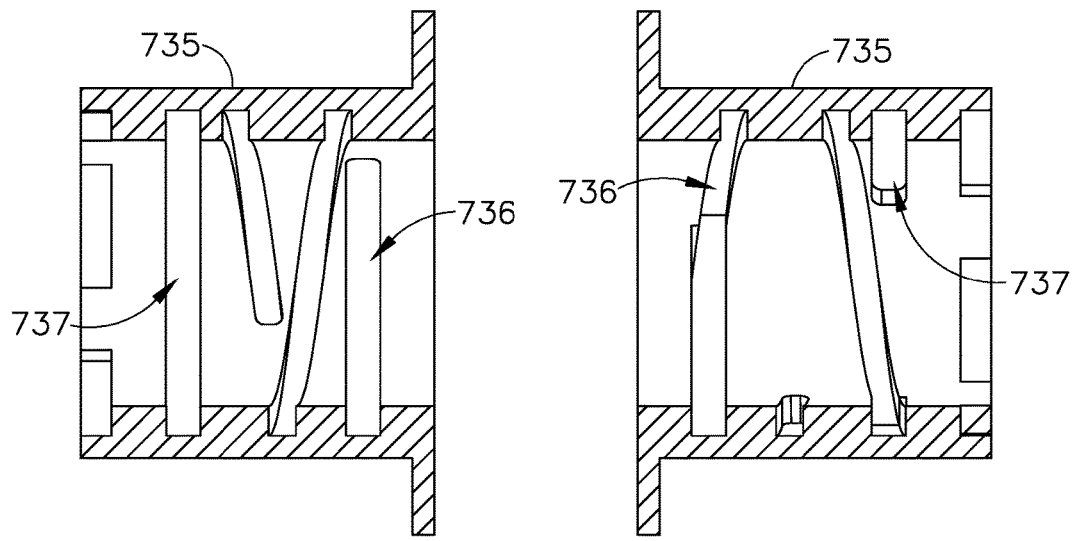
FIG. 57 depicts a cross-sectional side view of the distal rotatable housing of FIG. 54, taken along line 57-57 of FIG. 54.
FIG. 58 depicts another cross-sectional side view of the second rotatable housing of FIG. 54, taken along line 58-58 of FIG. 54.

As shown in FIGS. 51 and 52, first lead screw (750) is secured to a proximal end of rod member (740) via a tensioner (756). As shown in FIGS. 65-68, tensioner (756) includes a first threaded member (756A) and a second threaded member (756B). Threaded members (756A, 756B) threadably engage one another such that a longitudinal position of threaded members (756A, 756B) relative to one another may be changed by rotation of first threaded member (756A) and/or second threaded member (756B). An exterior surface of first threaded member (756A) of tensioner (756) is secured to an interior surface of a throughbore (755) of first lead screw (750) such that longitudinal translation of first lead screw (750) causes concurrent longitudinal translation of tensioner (756). As best seen in FIG. 52, a key (757) of second threaded member (756B) of tensioner (756) is positioned within a mating slot (747) formed in the proximal end of rod member (740) such that longitudinal translation of first lead screw (750) causes current longitudinal translation of rod member (740). Thus, in the present version, first lead screw (750) is operable to both push rod member (740) distally and pull rod member (740) proximally, depending on which direction proximal housing (730) is rotated. Other suitable relationships will be apparent to those of ordinary skill in the art in view of the teachings herein.

Figure 69:
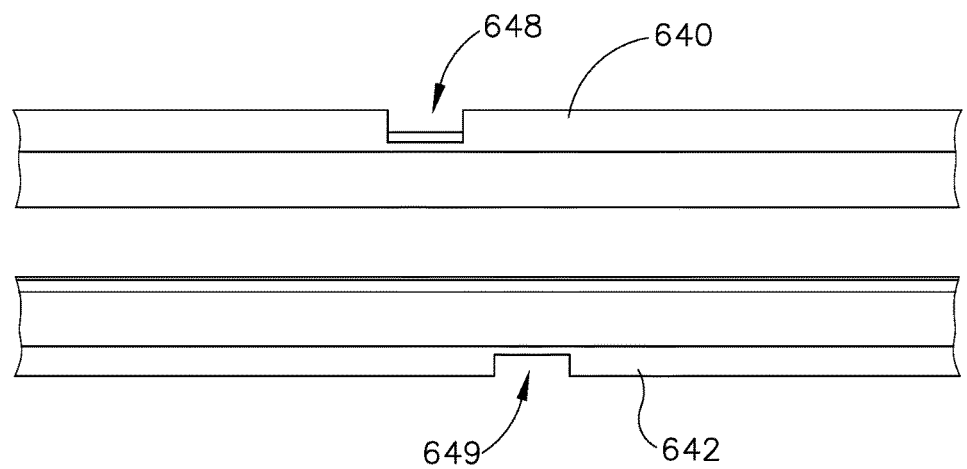
FIG. 69 depicts a top plan view of a proximal end of a pair of translatable rods of the shaft assembly of FIG. 34.

As shown in FIG. 69, a proximal end of each translatable rod (640, 642) includes a slot (648, 649) formed therein. As shown in FIG. 70, second lead screw (760) is secured to a proximal end of translatable rod (642) via a tensioner (756). An exterior surface of a first threaded member (756A) of tensioner (756) is secured to an interior surface of annular body (763) of second lead screw (760) such that longitudinal translation of second lead screw (760) causes concurrent longitudinal translation of tensioner (756). A key (757) of second threaded member (756B) of tensioner (756) is positioned within mating slot (648) of translatable rod (642) such that longitudinal translation of second lead screw (760) causes current translation of translatable rod (642). Thus, in the present version, second lead screw (760) is operable to both push translatable rod (642) distally and pull translatable rod (642) proximally, depending on which direction distal housing (735) is rotated. Because translatable member (642) is mechanically coupled with articulation band (542), it should be understood that second lead screw (760) is operable to both push articulation band (542) distally and pull articulation band (542) proximally, depending on which direction distal housing (735) is rotated. Other suitable relationships will be apparent to those of ordinary skill in the art in view of the teachings herein.

As shown in FIG. 72, third lead screw (770) is secured to a proximal end of translatable rod (640) via a tensioner (756). An exterior surface of a first threaded member (756A) of tensioner (756) is secured to an interior surface of annular body (773) of third lead screw (770) such that longitudinal translation of third lead screw (770) causes concurrent longitudinal translation of tensioner (756). A key (757) of second threaded member (756B) of tensioner (756) is positioned within mating slot (649) of translatable rod (640) such that longitudinal translation of third lead screw (770) causes current translation of translatable rod (640). Thus, in the present version, third lead screw (770) is operable to both push translatable rod (640) distally and pull translatable rod (640) proximally, depending on which direction distal housing (735) is rotated. Because translatable member (640) are mechanically coupled with articulation band (540), it should be understood that second lead screw (760) is operable to both push articulation band (540) distally and pull articulation band (540) proximally, depending on which direction distal housing (735) is rotated. Other suitable relationships will be apparent to those of ordinary skill in the art in view of the teachings herein.

Figure 73A:
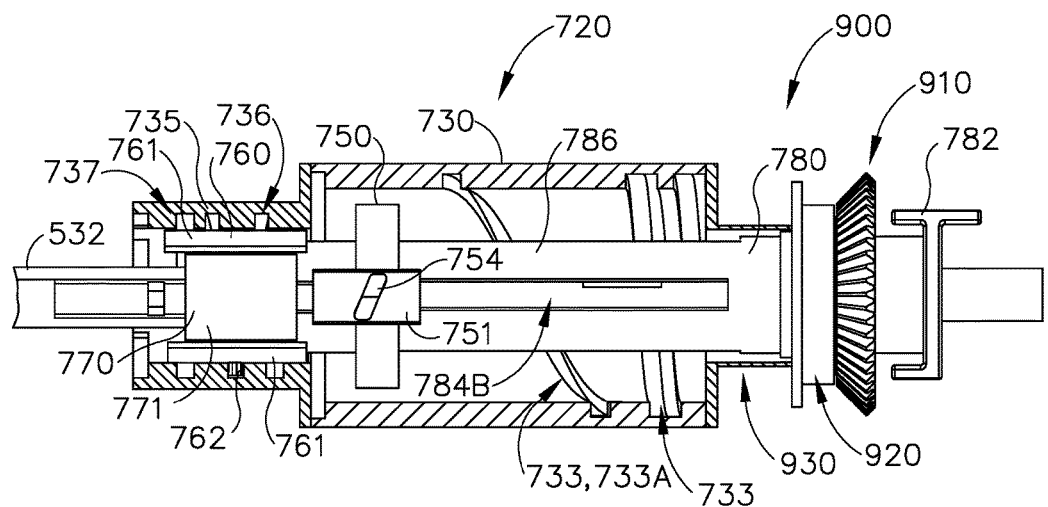
FIG. 73A depicts a partial cross-sectional side view of the drive assembly of FIG. 42, with the lead screw of FIG. 48 in a first longitudinal position, with the lead screw of FIG. 59 in a first longitudinal position, and with the lead screw of FIG. 62 in a first longitudinal position.
Figure 73B:
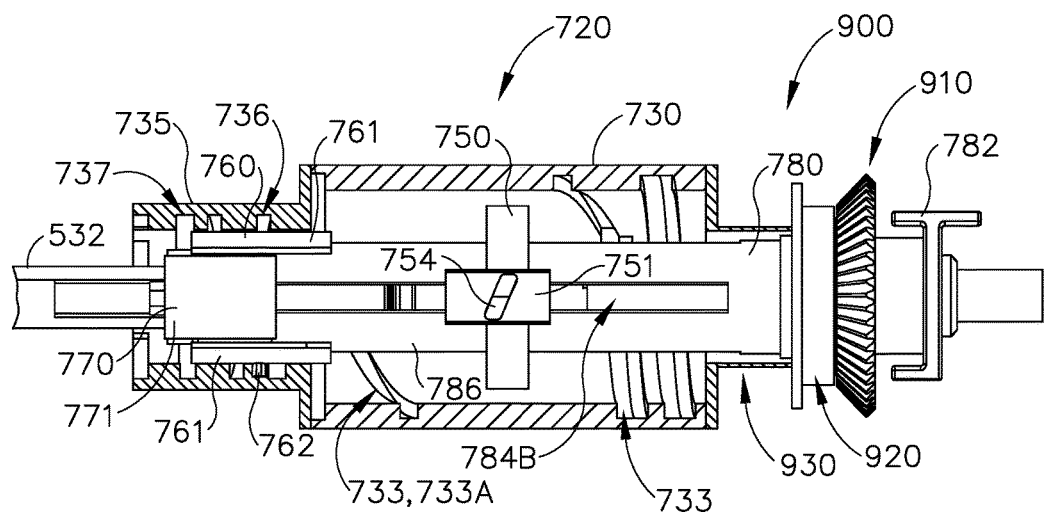
FIG. 73B depicts a partial cross-sectional side view of the drive assembly of FIG. 42, with the lead screw of FIG. 48 moved to a second longitudinal position, with the lead screw of FIG. 59 moved to a second longitudinal position, and with the lead screw of FIG. 62 moved to a second longitudinal position.
Figure 73C:
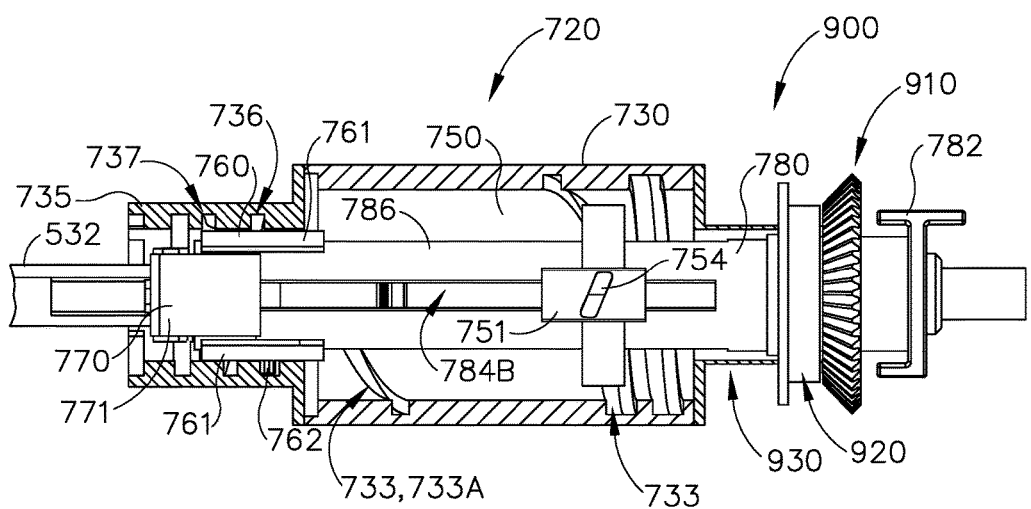
FIG. 73C depicts a partial cross-sectional side view of the drive assembly of FIG. 42, with the lead screw of FIG. 48 moved to a third longitudinal position, with the lead screw of FIG. 59 moved to a third longitudinal position, and with the lead screw of FIG. 62 moved to a third longitudinal position.
Figure 74A:
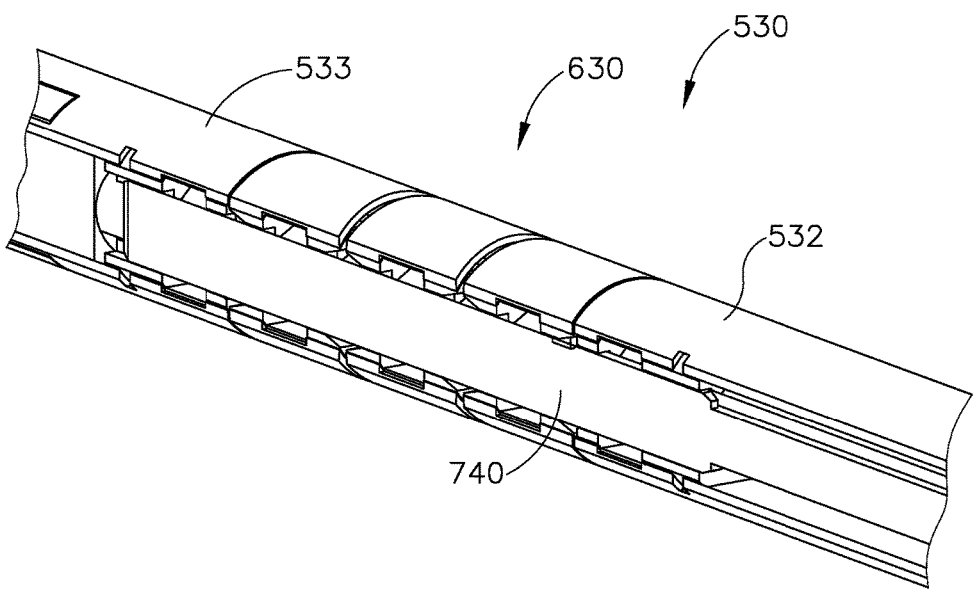
FIG. 74A depicts a cross-sectional perspective view of the shaft assembly of FIG. 34, with a rod member in a first longitudinal position.
Figure 76:
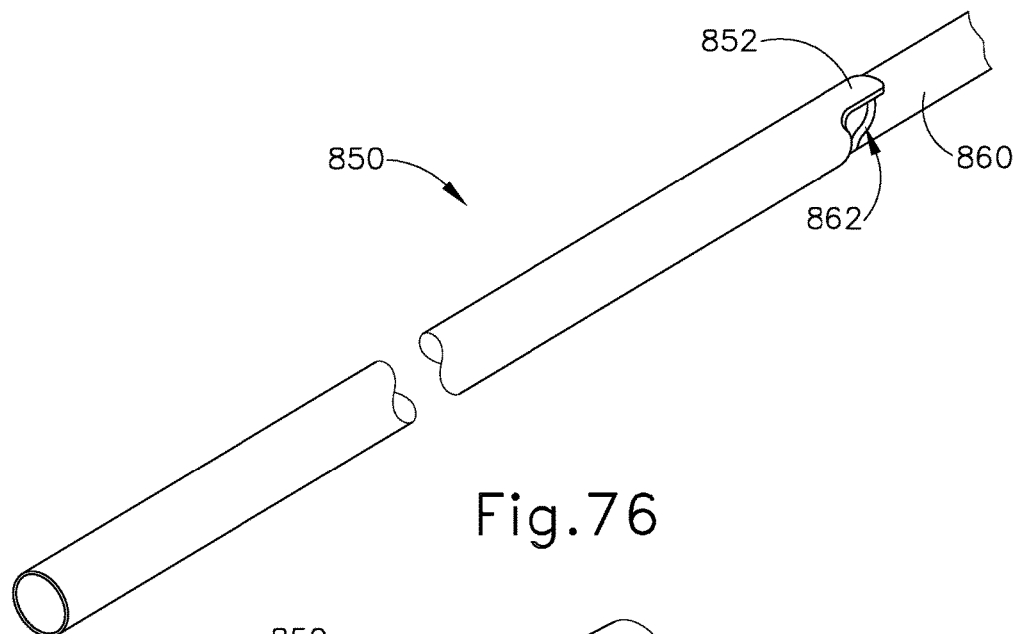
FIG. 76 depicts a perspective view of a stiffening assembly that may be used with the ultrasonic surgical instruments of FIGS. 1, 11, and 28.

FIGS. 73A-75C show several of the above described components interacting to bend articulation section (630) to articulate end effector (540). FIGS. 73A, 74A, and 75A correspond to one another. In FIG. 74A, rod member (740) is in the distal longitudinal position and thereby rigidizes articulation section (730). In FIG. 75A, articulation section (630) is in a substantially straight configuration. Then, housings (730, 735) are rotated by motor (702) via gear reduction assembly (900). The rotation of housings (730, 735) causes first lead screw (750) to translate proximally within proximal housing (730), second lead screw (760) to translate distally within distal housing (735), and third lead screw (770) to advance proximally within distal housing (735). This proximal translation of first lead screw (750) is caused by rotation of first lead screw (750) within proximal portion (733A) of threading (733). As discussed above, the greater pitch angle of proximal portion (733A) causes a greater rate of translation of first lead screw (750) as compared with the translation rate of lead screws (760, 770), as will be understood by comparing FIGS. 73A-73C. The proximal translation of first lead screw (750) pulls rod member (740) proximally in to the proximal longitudinal position as shown in FIG. 74B.

The proximal translation of third lead screw (770) pulls articulation band (540) proximally via translatable rod (640), which causes articulation section (630) to start bending as shown in FIG. 75B. This bending of articulation section (630) pulls articulation band (542) distally. The distal advancement of second lead screw (760) in response to rotation of distal housing (735) enables articulation band (542) and translatable rod (642) to advance distally. In some other versions, the distal advancement of second lead screw (760) actively drives translatable rod (642) and articulation band (542) distally. As the operator continues rotating housings (730, 735) via motor (702) and gear reduction assembly (900), the above described interactions continue in the same fashion, resulting in further bending of articulation section (630) as shown in FIG. 75C. It should be understood that rotating housings (730, 735) in the opposite direction will cause articulation section (630) return to the straight configuration shown in FIG. 75A; and rod member (740) to return to the distal longitudinal position to thereby rigidize the straightened articulation section (730).

The angles of threading (733, 736, 737, 754, 762, 772) are configured such that articulation section (630) will be effectively locked in any given articulated position, such that transverse loads on end effector (540) will generally not bend articulation section (630), due to friction between threading (733, 736, 737, 754, 762, 772). In other words, articulation section (630) will only change its configuration when housings (730, 735) are rotated. While the angles of threading may substantially prevent bending of articulation section (630) in response to transverse loads on end effector (540), the angles may still provide ready rotation of housings (730, 735) to translate lead screws (750, 760, 770). By way of example only, the angles of threading (733, 736, 737, 754, 762, 772) may be approximately +/−2 degrees or approximately +/−3 degrees. Other suitable angles will be apparent to those of ordinary skill in the art in view of the teachings herein. It should also be understood that threading (733, 736, 737, 754, 762, 772) may have a square or rectangular cross-section or any other suitable configuration.

In some versions, housings (730, 735) include a visual indicator that is associated with articulation section (630) being in a substantially straight configuration. Such a visual indicator may align with a corresponding visual indicator on rotation knob (531) and/or body (822) of body portion (520). Thus, when an operator has rotated housings (730, 735) to make articulation section (630) approach a substantially straight configuration, the operator may observe such indicators to confirm whether articulation section (630) has in fact reached a substantially straight configuration. By way of example only, this may be done right before instrument (500) is withdrawn from a trocar to reduce the likelihood of articulation section (630) snagging on a distal edge of the trocar. Of course, such indicators are merely optional.

E. Exemplary Alternative Rigidizing Features

FIGS. 76-80A show components of an exemplary alternative shaft assembly (830) comprising an elongate tube member (850) and a tubular guide member (860) that may be readily incorporated into instrument (10, 200) in order to selectively rigidize articulation section (130, 330) when articulation section (130, 330) is in a straight, non-articulated configuration. Tube member (850) and guide member (860) may also be incorporated into instrument (500) as a substitute for rod member (740) and associated components to selectively rigidize articulation section (630) when articulation section (630) is in a straight, non-articulated configuration. In the present example, tube member (850) and guide member (860) are shown as selectively rigidizing an articulation section (831), which may otherwise be configured and operable just like articulation sections (130, 330, 630) described above.

Figure 77:
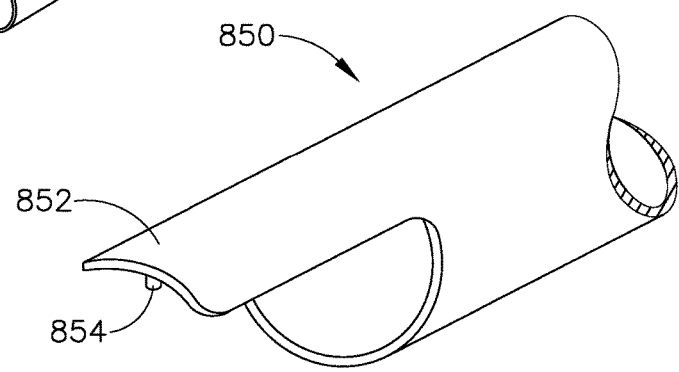
FIG. 77 depicts a detailed perspective view of a proximal end of a tubular member of the stiffening assembly of FIG. 76.

Elongate tube member (850) of the present example comprises a semi-circular tongue (852) extending proximally from a proximal end of elongate tube member (850). As best seen in FIG. 77, tongue (852) includes a pawl (854) projecting inwardly and downwardly from an interior surface of tongue (852). As will be described in more detail below, elongate tube member (850) is longitudinally translatable along a length of shaft assembly (830) between a distal longitudinal position (FIGS. 79A and 80A) and a proximal longitudinal position (FIGS. 79C and 80C). In the distal position, elongate tube member (850) is positioned about articulation section (831) to thereby rigidize articulation section (831). In the proximal position, elongate tube member (850) is located proximally of articulation section (831) and thereby permits articulation of articulation section (831). Elongate tube member (850) of the present example is resiliently biased distally toward the distal longitudinal position. Various suitable ways in which elongate tube member (850) may be biased distally toward the distal longitudinal position will be apparent to those of ordinary skill in the art in view of the teachings herein.

Figure 78:
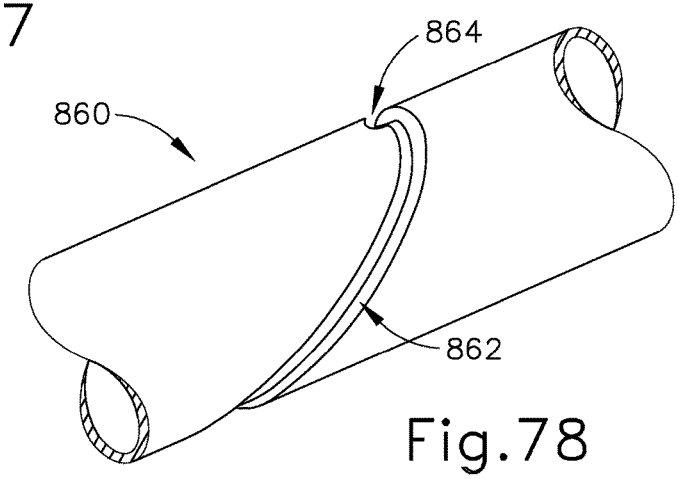
FIG. 78 depicts a detailed perspective view of a tubular guide of the stiffening assembly of FIG. 76.

Elongate tube member (850) is configured to slidably and rotatably receive tubular guide member (860) such that elongate tube member (850) is operable to translate along a length of tubular guide member (860) and such that tubular guide member (860) is operable to rotate within elongate tube member (850). However, while elongate tube member (850) is configured to translate along a length of tubular guide member (860), elongate tube member (850) is not configured to rotate about tubular guide member (860). In other words, elongate tube member (850) is configured to remain in a single rotational position. As shown in FIG. 78, tubular guide member (860) includes an oval-shaped cam channel (862) that is formed in a sidewall of tubular guide member (860). Cam channel (862) is oriented obliquely relative to the longitudinal axis of tubular guide member (860). Cam channel (862) is configured to slidably receive pawl (854) of elongate tube member (850). As will be described in more detail below, pawl (854) serves as a cam follower such that rotation of tubular guide member (860) within elongate tube member (850) causes translation of elongate tube member (850) as pawl (854) translates within cam channel (862) of tubular guide member (860). As best seen in FIG. 78, a proximal portion (862A) of cam channel (862) comprises a detent (864) formed in distal interior surface of cam channel (862). As will be described in more detail below, detent (864) is configured to receive pawl (854) to selectively maintain the position of pawl (854) within oval-shaped cam channel (862).

Figure 79A:
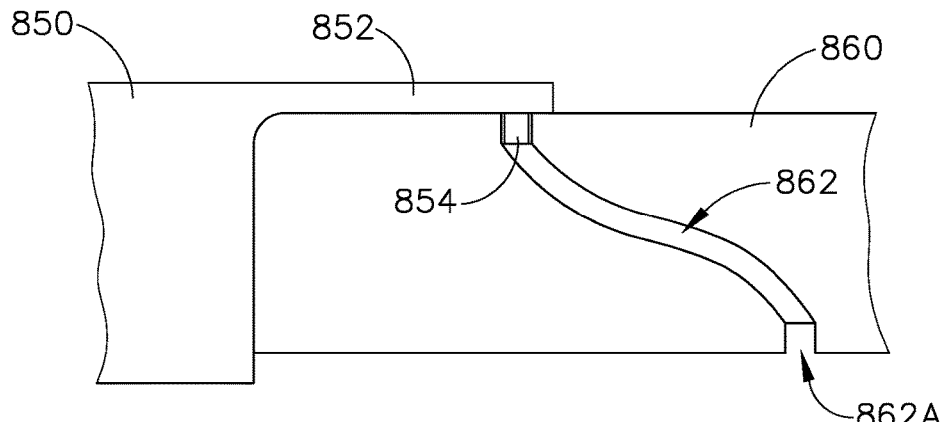
FIG. 79A depicts a detailed side elevational view of the tubular member of FIG. 77 coupled with the tubular guide of FIG. 78, with the tubular member in a first longitudinal position, and with the tubular guide in a first rotational position.
Figure 79B:
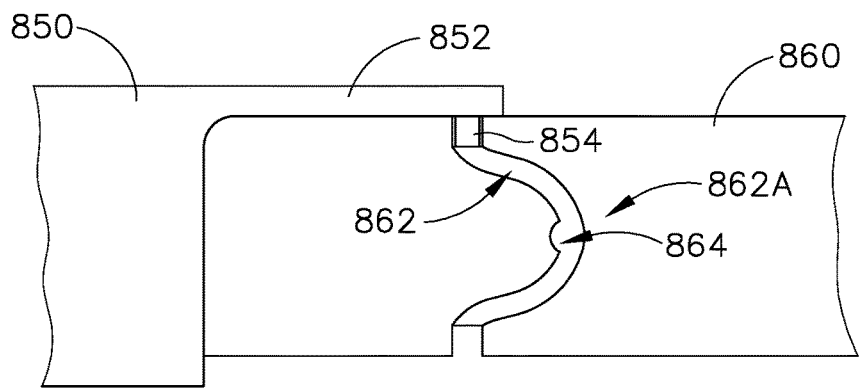
FIG. 79B depicts a detailed side elevational view of the tubular member of FIG. 77 coupled with the tubular guide of FIG. 78, with the tubular member moved to a second longitudinal position by rotation of the tubular guide to a second rotational position.
Figure 79C:
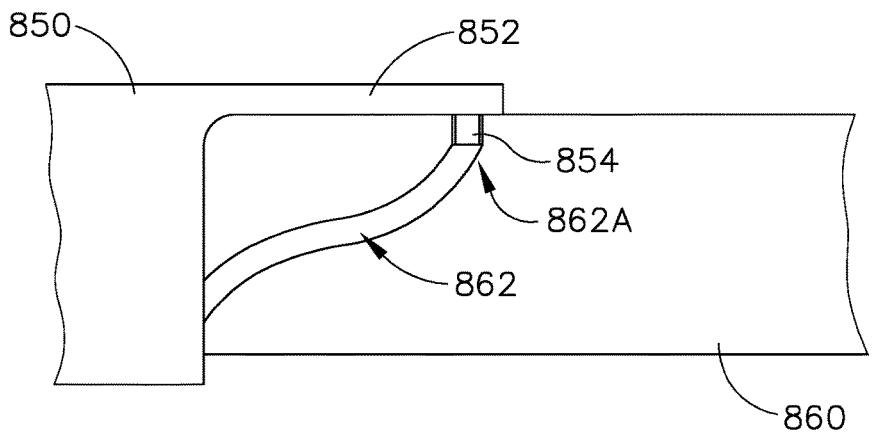
FIG. 79C depicts a detailed side elevational view of the tubular member of FIG. 77 coupled with the tubular guide of FIG. 78, with the tubular member moved to a third longitudinal position by rotation of the tubular guide to a third rotational position.
Figure 80A:
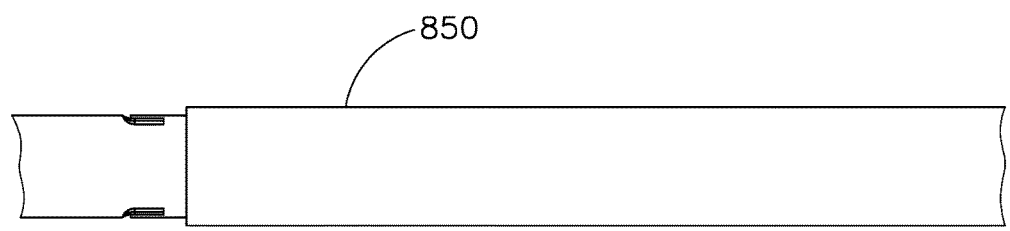
FIG. 80A depicts a detailed side elevational view of the tubular member of FIG. 77 in the first longitudinal position relative to an articulation section.
Figure 80B:
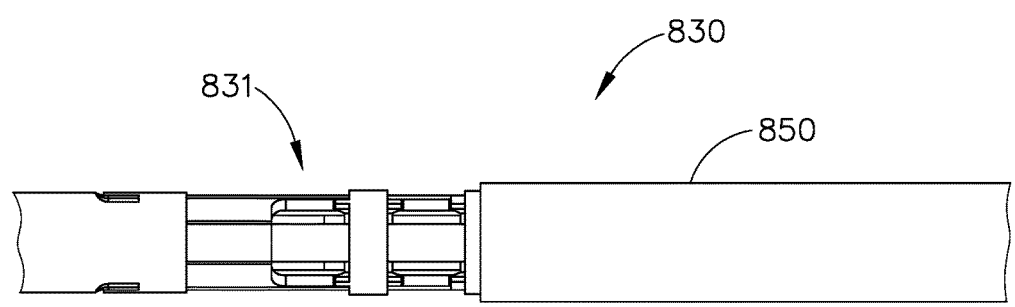
FIG. 80B depicts a detailed side elevational view of the tubular member of FIG. 77 moved to the second longitudinal position relative to the articulation section of FIG. 80A.
Figure 80C:
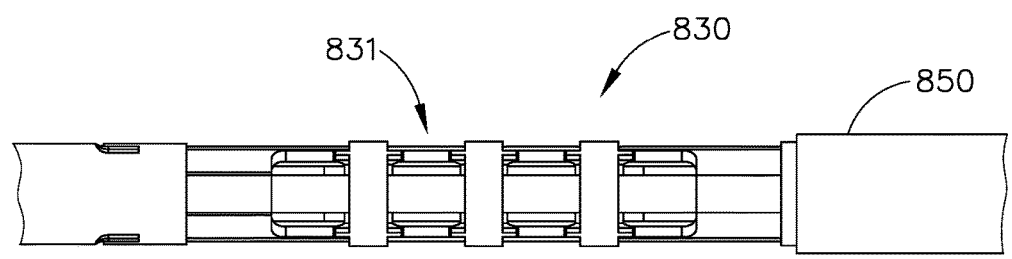
FIG. 80C depicts a detailed side elevational view of the tubular member of FIG. 77 moved to the third longitudinal position relative to the articulation section of FIG. 80A.

FIGS. 79A-80C show several of the above described components interacting to provide rigidity to articulation section (831) and/or to prevent inadvertent deflection of end effector (840) relative to outer sheath (832). In FIGS. 79A and 80A, articulation section (831) is in a substantially straight configuration and elongate tube member (850) covers articulation section (831), thereby rigidizing articulation section (831). Then, tubular guide member (860) is rotated about the longitudinal axis of shaft assembly (830), which causes elongate tube member (850) to translate proximally as pawl (854) travels along cam channel (862) as shown in FIG. 79B. This proximal translation of elongate tube member (850) exposes a portion of articulation section (831) as shown in FIG. 80B. As the operator continues rotating tubular guide member (860) about the longitudinal axis of shaft assembly (830) as shown in FIG. 79C, the above described interactions continue in the same fashion, resulting in further proximal translation of elongate tube member (850) due to engagement of pawl (854) in cam channel (862) until pawl (854) engages detent (864). As shown in FIG. 80C, this further proximal translation of elongate tube member (850) completely exposes articulation section (831) such that articulation section (831) may be articulated. It should be understood that further rotation of tubular guide member (860) in the same direction (or reversal of rotation of tubular guide member (860)) will cause distal translation of elongate tube member (850) back to the distal longitudinal position shown in FIGS. 79A and 80A due to engagement of pawl (854) in cam channel (862).

It should also be understood that the receipt of pawl (854) in detent (864) may provide the operator with tactile feedback indicating that elongate tube member (850) has reached the fully proximal position. Cooperation between pawl (854) and detent (864) may also provide some degree of resistance to inadvertent rotation of tubular guide member (860), thereby providing some degree of resistance to distal translation of elongate tube member (850). Such resistance may be particularly desirable in versions where elongate tube member (850) is resiliently biased toward the distal position.

Tubular guide member (860) may be actuated in various ways. For instance, at least a portion of tubular guide member (860) may be exposed such that the operator may directly grasp tubular guide member (860) to rotate tubular guide member (860). As another merely illustrative example, tubular guide member (860) may include a knob or other user input feature that the operator may grasp or otherwise manipulate to rotate tubular guide member (860). As yet another merely illustrative example, tubular guide member (860) may be operatively coupled with an articulation control assembly such as articulation control assembly (100, 400, 700). In some such versions, the articulation control assembly may automatically actuate tubular guide member (860) to drive elongate tube member (850) to the distal position when articulation section (830) reaches the straight, non-articulated configuration. The articulation control assembly may also automatically actuate tubular guide member (860) to drive elongate tube member (850) to the proximal position when the operator actuates the articulation control assembly to drive articulation section (830) toward an articulated configuration. Elongate tube member (850) may thus be actuated in a manner similar to rod member (740) described above. Still other suitable ways in which elongate tube member (850) and/or tubular guide member (860) may be actuated will be apparent to those of ordinary skill in the art in view of the teachings herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus for operating on tissue, the apparatus comprising: (a) a body assembly; (b) a shaft assembly, wherein the shaft assembly extends distally from the body assembly, wherein the shaft assembly defines a longitudinal axis; (c) an end effector, wherein the end effector is located at a distal end of the shaft assembly, wherein the end effector comprises an ultrasonic blade; (d) an articulation section, wherein the articulation section is coupled with the shaft assembly, wherein the articulation section is operable to articulate to thereby deflect the end effector from the longitudinal axis; and (e) an articulation control assembly, wherein the articulation control assembly comprises: (i) a first threaded member having a first pitch orientation, (ii) a second threaded member having a second pitch orientation, and (iii) an articulation control, wherein the articulation control is configured to rotate about an axis of rotation to thereby drive articulation of the articulation section by causing translation of the first and second threaded members along a path that is parallel to the longitudinal axis of the shaft assembly, wherein the axis of rotation of the articulation control is oriented obliquely or perpendicular to the longitudinal axis of the shaft assembly.

Example 2

The apparatus of Example 1 or any of the following Examples, wherein the articulation section comprises: (i) a first translatable member in communication with the first threaded member, and (ii) a second translatable member in communication with the second threaded member, wherein the first translatable member and the second translatable member are longitudinally translatable relative to each other.

Example 3

The apparatus of any of the preceding or following Examples, wherein the shaft assembly comprises an acoustic waveguide acoustically coupled with the ultrasonic blade, wherein the acoustic waveguide has a flexible portion, wherein the flexible portion extends through the articulation section.

Example 4

The apparatus of any of the preceding or following Examples, wherein the articulation control assembly further comprises a rotatable housing, wherein the rotatable housing comprises a proximal threading and a distal threading, wherein the first threaded member is engaged with the proximal threading, wherein eh second threaded member is engaged with the distal threading, wherein the rotatable housing is configured to rotate in a single direction to thereby cause translation of the first and second threaded members in opposite directions.

Example 5

The apparatus of Example 5, wherein the articulation control comprises a bevel gear, wherein the rotatable housing comprises a bevel gear, wherein the bevel gear of the articulation control is engaged with the bevel gear of the rotatable housing.

Example 6

The apparatus of any of the preceding or following Examples, wherein the body assembly comprises a handle assembly.

Example 7

The apparatus of Example 6, wherein the handle assembly comprises: (i) a pistol grip, and (ii) a trigger, wherein the trigger is pivotable toward and away from the pistol grip, wherein the articulation control comprises a knob positioned near the trigger such that the knob and the trigger may both be manipulated by a single hand grasping the pistol grip.

Example 8

The apparatus of any of the preceding or following Examples, wherein the articulation control assembly further comprises a cylindrical guide, wherein the first threaded member and the second threaded member are operable to translate along a length of the cylindrical guide, wherein the cylindrical guide is configured to maintain a rotational position of the first threaded member and the second threaded member.

Example 9

The apparatus of any of the preceding or following Examples, wherein the articulation control comprises an articulation knob.

Example 10

The apparatus of Example 9, wherein the articulation knob is rotatable about an axis of rotation that is oriented perpendicular to the longitudinal axis of the shaft assembly.

Example 11

The apparatus of any of the preceding or following Examples, wherein the articulation control comprises an axle coupled with a motor.

Example 12

The apparatus of Example 11, wherein the axis of rotation of the axle is oriented obliquely to the longitudinal axis of the shaft assembly.

Example 13

The apparatus of any of the preceding or following Examples, wherein the apparatus further comprises a member, wherein the rigidizing member is operable to translate relative to the articulation section to thereby selectively rigidize the articulation section.

Example 14

The apparatus of Example 13, wherein the articulation control assembly is further operable to drive the rigidizing member.

Example 15

The apparatus of Example 13, wherein the rigidizing member is configured to selectively translate into and out of the articulation section to thereby selectively rigidize the articulation section.

Example 16

The apparatus of Example 13, further comprising a rotatable member having cam channel coupled with the rigidizing member, wherein the cam channel is rotatable about a longitudinal axis, wherein the cam channel is obliquely oriented relative to the longitudinal axis such that the cam channel is configured to drive the rigidizing member longitudinally in response to rotation of the rotatable member about the longitudinal axis.

Example 17

An apparatus for operating on tissue, the apparatus comprising: (a) a body assembly; (b) a shaft assembly, wherein the shaft assembly extends distally from the body assembly, wherein the shaft assembly defines a longitudinal axis; (c) an end effector, wherein the end effector is located at a distal end of the shaft assembly; (d) an articulation section, wherein the articulation section is coupled with the shaft assembly, wherein the articulation section is operable to articulate to thereby deflect the end effector from the longitudinal axis; and (e) an articulation control assembly, wherein the articulation control assembly comprises: (i) a proximal rotatable housing, wherein the proximal rotatable housing comprises threading, (ii) a distal rotatable housing, wherein the distal rotatable housing comprises a proximal threading and a distal threading, (iii) a first lead screw, wherein the first lead screw is configured to threadably engage the threading of the proximal rotatable housing, wherein the first lead screw is configured to translate to thereby limit deflection of the end effector by limiting the flexibility of the articulation section, wherein the proximal rotatable housing is configured to rotate to thereby cause translation of the first lead screw, (iv) a second lead screw, wherein the second lead screw is configured to threadably engage the proximal threading of the distal rotatable housing, and (v) a third lead screw, wherein the third lead screw is configured to threadably engage the distal threading of the distal rotatable housing, wherein the second lead screw and the third lead screw are configured to translate in opposite directions to thereby drive articulation of the articulation section, wherein the distal rotatable housing is configured to rotate in a single direction to thereby cause translation of the first lead screw and the second lead screw in opposite directions.

Example 18

An apparatus for operating on tissue, the apparatus comprising: (a) a body assembly; (b) a shaft assembly, wherein the shaft assembly extends distally from the body assembly, wherein the shaft assembly defines a longitudinal axis; (c) an end effector, wherein the end effector is located at a distal end of the shaft assembly; (d) an articulation section, wherein the articulation section is coupled with the shaft assembly, wherein the articulation section is operable to articulate to thereby deflect the end effector from the longitudinal axis; and (e) a rigidizing assembly, wherein the rigidizing assembly comprises: (i) a rigidizing member, wherein the rigidizing member is configured to translate relative to the articulation section to thereby selectively ridigize the articulation section, and (ii) a rotatable member, wherein the rotatable member is configured to rotate to thereby cause translation of the rigidizing member.

Example 19

The apparatus of Example 18, wherein the rotatable member comprises a lead screw.

Example 20

The apparatus of Example 18, wherein the rotatable member comprises a guide tube.

V. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
    (a) a body assembly, wherein the body assembly comprises a barrel portion, a pistol grip, and a trigger that is pivotable relative to the pistol grip;
    (b) a shaft assembly, wherein the shaft assembly extends distally from the body assembly, wherein the shaft assembly defines a longitudinal axis;
    (c) an end effector, wherein the end effector is located at a distal end of the shaft assembly, wherein the end effector comprises an ultrasonic blade;
    (d) an articulation section, wherein the articulation section is coupled with the shaft assembly, wherein the articulation section is operable to articulate to thereby deflect the end effector from the longitudinal axis along a plane of articulation; and
    (e) an articulation control assembly, wherein the articulation control assembly comprises:
        (i) a first threaded member having a first pitch orientation,
        (ii) a second threaded member having a second pitch orientation, and
        (iii) an articulation control,
        wherein the articulation control is configured to rotate about an axis of rotation to thereby drive articulation of the articulation section by causing translation of the first and second threaded members along a path that is parallel to the longitudinal axis of the shaft assembly,
        wherein the articulation control is configured to rotate on a plane of rotation that is parallel to the plane of articulation;
        wherein the articulation control is positioned distal to the pistol grip;
        wherein the pistol grip, the trigger, and the articulation control are each positioned below the longitudinal axis of the shaft assembly;
        wherein the axis of rotation of the articulation control is oriented obliquely or perpendicular to the longitudinal axis of the shaft assembly.

2. The apparatus of claim 1, wherein the articulation section comprises:
    (i) a first translatable member in communication with the first threaded member, and
    (ii) a second translatable member in communication with the second threaded member, wherein the first translatable member and the second translatable member are longitudinally translatable relative to each other.

3. The apparatus of claim 1, wherein the shaft assembly comprises an acoustic waveguide acoustically coupled with the ultrasonic blade, wherein the acoustic waveguide has a flexible portion, wherein the flexible portion extends through the articulation section.

4. The apparatus of claim 1, wherein the articulation control assembly further comprises a rotatable housing, wherein the rotatable housing comprises a proximal threading and a distal threading, wherein the first threaded member is engaged with the proximal threading, wherein the second threaded member is engaged with the distal threading, wherein the rotatable housing is configured to rotate in a single direction to thereby cause translation of the first and second threaded members in opposite directions.

5. The apparatus of claim 4, wherein the articulation control comprises a bevel gear, wherein the rotatable housing comprises a bevel gear, wherein the bevel gear of the articulation control is engaged with the bevel gear of the rotatable housing.

6. The apparatus of claim 1,
wherein the trigger is pivotable toward and away from the pistol grip,
wherein the articulation control comprises a knob positioned near the trigger such that the knob and the trigger may both be manipulated by a single hand grasping the pistol grip.

7. The apparatus of claim 1, wherein the articulation control assembly further comprises a cylindrical guide, wherein the first threaded member and the second threaded member are operable to translate along a length of the cylindrical guide, wherein the cylindrical guide is configured to maintain a rotational position of the first threaded member and the second threaded member.

8. The apparatus of claim 1, wherein the articulation control comprises an articulation knob.

9. The apparatus of claim 8, wherein the articulation knob is rotatable about an axis of rotation that is oriented perpendicular to the longitudinal axis of the shaft assembly.

10. The apparatus of claim 1, wherein the articulation control comprises an axle coupled with a motor.

11. The apparatus of claim 10, wherein the axis of rotation of the axle is oriented obliquely to the longitudinal axis of the shaft assembly.

12. The apparatus of claim 1, wherein the apparatus further comprises a rigidizing member, wherein the rigidizing member is operable to translate relative to the articulation section to thereby selectively rigidize the articulation section, wherein the rigidizing member is rigid, wherein the rigidizing member is configured to maintain its rigidity as the rigidizing member translates relative to the articulation section.

13. The apparatus of claim 12, wherein the articulation control assembly is further operable to drive the rigidizing member.

14. The apparatus of claim 12, wherein the rigidizing member is configured to selectively translate into and out of the articulation section to thereby selectively rigidize the articulation section.

15. The apparatus of claim 12, further comprising a rotatable member having cam channel coupled with the rigidizing member, wherein the cam channel is rotatable about a longitudinal axis, wherein the cam channel is obliquely oriented relative to the longitudinal axis such that the cam channel is configured to drive the rigidizing member longitudinally in response to rotation of the rotatable member about the longitudinal axis.

16. The apparatus of claim 1, wherein the barrel portion is disposed above both the pistol grip and the trigger.

17. An apparatus for operating on tissue, the apparatus comprising:

(a) a body assembly;
(b) a shaft assembly, wherein the shaft assembly extends distally from the body assembly, wherein the shaft assembly defines a longitudinal axis;
(c) an end effector, wherein the end effector is located at a distal end of the shaft assembly;
(d) an articulation section, wherein the articulation section is coupled with the shaft assembly, wherein the articulation section is operable to articulate to thereby deflect the end effector from the longitudinal axis; and
(e) an articulation control assembly, wherein the articulation control assembly comprises:
  (i) a proximal rotatable housing, wherein the proximal rotatable housing comprises threading,
  (ii) a distal rotatable housing, wherein the distal rotatable housing comprises a proximal threading and a distal threading,
  (iii) a first lead screw, wherein the first lead screw is configured to threadably engage the threading of the proximal rotatable housing, wherein the first lead screw is configured to translate to thereby limit deflection of the end effector by limiting the flexibility of the articulation section, wherein the proximal rotatable housing is configured to rotate to thereby cause translation of the first lead screw,
  (iv) a second lead screw, wherein the second lead screw is configured to threadably engage the proximal threading of the distal rotatable housing, and
  (v) a third lead screw, wherein the third lead screw is configured to threadably engage the distal threading of the distal rotatable housing, wherein the second lead screw and the third lead screw are configured to translate in opposite directions to thereby drive articulation of the articulation section, wherein the distal rotatable housing is configured to rotate in a single direction to thereby cause translation of the first lead screw and the second lead screw in opposite directions.

18. An apparatus for operating on tissue, the apparatus comprising:

(a) a shaft assembly, wherein the shaft assembly extends distally from the body assembly, wherein the shaft assembly defines a longitudinal axis;
(b) an end effector, wherein the end effector is located at a distal end of the shaft assembly;
(c) an articulation section, wherein the articulation section is coupled with the shaft assembly, wherein the articulation section is operable to articulate to thereby deflect the end effector from the longitudinal axis; and
(d) a rigidizing assembly, wherein the rigidizing assembly comprises:
  (i) a rigidizing member, wherein the rigidizing member is configured to translate relative to the articulation section to thereby selectively ridigize the articulation section, wherein the rigidizing member is rigid, wherein the rigidizing member is configured to maintain its rigidity as the rigidizing member translates relative to the articulation section, and
  (ii) a rotatable member, wherein the rotatable member is configured to rotate to thereby cause translation of the rigidizing member.

19. The apparatus of claim 18, wherein the rotatable member comprises a lead screw.

20. The apparatus of claim 18, wherein the rotatable member comprises a guide tube.

* * * * *

UNITED STATES PATENT AND TRADEMARK OFFICE
CERTIFICATE OF CORRECTION

PATENT NO. : 10,342,567 B2
APPLICATION NO. : 14/688663
DATED : July 9, 2019
INVENTOR(S) : Hibner et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 555 days.

Signed and Sealed this
Twenty-eighth Day of January, 2020

Andrei Iancu
*Director of the United States Patent and Trademark Office*